US011528895B2

(12) United States Patent
Macdonald et al.

(10) Patent No.: US 11,528,895 B2
(45) Date of Patent: *Dec. 20, 2022

(54) GENETICALLY MODIFIED T CELL RECEPTOR MICE

(71) Applicant: Regeneron Pharmaceuticals, Inc., Tarrytown, NY (US)

(72) Inventors: Lynn Macdonald, Harrison, NY (US); Andrew J. Murphy, Croton-on-Hudson, NY (US); John McWhirter, Greenville, NC (US); Naxin Tu, Pleasantville, NY (US); Vera Voronina, North Bethesda, MD (US); Cagan Gurer, Chappaqua, NY (US); Karolina Meagher, Yorktown Heights, NY (US); Sean Stevens, Del Mar, CA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/799,355

(22) Filed: Jul. 14, 2015

(65) Prior Publication Data

US 2016/0021856 A1  Jan. 28, 2016

Related U.S. Application Data

(63) Continuation of application No. 13/661,342, filed on Oct. 26, 2012, now Pat. No. 9,113,616.

(60) Provisional application No. 61/700,908, filed on Sep. 14, 2012, provisional application No. 61/621,198, filed on Apr. 6, 2012, provisional application No. 61/552,582, filed on Oct. 28, 2011.

(51) Int. Cl.
*A01K 67/027* (2006.01)
*C07K 14/725* (2006.01)
*C12N 15/85* (2006.01)

(52) U.S. Cl.
CPC ...... *A01K 67/0278* (2013.01); *C07K 14/7051* (2013.01); *C12N 15/8509* (2013.01); *A01K 2207/15* (2013.01); *A01K 2217/072* (2013.01); *A01K 2217/15* (2013.01); *A01K 2227/105* (2013.01); *A01K 2267/0387* (2013.01); *C07K 2319/00* (2013.01); *C12N 2800/204* (2013.01); *C12N 2800/30* (2013.01)

(58) Field of Classification Search
USPC ............................................... 800/3, 18
See application file for complete search history.

(56) References Cited

U.S. PATENT DOCUMENTS

| 5,175,384 A | 12/1992 | Krimpenfort et al. |
| 5,859,312 A | 1/1999 | Littman et al. |
| 5,942,435 A | 8/1999 | Wheeler |
| 6,150,584 A | 11/2000 | Kucherlapati et al. |
| 6,586,251 B2 | 7/2003 | Economides et al. |
| 6,596,541 B2 | 7/2003 | Murphy et al. |
| 7,105,348 B2 | 9/2006 | Murphy et al. |
| 7,294,754 B2 | 11/2007 | Poueymirou et al. |
| 7,462,486 B2 | 12/2008 | Vandernbark |
| 7,569,664 B2 | 8/2009 | Jakobsen et al. |
| 7,763,718 B2 | 7/2010 | Jakobsen et al. |
| 9,113,616 B2 * | 8/2015 | MacDonald ....... A01K 67/0278 |
| 2003/0093818 A1 | 5/2003 | Belmont et al. |
| 2005/0066375 A1 | 3/2005 | Thiam et al. |
| 2007/0209083 A1 | 9/2007 | Thiam et al. |
| 2008/0152131 A1 | 6/2008 | Jakobsen et al. |
| 2009/0304657 A1 | 12/2009 | Morgan et al. |
| 2009/0328240 A1 | 12/2009 | Sing et al. |
| 2010/0011452 A1 | 1/2010 | Tomizuka et al. |
| 2010/0175141 A1 | 7/2010 | Collins et al. |
| 2011/0158957 A1 | 6/2011 | Bonini et al. |
| 2011/0243995 A1 | 10/2011 | Voss et al. |

FOREIGN PATENT DOCUMENTS

| CA | 2471392 A1 | 8/2003 |
| EP | 1409646 B1 | 6/2012 |
| WO | 1997032603 A1 | 9/1997 |
| WO | 1998024893 A2 | 6/1998 |
| WO | 2001027291 A1 | 4/2001 |
| WO | 2002059263 A2 | 8/2002 |
| WO | 2002066630 A1 | 8/2002 |
| WO | 2004042004 A2 | 5/2004 |
| WO | 2007131092 A2 | 11/2007 |
| WO | 2009114400 A1 | 9/2009 |
| WO | 2012071592 A2 | 5/2010 |
| WO | 2010107400 A1 | 9/2010 |
| WO | 2011004192 A1 | 1/2011 |

(Continued)

OTHER PUBLICATIONS

Wall (1996, Theriogenology, vol. 45, p. 57-68).*
Campbell (Theriogenology, 1997, vol. 47(1), 63-72).*
Tong (Nature, 2010, 467, p. 211-215).*
Shirwan (J. Immunol., 1995, vol. 154, p. 1964-1972).*
Dupic, PLoS Computational Biol., 2019, vol. 15, Nol. 3, e1006874, p. 1-19.*
Slide presentation given by Regeneron on Mar. 1, 2007—see Declaration filed Jul. 9, 21.*
Linnenbach et al. (1980) "DNA-transformed murine teratocarcinoma cells: regulation of expression of simian virus 40 tumor antigen in stem versus differentiated cells," PNAS, 77(8):4875-4879.

(Continued)

*Primary Examiner* — Michael C Wilson
(74) *Attorney, Agent, or Firm* — Rita S. Wu; Margarita Zippin; FisherBroyles, LLP

(57) ABSTRACT

The invention provides a genetically modified non-human animal that comprises in its genome unrearranged T cell receptor variable gene loci, as well as embryos, cells, and tissues comprising the same. Also provided are constructs for making said genetically modified non-human animal and methods of making the same. Various methods of using the genetically modified non-human animal are also provided.

19 Claims, 31 Drawing Sheets

Specification includes a Sequence Listing.

(56) References Cited

FOREIGN PATENT DOCUMENTS

| WO | 2011039508 A2 | 4/2011 |
|---|---|---|
| WO | 2011044186 A1 | 4/2011 |
| WO | 2012039779 A1 | 3/2012 |
| WO | 2016164492 A2 | 10/2016 |

OTHER PUBLICATIONS

Li et al. (2010) "Transgenic mice with a diverse human T Cell antigen receptor repertoire," Nature Med., 16 (9):1029-1035.
Love and Hayes (2010) "ITAM-Mediated Signaling by the T-Cell Antigen Receptor," Cold Spring Harb. Perspecl. Biol., 2:e002485.
Mackay (1999) "Dual personality of memory T cells," Nature, 401 659-660.
Madsen et al. (1999) "A humanized model for multiple sclerosis using HLA-DR2 and a human T-cell receptor," Nature Genet., 23:343-347.
Mantovani et al. (2002) Dominant TCR-alpha Requirements for a Self Antigen Recognition in Humans, J. Immunol., 169:6253-6260.
McMurry et al. (1997) "Enhancer Control of Local Accessibility to V(D)J Recombinase," Mol. Cell Biol., 17:4553-4561.
Mendez et al. (1997) "Functional transplant of megabase human immunoglobulin loci recapitulates human antibody response in mice," Nature Genet., 15(2):146-156.
Mombaerts et al. (1991) "Creation of a large genomic deletion at the T-cell antigen receptor bela-subunit locus in mouse embryonic stem cells by gene targeting," PNAS, 88:3084-3087.
Mombaerts et al. (1992) "Mutations in T-cell antigen receptor genes alpha and bela block thymocyte development at different stages," Nature, 360:225-231.
Mombaerts et al. (1993) "Spontaneous Development of Inflammatory Bowel Disease in T Cell Receptor Mutant Mice," Cell, 75:275-282.
Morgan et al. (2006) "Cancer Regression in Patients After Transfer of Genetically Engineered Lymphocytes," Science, 314:126-129.
NCBI Accession No. NG_001332.2 (2012) "*Homo sapiens* T cell receptor alpha delta locus (TCRA/TCRD) on chromosome 14," NCBI, 2 pages.
Nooordzij et al. (2000) "N-terminal truncated human RAG1 proteins can direct T-cell receptor but not immunoglobulin gene rearrangements," Blood, 96(1):203-209.
Pasare et al. (2001) "T cells in mice expressing a transgenic human TCR β chain get positively selected but cannot be activated in the periphery by signaling through TCR," Internal. Immunol., 13(1):53-62.
Pascolo, et al. (1997) "HLA-A2.1-restricted Education and Cytolytic Activity of CD8+ T Lymphocytes from from β2 Microglobulin (β2m) HLA-A2.1 Monochain Transgenic H-2Db β2m Double Knockout Mice," J. Exp. Med., 185:2043-2051.
Poueymirou et al. (2007) "F0 generation mice fully derived from gene-targeted embryonic stem cells allowing immediate phenotypic analyses," Nature Biotech., 25:91-99.
Rack, et al. (1997) "A chromosome 14q11/TCRalpha/delta specific yeast artificial chromosome improves the detection rate and characterization of chromosome abnormalities in T-Lymphoproliferative disorders," Blood, 90:1233-1240.
Ravetech and Lanier (2000) "Immune Inhibitory Receptors," Science, 290:84-89.
Restifo et al. (2012) "Adoptive immunotherapy for cancer: harnessing the T cell response," Nature Reviews, 12:269-281.
Richman et al. (2009) "Structural features of T cell receptor variable regions that enhance domain stability and enable expression as single-chain ValphaVbeta fragments," Mol. Immunol., 43:902-916.
Rosenberg et al. (2011) "Durable Complete Responses in Heavily Pretreated Patients with Metastatic Melanoma Using T-Cell Transfer," Immunotherapy, 17:4550-4557.
Rothe et al. (1993) "Functional expression of a human TCRbeta gene in transgenic mice," Internal. Immunol., 5:11-17.

Rowan et al. (1996) "The Complete 685-Kilobase DNA Sequence of the Human Beta T Cell Receptor Locus," Science, 272:1755-1762.
Sallusto et al. (1999) "Two subsets of memory T lymphocytes with distinct homing potentials and effector functions," Nature, 401:708-712.
Santagata et al. (2000) "The genetic and biochemical basis of Omenn syndrome," Immunol. Rev., 178:64-74.
Satyanarayana et al. (1988) "Genomic organization of the human T-cell antigen-receptor alpha/delta locus," PNAS, 85:8166-8170.
Schwarz et al. (1996) "RAG mutations in human B cell negative SCID," Science, 274(5284):97-99.
Sebzda et al. (1999) "Selection of the T Cell Repertoire," Annu. Rev. Immunol., 17:829-874.
Shani et al. (2009) "Incomplete T-cell receptor β peptides target the mitochondrion and induce apoptosis," Blood, 113:3530-3541.
Shinkai et al. (1992) "RAG-2-deficient mice lack mature lymphocytes owing to inability to initiate V(D)J rearrangement," Cell, 68(5):855-867.
Sim et al. (1984) "Primary structure of human T-cell receptor alpha-chain," Nature, 312:771-775.
Sleckman et al. (2000) "Mechanisms that direct ordered assembly of T cell receptor β locus V, D, and J gene segments," PNAS, 97(14)7975-7980.
Sommermeyer et al. (2010) "Minimal Amino Acids Exchange in Human TCR Constant Regions Fosters Improved Function of TCR Gene-Modified T cells," J. Immunol., 184:6223-6231.
Taneja and David (1998) "HLA Transgenic Mice as Humanized Mouse Models of Disease and Immunity," J. Clin. Invest., 101:921-926.
Taylor et al. (1994) "Human immunoglobulin transgenes undergo rearrangement, somatic mutation and class switching in mice that lack endogenous IgM," Int. Immunol., 6(4):579-591.
Thomas et al. (2010) "Molecular immunology lessons from therapeutic T-cell receptor gene transfer," Immunol., 129:170-177.
Toyonaga et al. (1985) "Organization and sequences of the diversity, joining, and constant region genes of the human T-cell receptor beta chain," PNAS, 82(24):8624-8628.
Uematsu et al. (1988) "In transgenic mice the introduced functional T cell receptor Beta Gene Prevents Expression of Endogenous Beta Genes," Cell, 52:831-841.
Valenzuela et al. (2003) "High-throughput engineering of the mouse genome coupled with high-resolution expression analysis," Nature Biotech., 21:652-659.
Van Meerwijk et al. (1990) "T-cell specific rearrangement of T-cell receptor Beta transgenes in mice," EMBO J., 9:1057-1062.
Villa, et al. (1998) "Partial V(D)J recombination activity leads to Omenn syndrome," Cell, 93(5): 885-896.
Villa, et al. (1999) "Omenn syndrome: a disorder of Ragl and Rag2 genes," J. Clin. Immunol., 19(2):87-97.
Viney et al. (1992) "Generation of Monoclonal Antibodies Against a Human T Cell Receptor Beta Chain Expressed in Transgenic Mice," Hybridoma, 11:701-713.
Vollmer et al. (2000) "Antigen contacts by Ni-reactive TCR: typical α β chain cooperation versus α chain-dominated specificity," Int. Immunol., 12(12):1723-1731.
Wagner et al. (1994) "Antibodies generated from human immunoglobulin miniloci in transgenic mice," Nucleic Acids Res., 22(8):1389-1393.
Wagner et al. (1994) "The diversity of antigen-specific monoclonal antibodies from transgenic mice bearing human immunoglobulin gene miniloci," Eur. J. Immunol., 24(11):2672-2681.
Wall (1996) "Transgenic Livestock: Progress and Prospects for the Future," Theriogenology, 45:57-68.
Wei et al. (1996) "Repertoire and Organization of Human T-Cell Receptor α Region Variable Genes," Short Communication, Genomics, 39:442-445, Article No. 0652.
Willemsen et al. (2003) "Genetic Engineering of T Cell Specificity for Immunotherapy of Cancer," Human Immunol., 64:56-68.
Abarrategui and Krangel (2006) "Regulation of T cell receptor alpha gene recombination by transcription," Nat. Immunol., 7:1109-1115 and Corrigendum.

(56) References Cited

OTHER PUBLICATIONS

Aggen et al. (2011) "Identification and engineering of human variable regions that allow expression of stable single-chain T cell receptors," Protein Eng., Design & Selection, 24:361-372.
Alvarez et al. (1995) "V(D)J Recombination and Allelic Exclusion of a TCR Beta-Chain Minilocus Occurs in the Absence of a Functional Promoter," J. of Immunol., 155:1191-1202.
Auerbach et al. (2000) "Establishment and Chimera Analysis of 129/SvEV-and C57BL/6-Derived Mouse Embryonic Stem Cell Lines," BioTechniques, 29:1024-1032.
Baer, et al. (1986) "Organization of the T-Cell receptor alpha-chain gene and rearrangement in human T-Cell leukemias," Mol. Biol. Med., 3:265-277.
Baker et al. (1996) "Adaptation of TCR Expression Vectors for the Construction of Mouse-Human Chimeric MBP-Specific TCR Transgenes," J. of Neuroscience Research, 45:487-491.
Barnden, et al. (1988) "Defective TCR expression in transgenic mice constructed using eDNA-based alpha-and beta-chain genes under the control of heterologous regulatory elements," Immunol. Cell Biol., 76:34-40.
Bassing et al. (2000) "Recombination signal sequences restrict chromosomal V(D)J recombination beyond the 12/23 rule," Nature, 405:583-586.
Bialer et al. (2010) "Selected Murine Residues Endow Human TCR with Enhanced Tumor Recognition," J. Immunol., 184:6232-6241.
Bonnet et al. (2009) "Molecular Genetics at the T-Cell Receptor β Locus: Insights into the Regulation of V(D)J Recombination," V(D)J Recombination, 650:116-132.
Bouffard et al. (1997) "A Physical Map of Human Chromosome 7: An Integrated YAC Contig Map with Average STS Spacing of 79 kb," Genome Res., 7:673-692, Cold Spring Harbor Laboratory Press, ISSN 1054-9803.
Boulter and Jakobsen (2005) "Stable, soluble, high-affinity, engineered T cell receptors: novel antibody-like proteins for specific targeting of peptide antigens," Clin. Exp. Immunol., 142:454-460.
Brehm et al. (2010) "Humanized Mouse Models to Study Human Diseases," Curr. Opin. Endocrinol. Diabetes Obes., 17:120-125.
Brusko et al. (2010) "Human Antigen-Specific Regulatory T cells Generated by T cell receptor Gene Transfer," PLoS ONE, 5:e11726, 12 pages.
Call and Wucherpfennig (2005) "The T cell receptor: Critical Role of the Membrane Environment in Receptor Assembly and Function," Annu. Rev. Immunol., 23:101-125.
Campbell (1997) "Totipotency or Multipotentiality of Cultured cells: Applications and Progress," Theriogenology, 47:(1), 63-72.
Capone, et al. (1995) "T Cell Development in TCR-alphabeta Transgenic Mice Analysis using V(D)J Recombination Substrates," J. Immunol., 5165-5172.
Carrasco et al. (2003) "A role for the cytoplasmic tail of the pre-T cell receptor (TCR) alpha chain in promoting constitutive internalization and degradation of the pre-TCR," J. Biol. Chem., 278:14507-14513.
Chhabra (2011) "TCR-Engineered, Customized, Antitumor T cells for Cancer Immunotherapy: Advantages and Limitations," The Scientific World J., 11:121-129.
Chung et al. (1994) "Functional three-domain single-chain T-Cell receptors," PNAS, 91:12654-12658.
Cohen, et al. (2006) "Enhanced Antitumor Activity of Murine-Human Hybrid T-Cell Receptor (TCR) in Human Lymphocytes is Associated with Improved Pairing and TCR/CD3 Stability," Cancer Res., 66:8878-8886.
Daniel-Meshulam et al. (2012) "How (specific) would you like your T-cells today? Generating T-Cell therapeutic function through TCR-gene transfer," Front. Immunol., 3:186, 13 pages.
Dietrich et al. (2003) "Prevalent Role of TCR alpha-chain in the Selection of the Preimmune Repertoire Specific for a Human Tumor-Associated Self-Antigen," J. Immunol., 170:5103-5109.
Epel et al. (2002) "A functional recombinant single-chain T cell receptor fragment capable of selectively targeting antigen-presenting cells," Cancer Immunol. Immunother., 51:565-573.

Ferrier et al. (1990) "Separate elements control DJ and VDJ rearrangement in a transgenic recombination substrate," EMBO J., 9:117-125.
Festing et al. (1999) "Revised nomenclature for strain 129 mice," Mamm. Genome, 10:836.
Fleischer et al. (1996) "Reactivity of Mouse T-Cell Hybridomas Expressing Human Vβ Gene Segments with Staphylococcal and Streptococcal Superantigens," Infect. and Immunity., 64(3):987-994.
Friese et al. (2006) "Humanized mouse models for organ-specific autoimmune diseases," Curr. Opin. Immunol., 18:704-709.
Fukui et al. (1997) "Differential requirement of MHC class II molecules expressed on hematopoietic cells for positive selection of CD4+ thymocytes in TCR α β and TCR β transgenic mice," Internal. Immunol., 9(9):1385-1391.
Ge and Stanley (2008) "The O-fucose glycan in the ligand-binding domain of Notch 1 regulates embryogenesis and T Cell development," PNAS, 105:1539-1544.
Germain et al. (2002) "T-Cell Development and The CD4-CD8 Lineage Decision," Nature Rev. Immunol., 2:309-322.
Glusman et al. (2001) "Comparative Genomics of the Human and Mouse T Cell Receptor Loci," Immunity, 15:337-349.
Godfrey et al. (1993) "Control Points in early T-Cell development," Immunol. Today, 14:547-553.
Haks et al. (1999) "Cell-fate decisions in early T Cell, development: regulation by cytokine receptors and the pre-TCR," Immunology, 11:23-37.
Holst, et al. (2006) "Generation of T-Cell receptor retrogenic mice," Nat. Protoc., 1:406-417.
Ishimoto et al. (1997) "In vitro and in vivo evidence for high frequency of I-Ab-reactive CD4+ T cells in HLA-DQ or HLA-DRA transgenic mice lacking endogenous MHC class I and/or class II expression," J. Immunol., 159(8):3717-3722.
Jakobovits (1994) "Humanizing the mouse genome," Cur. Biol., 4(8)761-763.
Johnson et al. (2009) "Gene therapy with human and mouse T-Cell receptors mediates cancer regression and targets normal tissues expressing cognate antigen," Blood, 114:535-546.
Khor et al. (2002) "Allelic exclusion at the TCR β locus," Curr. Opin. Immunol., 14:230-234.
Koop et al. (1994) "The human T-Cell receptor TCRAC/TCRDC (C alpha/C delta) region: organization, sequence, and evolution of 97.6 kb of DNA," Genomics, 19(3):478-493.
Kouskoff et al. (1995) "Cassette vectors directing expression of T cell receptor genes in transgenic mice," J. Immunol. Methods, 180:273-280.
Krangel et al. (1998) "Development regulation of V(D)J recombination at the TCR α/δ locus," Immunol. Rev., 165:131-147.
Kruisbeek et al. (2000) "Branching out to gain control: how the pre-TCR is linked to multiple functions," Rev. Immunology Today, 21(12):637-644.
Kuhns et al. (2006) "Deconstructing the Form and Function of the TCR/CD3 Complex," Immunity, 24:133-139.
Lauzurica et al. (1994) "Enhancer-dependent and-independent steps in the rearrangement of a human T cell receptor delta transgene," J. Exp. Med., 179:43-55.
Lauzurica et al. (1994) "Temporal and Lineage-specific control of T cell receptor alpha/delta gene rearrangement by T Cell, receptor alpha and delta enhancers," J. Exp. Med., 179:1913-1921.
Leduc, et al. (2000) "T Cell Development in TCR β Enhancer-Deleted Mice: Implications for α β T Cell Lineage Commitment and Differentiation," J. Immunol., 165:1364-1373.
Li et al. (2010) "Transgenic mice with a diverse human T Cell antigen receptor repertoire," Nature Med., 16, supplementary materials, 22 pages.
Li et al. (2013) "Generation of transgenic mice with megabase-sized human yeast artificial chromosomes by yeast spheroplast-embryonic stem cell fusion," Nat. Protoc., 8(8):1567-1582.
Linnemann et al. (2011) "T-Cell Receptor Gene Therapy: Critical Parameters for Clinical Success," J. Invest. Dermalol., 131:1806-1816.

(56) References Cited

OTHER PUBLICATIONS

Williams and Barclay et al. (1988) "The Immunoglobulin Superfamily-Domains for Cell Surface Recognition," Ann. Rev. Immunol., 6:381-405.
Wucherpfennig et al. (2010) "Structural Biology of the T-Cell Receptor: Insights into Receptor Assembly, Ligand Recognition, and Initiation of Signaling," Cold Spring Harb. Perspect. Biol., 2:a005140, 14 pages.
Xue et al. (2005) "Exploiting T cell receptor genes for cancer immunotherapy," Clin. Exp. Immunol., 139:167-172.
Yancopoulos et al. (1986) "Introduced T cell receptor variable region gene segments recombine in pre-B cells: evidence that B and T cells use a common recombinase," Cell, 44:251-259.
Yashiro-Ohtani et al. (2010) "Notch regulation of early thymocyte development," Seminars in Immunol., 22:261-269.
Yoshikai et al. (1985) "Organization and sequences of the variable, joining and constant region genes of the human T-Cell, receptor alpha-chain," Nature, 316(6031):837-840.
Zumla et al. (1992) "Co-expression of human T cell receptor chains with mouse CD3 on the Cell, surface of a mouse T Cell, hybridoma," J. Immunol. Methods., 149(1):69-76.
Zumla et al. (1992) "Use of a murine T-cell hybridoma expressing human T-Cell, receptor alpha-and betagene products as a tool for the production of human T-Cell, receptor-specific monoclonal antibodies," Hum. Immunol. 35(3):141-148.
Dennis (2002) "Welfare issues of genetically modified animals," ILAR Journal, 43(2):100-109.
Zhou et al., (2009) "Developing tTA transgenic rats for inducible and reversible gene expression," International Journal of Biological Sciences, 5:171-181.
Murphy, K., Travers, P., Walport, M., & Janeway, C. (2008) Janeway's Immunobiology. New York: Garland Science, 2008, at pp. 156-157.
Yakubke (Jakubke) et at. (1986) "Aminokisloty, peptidy, belki:" translated from German, Moscow, Mir, 1986,456 p. (p356-363) English Translation Only.
Kawamura et al. (2008) "Different Development of Myelin Basic Protein Agonist-and-Antagonist-Specific Human TCR Transgenic T Cells in the Thymus and Periphery," J. Immunol., 181(8):5462-5472.
Marten et al. (2003) "Transgenic mouse methods and protocols," Methods in Molecular Biology, 209:51-58.
Statement of Relatedness under MPEP 2001.06 with Respect to U.S. Appl. No. 14/799,355 dated Oct. 4, 2019.
Massimo et al. (2008) "Primer: Immunity and Autoimmunity," Diabetes, 57(11):2872-2882.
Extended European Search Report with respect to Europe Application No. 18176096.8, dated Oct. 1, 2018.
Kawamura et al. (2008) "Different Development of Myelin Basic Protein Agonist-and-Antagonist-Specific Human TTCR Transgenic T Cells in the Thymus and Periphery," J. Immunol, 181(8):5462-5472.
Declaration from Dr. Andrew Murphy regarding Mar. 1, 2007 meeting (81 pages), which includes the following Exhibits: Exhibit A: Agenda for meeting between "Regeneron and a Whole Bunch of Interested Academics" re "The Humanized TCR Mouse Project"; "Investigators (in alphabetical order)"; and "List of Relevant Papers" (4 pages). Exhibit B: "'Veloci-T': Humanization of mouse TCR and MHC" (19 slides). Exhibit C: "VelociGene and VelociMouse Background" (13 slides). Exhibit D: "VelocImmune Introduction" (16 slides). Exhibit E: "VelocImmune Phenotyping" (19 slides).
Barthold (2004) "Genetically altered mice: phenotypes, no phenotypes, and Faux phenotypes," Genetica, 122:75-88.
Brevini et al. (2010) "Embryonic Stem Cells in Domestic Animals; No shortcuts to pig embryonic stem cells," Theriogenology, 74:544-550.
Brouwers et al. (2015) "Unexpected Phenotypes in Mouse Models Carrying the Human Growth Hormone Minigene to Enhance Transgene Expression," Journal of Steroids & Hormonal Science, 6(2):1000. e115 (2 pages).
Cao et al., (2009) "Isolation and Culture of Primary Bovine Embryonic Stem Cell Colonies by a Novel Method," Journal of Experimental Zoology, 311A:368-376.
Carstea et al. (2009) "Germline competence of mouse ES and iPS Cell lines: Chimera technologies and genetic background," World Journals of Stem Cells, 1(1):22-29.
Choi et al., (2011) "Expression of the metabotropic glutamate receptor 5 (mGluR5) induces melanoma in transgenic mice," PNAS, 108(37):1519-15224.
Crusio et al. (2004) "Flanking Gene and Genetic Background Problems in Genetically Manipulated Mice," Biol. Psychiatry, 56:381-385.
Doetschman (2009) "Influence of Genetic Background on Genetically Engineered Mouse Phenotypes," Methods Mol. Biol., 530:423-433.
Friese et al., (2008) "Opposing effects of HLA class 1 molecules in tuning autoreactive CD8+ T cells in multiple scelerosis," Nature Med., 14(11): 1227-1235.
Glick and Pasternak Dzh. Moleculyarnaya biotehnologiya. Printsipy i primeneniye. Moscow: Mir, 2002 (with English translation).
Goldman et al. (2004) "Transgenic animals in medicine: Integration and expression of foreign genes, theoretical and applied aspects," Med. Sci. Monit., 10(11): RA274-285.
Hall (2008) "Porcine Embryonic Stem Cells: A Possible Source for Cell Replacement Therapy," Stem Cell Rev., 4:275-282.
Houdebine, et al (2002) "The methods to generate transgenic animals and to control transgene expression," J. of Biotech., 98:145-160.
Houdebine, et al. (2007) "Transgenic Animal Models in Biomedical Research," Methods in Molecular Biology, 360:163-202.
Houdebine (2009) "Methods to Generate Transgenic Animals," Genetic Engineering in Livestock, New Applications and Interdisciplinary Perspectives, Engelhard M, et al., 2009, XVI, 1 46 p. 8 illus., pp. 31-48, see p. 36.
Kawamata and Ochiya (2010) "Generation of genetically modified rats from embryonic stem cells," PNAS, 107(32):14223-14228.
Lavial et al., (2008) "Molecular control of pluripotency and germ line competency in chicken embryonic stem cells," Cell Research, 18:s106 (1 page).
Linder C. (2006) "Genetic Variables That Influence Phenotype," ILAR Journal, 47(2):132-140.
Manz et al. (2009) "Renaissance for mouse models of human hematopoiesis and immunobiology," Nature Immunology, 10(10):1039-1042.
Murphy and Silha (2000) "Unexpected and unexplained phenotypes in transgenic models," Growth Hormone & IGF Research, 10:233-235.
Shinohara et al. (2007) "Active integration: new strategies for transgenesis," Transgenic Res., 16:333-339.
Sittig et al. (2016) "Genetic Background Limits Generalizability of Genotype-Phenotype Relationships," Neuron, 91(6):1253-1359.
YANTHA et al., (2010) "Unexpected Acceleration of Type 1 Diabetes by Transgenic Expression of B7-H1 in NOD Mouse Peri-Islet Glia," Diabetes, 59:2588-2596.
Zhu et al. (2019) "Humanising the mouse genome piece by piece," Nature Communications, 10(1845):1-13.
Statement of Relatedness under MPEP 2001.06 with Respect to U.S. Appl. No. 14/799,355 dated Jul. 9, 2021.
Lefranc, M. (2003) "IMGT, the international ImMunoGeneTics database," Nucleic Acids Research, 31(1):307-310.
Statement of Relatedness under MPEP 2001.06 with Respect to U.S. Appl. No. 14/799,355 dated Dec. 21, 2021.

\* cited by examiner

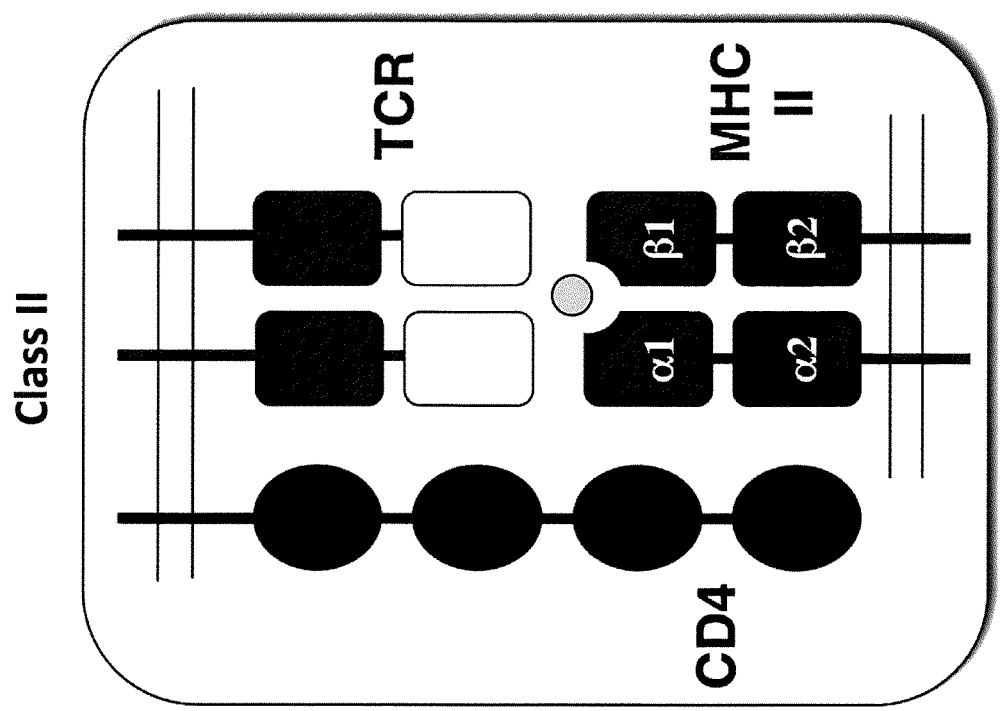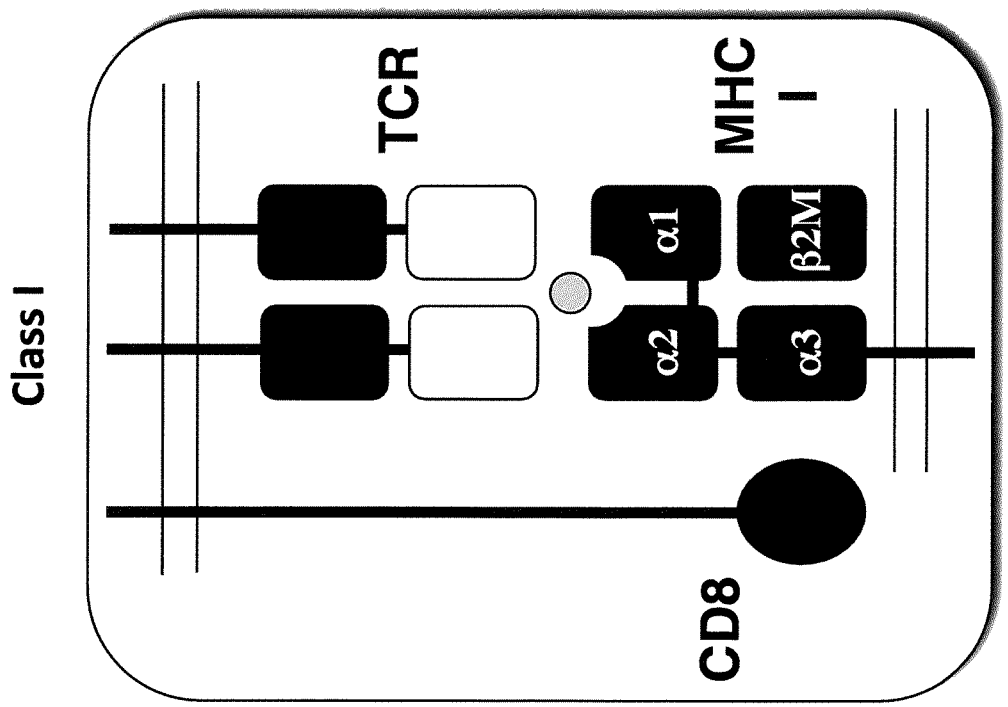
FIG. 1

FIG. 15A      Percent of CD8 T cells expressing hTRBV

| | TRBV-18 | TRBV-19 | TRBV-20 | TRBV-25 | TRBV-27 | TRBV-28 | TRBV-29 |
|---|---|---|---|---|---|---|---|
| WT | 0.03 ± 0.01 | 0.00 ± 0.00 | 0.00 ± 0.00 | 0.01 ± 0.01 | 0.01 ± 0.00 | 0.02 ± 0.02 | 0.01 ± 0.01 |
| 1716 HO | 0.06 ± 0.03 | 0.01 ± 0.01 | 2.68 ± 0.51 | 1.20 ± 0.09 | 13.53 ± 0.71 | 10.07 ± 1.63 | 0.00 ± 0.00 |
| 1716 HO 1767 HO | 0.07 ± 0.05 | 0.01 ± 0.01 | 1.89 ± 0.35 | 1.12 ± 0.11 | 6.71 ± 0.57 | 7.00 ± 0.65 | 0.00 ± 0.00 |

FIG. 15B      Percent of CD4 T cells expressing hTRBV

| | TRBV-18 | TRBV-19 | TRBV-20 | TRBV-25 | TRBV-27 | TRBV-28 | TRBV-29 |
|---|---|---|---|---|---|---|---|
| WT | 0.03 ± 0.02 | 0.0 ± 0.0 | 0.0 ± 0.0 | 0.03 ± 0.02 | 0.01 ± 0.0 | 0.02 ± 0.02 | 0.00 ± 0.01 |
| 1716 HO | 0.05 ± 0.02 | 0.01 ± 0.00 | 2.35 ± 0.46 | 0.52 ± 0.04 | 2.88 ± 0.19 | 3.82 ± 0.66 | 0.00 ± 0.00 |
| 1716 HO 1767 HO | 0.05 ± 0.03 | 0.01 ± 0.0 | 2.08 ± 0.15 | 0.23 ± 0.06 | 1.57 ± 0.18 | 2.59 ± 0.24 | 0.00 ± 0.00 |

Whole spleen and thymus. mRNA normalized to mTCRb constant 1 (n=4 mice per group).
ND=not detected (Ct≥35)

Whole spleen and thymus. mRNA normalized to mTCRb constant 1 (n=4 mice per group).
ND=not detected (Ct≥35)

GENETICALLY MODIFIED T CELL RECEPTOR MICE

CROSS-REFERENCE TO RELATED APPLICATIONS

This application is a continuation application of U.S. application Ser. No. 13/661,342, filed Oct. 26, 2012, which claims the benefit of priority under 35 U.S.C. § 119(e) to U.S. Provisional Application No. 61/552,582, filed Oct. 28, 2011; U.S. Provisional Application No. 61/621,198, filed Apr. 6, 2012; and U.S. Provisional Application No. 61/700,908, filed Sep. 14, 2012, all of which are incorporated by reference herein in their entirety.

FIELD OF THE INVENTION

Present invention relates to a genetically modified non-human animal, e.g., a rodent (e.g., a mouse or a rat), that comprises in its genome human or humanized T Cell Receptor (TCR) variable gene loci (e.g., TCRα and TCRβ variable gene loci and/or TCRδ and TCRγ variable gene loci), and expresses human or humanized TCR polypeptides (e.g., TCRα and TCRβ polypeptides and/or TCRδ and TCRγ polypeptides) from the human or humanized TCR variable gene loci. A non-human animal with human or humanized TCR variable gene loci of the invention comprises unrearranged human TCR variable region gene segments (e.g., V, D, and/or J segments) at endogenous non-human TCR gene loci. The invention also relates to embryos, tissues, and cells (e.g., T cells) that comprise human or humanized TCR variable gene loci and express human or humanized TCR polypeptides. Also provided are methods for making the genetically modified non-human animal comprising human or humanized TCR variable gene loci; and methods of using non-human animals, embryos, tissues, and cells that comprise human or humanized TCR variable gene loci and express human or humanized TCR polypeptides from those loci.

BACKGROUND OF THE INVENTION

In the adaptive immune response, foreign antigens are recognized by receptor molecules on B lymphocytes (e.g., immunoglobulins) and T lymphocytes (e.g., T cell receptors or TCRs). While pathogens in the blood and extracellular space are recognized by antibodies in the course of humoral immune response, destruction of pathogens inside cells is mediated in the course of cellular immune response by T cells.

T cells recognize and attack antigens presented to them in the context of a Major Histocompatibility Complex (MHC) on the cell surface. The antigen recognition is mediated by TCRs expressed on the surface of the T cells. Two main classes of T cells serve this function: cytotoxic T cells, which express a cell-surface protein CD8, and helper T cells, which express a cell-surface protein CD4. Cytotoxic T cells activate signaling cascades that result in direct destruction of the cell presenting the antigen (in the context of MHC I), while helper T cells differentiate into several classes, and their activation (primed by recognition of antigen presented in the context of MHC II) results in macrophage-mediated pathogen destruction and stimulation of antibody production by B cells.

Because of their antigen specificity, antibodies are presently widely studied for their therapeutic potential against numerous human disorders. To generate antibodies capable of neutralizing human targets, while simultaneously avoiding activation of immune responses against such antibodies, scientists have concentrated their efforts on producing human or humanized immunoglobulins. One way of producing humanized antibodies in vivo is by using VELOCIMMUNE® mouse, a humanized mouse comprising (1) unrearranged human immunoglobulin V, D, and J segment repertoire operably linked to each other and a mouse constant region at the endogenous mouse immunoglobulin heavy chain locus and (2) unrearranged human Vκ and Jκ segment repertoire operably linked to each other and a mouse constant κ region at the endogenous mouse immunoglobulin K light chain locus. As such, VELOCIMMUNE® mice provide a rich source of highly diverse rearranged antibody variable domains for use in engineering human antibodies.

Similar to an antibody, a T cell receptor comprises a variable region, encoded by unrearranged loci (α and β loci, or δ and γ loci) comprising V(D)J variable region segments, and this variable region confers upon the T cell its antigen binding specificity. Also similar to an antibody, the TCR specificity for its antigen can be utilized for development of novel therapeutics. Thus, there is a need in the art for non-human animals (e.g., rodents, e.g., rats or mice) that comprise unrearranged human T cell variable region gene segments capable of rearranging to form genes that encode human T cell receptor variable domains, including domains that are cognate with one another, and including domains that specifically bind an antigen of interest. There is also a need for non-human animals that comprise T cell variable region loci that comprise conservative humanizations, including non-human animals that comprise unrearranged human gene segments that can rearrange to form T cell receptor variable region genes that are linked to non-human (endogenous) T cell receptor constant gene sequences. There remains a need for non-human animals that are capable of generating a diverse repertoire of human T cell receptor variable sequences. There is a need for non-human animals that are capable of rearranging most or all functional T cell receptor variable region segments, in response to an antigen of interest, to form T cell receptor polypeptides that comprise fully human variable domains.

SUMMARY OF THE INVENTION

Non-human animals, e.g., rodents, comprising non-human cells that express humanized molecules that function in the cellular immune response are provided. Non-human animals that comprise unrearranged TCR variable gene loci are also provided. In vivo and in vitro systems are provided that comprise humanized rodent cells, wherein the rodent cells express one or more humanized immune system molecules. Unrearranged humanized TCR rodent loci that encode humanized TCR proteins are also provided.

In one aspect, provided herein is a genetically modified non-human animal (e.g., a rodent, e.g., a mouse or a rat) that comprises in its genome (a) an unrearranged TCRα variable gene locus comprising at least one human Vα segment and at least one human Jα segment, operably linked to a non-human (e.g., a rodent, e.g., a mouse or a rat) TCRα constant gene sequence, and/or (b) an unrearranged TCRβ variable gene locus comprising at least one human Vβ segment, at least one human Dβ segment, and at least one human Jβ segment, operably linked to a non-human (e.g., a rodent, e.g., a mouse or a rat) TCRβ constant gene sequence.

In one embodiment, the unrearranged TCRα variable gene locus replaces endogenous non-human (e.g., rodent)

TCRα variable gene locus at an endogenous TCRα variable gene locus. In one embodiment, the unrearranged TCRβ variable gene locus replaces the endogenous non-human (e.g., rodent) TCRβ variable gene locus at an endogenous TCRδ variable gene locus. In one embodiment, the endogenous non-human (e.g., rodent) Vα and Jα segments are incapable of rearranging to form a rearranged Vα/Jα sequence. In one embodiment, the endogenous non-human (e.g., rodent) Vβ, Dβ, and Jβ segments are incapable of rearranging to form a rearranged Vβ/Dβ/Jβ sequence. In one embodiment, the non-human animal comprises a deletion such that the genome of the animal does not comprise a functional Vα and functional Jα segment. In one embodiment, the non-human animal comprises a deletion such that the genome of the animal does not comprise a functional endogenous Vβ, a functional endogenous Dβ, and a functional endogenous Jβ segment. In one embodiment, the animal comprises a deletion of all functional endogenous Vα and Jα segments. In one embodiment, the rodent comprises a deletion of all functional endogenous Vβ, Dβ, and Jβ segments. In some embodiments, the human Vα and Jα segments rearrange to form a rearranged Vα/Jα sequence. In some embodiments, the human Vβ, Dβ, and Jβ segments rearrange to form a rearranged Vβ/Dβ/Jβ sequence. Thus, in various embodiments, the non-human animal (e.g., rodent) expresses a T cell receptor comprising a human variable region and a non-human (e.g., rodent) constant region on a surface of a T cell.

In some aspects, T cells of the non-human animal undergo T cell development in the thymus to produce CD4 and CD8 single positive T cells. In some aspects, the non-human animal comprises a normal ratio of splenic CD3+ T cells to total splenocytes. In various embodiments, the non-human animal generates a population of central and effector memory T cells in the periphery.

In one embodiment, the unrearranged TCRα variable gene locus in the non-human animal described herein comprises 61 human Jα segments and 8 human Vα segments. In another embodiment, the unrearranged TCRα variable gene locus in the non-human animal comprises a complete repertoire of human Jα segments and a complete repertoire of human Vα segments.

In one embodiment, the unrearranged TCRδ variable gene locus in the non-human animal described herein comprises 14 human Jβ segments, 2 human Dβ segments, and 14 human Vβ segments. In another embodiment, the unrearranged TCRβ variable gene locus in the non-human animal comprises a complete repertoire of human Jβ segments, a complete repertoire of human Dβ segments, and a complete repertoire of human Vβ segments.

In an additional embodiment, the non-human animal described herein (e.g., a rodent) further comprises nucleotide sequences of human TCRδ variable segments at a humanized TCRα locus. In one embodiment, the non-human animal (e.g., rodent) further comprises at least one human Vδ, Dδ, and Jδ segments, e.g., a complete repertoire of human Vδ, Dδ, and Jδ segments at the humanized TCRα locus.

In one embodiment, the non-human animal retains an endogenous non-human TCRα and/or TCRβ locus, wherein the locus is a non-functional locus.

In one embodiment, the non-human animal is a rodent. In one embodiment, the rodent is selected from a mouse and a rat. In one embodiment, the rodent is a mouse.

In one aspect, the invention provides a genetically modified mouse comprising in its genome (a) an unrearranged TCRα variable gene locus comprising a repertoire of human Jα segments and a repertoire of human Vα segments, operably linked to a non-human (e.g., mouse or rat) TCRα constant gene sequence, and/or (b) an unrearranged TCRβ variable gene locus comprising a repertoire of human Jβ segments, a repertoire of human Dβ segments, and a repertoire of human Vβ segments, operably linked to a non-human (e.g., a mouse or rat) TCRβ constant gene sequence. In one embodiment, the mouse comprises a complete repertoire of human Vα segments. In one embodiment, the mouse comprises a complete repertoire of human Vβ segments. In one embodiment, the mouse comprises a complete repertoire of human Vα segments and human Jα segments. In one embodiment, the mouse comprises a complete repertoire of human Vα segments and human Vβ segments. In one embodiment, the mouse comprises a complete repertoire of human Vα, human Jα, human Vβ, human Dβ, and human Jβ segments.

In one embodiment, the mouse comprises at least one endogenous mouse Vα and at least one endogenous mouse Jα segment, wherein the endogenous segments are incapable of rearranging to form a rearranged Vα/Jα sequence, and also comprises at least one endogenous mouse Vβ, at least one endogenous mouse Dβ, and at least one endogenous mouse Jβ segment, wherein the endogenous segments are incapable of rearranging to form a rearranged Vβ/Dβ/Jβ sequence.

In one embodiment, the unrearranged TCRα variable gene locus that comprises human TCRα variable region segments replaces mouse TCRα variable genes at the endogenous mouse TCRα variable locus, and the unrearranged TCRβ variable gene locus that comprises human TCRβ variable region segments replaces mouse TCRβ variable genes at the endogenous mouse TCRβ variable locus.

In one embodiment, the human Vα and Jα segments rearrange to form a rearranged human Vα/Jα sequence, and the human Vβ, Dβ, and Jβ segments rearrange to form a rearranged human Vβ/Dβ/Jβ sequence. In one embodiment, the rearranged human Vα/Jα sequence is operably linked to a mouse TCRα constant region sequence. In one embodiment, the rearranged human Vβ/Dβ/Jβ sequence is operably linked to a mouse TCRβ constant region sequence. Thus, in various embodiments, the mouse expresses a T cell receptor on the surface of a T cell, wherein the T cell receptor comprises a human variable region and a mouse constant region.

In one embodiment, the mouse further comprises a repertoire of human TCRδ variable region segments (e.g., human Vδ, Jδ, and Dδ segments) at a humanized TCRα locus. In one embodiment, the repertoire of human TCRδ variable region segments is a complete human TCRδ variable region segment repertoire. In one embodiment, the human TCRδ variable region segments are at the endogenous TCRα locus. In one embodiment, the human TCRδ variable region segments replace endogenous mouse TCRδ variable region segments.

In one embodiment, the genetically modified mouse expresses a T cell receptor comprising a human variable region and a mouse constant region on a surface of a T cell. In one aspect, the T cells of the mouse undergo thymic T cell development to produce CD4 and CD8 single positive T cells. In one aspect, the mouse comprises a normal ratio of splenic CD3+ T cells to total splenocytes; in one aspect, the mouse generates a population of central and effector memory T cells to an antigen of interest.

Also provided are methods for making genetically modified non-human animals (e.g., rodents, e.g., mice or rats) described herein.

In one aspect, a method for making a humanized rodent (e.g., a mouse or rat) is provided, comprising replacing rodent TCRα and TCRβ variable region segments, but not rodent constant genes, with human unrearranged TCRα and TCRβ variable region segments, at endogenous rodent TCR loci. In one embodiment, the method comprises replacing rodent TCRα variable region segments (Vα and/or Jα) with human TCRα variable region segments (Vα and/or Jα), wherein the TCRα variable region segments are operably linked to a non-human TCR constant region gene to form a humanized TCRα locus; and replacing rodent TCRβ variable region segments (Vβ and/or Dβ and/or Jβ) with human TCRβ variable region segments (Vβ and/or Dβ and/or Jβ), wherein the TCRβ variable region segments are operably linked to a non-human TCR constant region gene to form a humanized TCRβ locus. In one embodiment, the humanized rodent is a mouse and the germline of the mouse comprises the human TCRα variable region segments operably linked to an endogenous mouse TCRα constant sequence at an endogenous TCRα locus; and the germline of the mouse comprises the human TCRβ variable region segments operably linked to an endogenous mouse TCRβ constant sequence at an endogenous TCRβ locus.

In one embodiment, provided herein is a method for making a genetically modified non-human animal (e.g., rodent, e.g., mouse or rat) that expresses a T cell receptor comprising a human or humanized variable region and a non-human (e.g., rodent) constant region on a surface of a T cell comprising: replacing in a first non-human animal an endogenous non-human TCRα variable gene locus with an unrearranged humanized TCRα variable gene locus comprising at least one human Vα segment and at least one human Jα segment, wherein the humanized TCRα variable gene locus is operably linked to endogenous non-human TCRα constant region; replacing in a second non-human animal an endogenous non-human TCRα variable gene locus with an unrearranged humanized TCRβ variable gene locus comprising at least one human Vβ segment, at least one human Dβ segment, and at least one human Jβ segment, wherein the humanized TCRβ variable gene locus is operably linked to endogenous TCRβ constant region; and breeding the first and the second non-human animal to obtain a non-human animal that expresses a T cell receptor comprising a human or humanized variable region and a non-human constant region.

In one embodiment of the method, the endogenous non-human (e.g., rodent) Vα and Jα segments are incapable of rearranging to form a rearranged Vα/Jα sequence and the endogenous non-human (e.g., rodent) Vβ, Dβ, and Jβ segments are incapable of rearranging to form a rearranged Vβ/Dβ/Jβ sequence. In one embodiment of the method, the human Vα and Jα segments rearrange to form a rearranged Vα/Jα sequence and the human Vβ, Dβ, and Jβ segments rearrange to form a rearranged Vβ/Dβ/Jβ sequence. In one embodiment of the method, the unrearranged humanized TCRα variable gene locus comprises 61 human Jα segments and 8 human Vα segments, and the unrearranged humanized TCRβ variable gene locus comprises 14 human Vβ segments, 2 human Dβ segments, and 14 human Jβ segments. In another embodiment of the method, the unrearranged humanized TCRα variable gene locus comprises a complete repertoire of human Jα segments and a complete repertoire of human Vα segments, and the unrearranged humanized TCRβ variable gene locus comprises a complete repertoire of human Vβ segments, a complete repertoire of human Dβ segments, and a complete repertoire of human Jβ segments.

In one aspect of the method, the T cells of the non-human animal (e.g., rodent) undergo thymic T cell development to produce CD4 and CD8 single positive T cells. In one aspect, the non-human animal (e.g., the rodent) comprises a normal ratio of splenic CD3+ T cells to total splenocytes. In one aspect, the non-human animal (e.g., rodent) generates a population of central and effector memory T cells to an antigen of interest.

In some embodiments, the replacement of the endogenous non-human TCRα variable gene locus described herein is made in a single ES cell, and the single ES cell is introduced into a non-human (e.g., a rodent, e.g., a mouse or rat) embryo to make a genetically modified non-human animal (i.e., the first non-human animal, e.g., the first rodent); and the replacement of the endogenous non-human TCRβ variable gene locus described herein is made in a single ES cell, and the single ES cell is introduced into a non-human (e.g., a rodent, e.g., a mouse or rat) embryo to make a genetically modified non-human animal (i.e., the second non-human animal, e.g., the second rodent). In one embodiment, the first rodent and the second rodent are bred to form a progeny, wherein the progeny comprises in its germline a humanized TCRα variable locus and a humanized TCRβ variable locus.

In one embodiment of the method, the non-human animal is a rodent, e.g., a mouse. Thus, the present invention also provides a method for making a genetically modified mouse.

Also provided herein are cells, e.g., isolated T cells (e.g., cytotoxic T cells, helper T cells, memory T cells, etc.), derived from the non-human animals (e.g., rodents, e.g., mice or rats) described herein. Tissues and embryos derived from the non-human animals described herein are also provided.

In one aspect, a method for making a human TCR variable domain is provided, comprising genetically modifying a rodent as described herein to comprise a humanized TCRα locus and/or a humanized TCRβ locus, maintaining the rodent under conditions sufficient to form a T cell, wherein the T cell expresses a human TCRα and/or a human TCRβ variable domain.

In one aspect, a method for making a nucleic acid sequence encoding a human TCR variable domain that binds an epitope of interest is provided, comprising exposing a non-human animal as described herein to an epitope of interest, maintaining the non-human animal under conditions sufficient for the animal to present the epitope of interest to a humanized TCR of the animal, and identifying a nucleic acid of the animal that encodes a human TCR variable domain polypeptide that binds the epitope of interest.

In one aspect, use of a non-human animal as described herein is provided for making a humanized TCR receptor. In one aspect, use of a non-human animal as described herein is provided for making a human TCR variable domain. In one aspect, use of a non-human animal as described herein is provided for making a nucleic acid sequence encoding a human TCR variable domain.

In one aspect, use of nucleic acid sequence encoding a human TCR variable domain or fragment thereof to make an antigen-binding protein is provided. In one embodiment, the antigen-binding protein comprises a TCR variable domain comprising a human TCRα and/or human TCRβ variable domain that binds an antigen of interest.

In one aspect, use of a non-human as described herein is provided for making a non-human cell that expresses on its surface a humanized T cell receptor.

In one aspect, a humanized T cell receptor from a non-human animal as described herein is provided.

In one aspect, a nucleic acid sequence encoding a human TCR variable domain or fragment thereof, made in a non-human animal as described herein, is provided.

Any of the embodiments and aspects described herein can be used in conjunction with one another, unless otherwise indicated or apparent from the context. Other embodiments will become apparent to those skilled in the art from a review of the ensuing detailed description. The following detailed description includes exemplary representations of various embodiments of the invention, which are not restrictive of the invention as claimed. The accompanying figures constitute a part of this specification and, together with the description, serve only to illustrate embodiments and not to limit the invention.

BRIEF DESCRIPTION OF THE DRAWINGS

FIG. 1 depicts interaction in a mouse between a TCR molecule and an MHC molecule: the left panel shows a mouse T cell (top) from a humanized TCR mouse comprising a T cell receptor with human variable TCR domains and mouse constant TCR domains, which recognizes an antigen (grey ball) presented through an MHC class I by an antigen presenting cell (bottom); the right panel shows the same for an MHC class II. The MHC I and MHC II complexes are shown together with their respective co-receptors, CD8 and CD4. Mouse regions are in black and human regions are in white.

FIG. 4A depicts deletion of the mouse TCRα V and J segments; FIG. 4B depicts strategy for insertion of 2V and 61 J human segments into the deleted mouse TCRα locus; FIG. 4C depicts strategy for insertion of additional human V segments, resulting in a total of 8V and 61J human segments; FIG. 4D depicts strategy for insertion of additional human V segments, resulting in a total of 23V and 61J human segments; FIG. 4E depicts strategy for insertion of additional human V segments resulting in 35V and 61J human segments; FIG. 4F depicts strategy for insertion of additional human segments resulting in 48V and 61J human segments; and FIG. 4G depicts strategy for insertion of additional human segments resulting in 54V and 61J human segments. MAID refers to modified allele ID number.

FIG. 8A depicts the strategy for deletion of the mouse TCRβ V segments; FIG. 8B depicts the strategy for insertion of 14V segments into the deleted TCRβ locus; FIG. 8C depicts the strategy for insertion of 2D and 14J segments into TCRβ locus (i), followed by deletion of the loxP site (ii), resulting in 14V, 2D and 14J human segments; FIG. 8D depicts the strategy for inserting additional human V segments resulting in 40V, 2D and 14J human segments; and FIG. 8E depicts the strategy for insertion of additional human V segments resulting in the 66V, 2D and 14J human segments; FIG. 8F depicts replacement of the mouse V segment downstream of a mouse enhancer, resulting in 67V, 2D and 14J human segments. In this particular embodiment, one mouse V segment is retained 5' of the mouse trypsinogen genes.

FIG. 15 are tables summarizing expression (determined by FACS analysis using variable segment-specific antibodies) of various human TCRβ V segments in the splenic CD8+ T cells (FIG. 15A) or CD4+ T cells (FIG. 15B) of WT, hTCRβ (1716 HO) or hTCRα/β (1716 HO 1767 HO) mice. Data presented as Mean±SD (n=4 mice per group)

FIG. 16A represents analysis of mRNA expression of human TCRβ variable segment (hTRBV) 18, 19, 20, and 24; and FIG. 16B represents analysis of mRNA expression of hTRBV 25, 27, 28, and 29.

DETAILED DESCRIPTION OF THE INVENTION

Definitions

Figure 2:
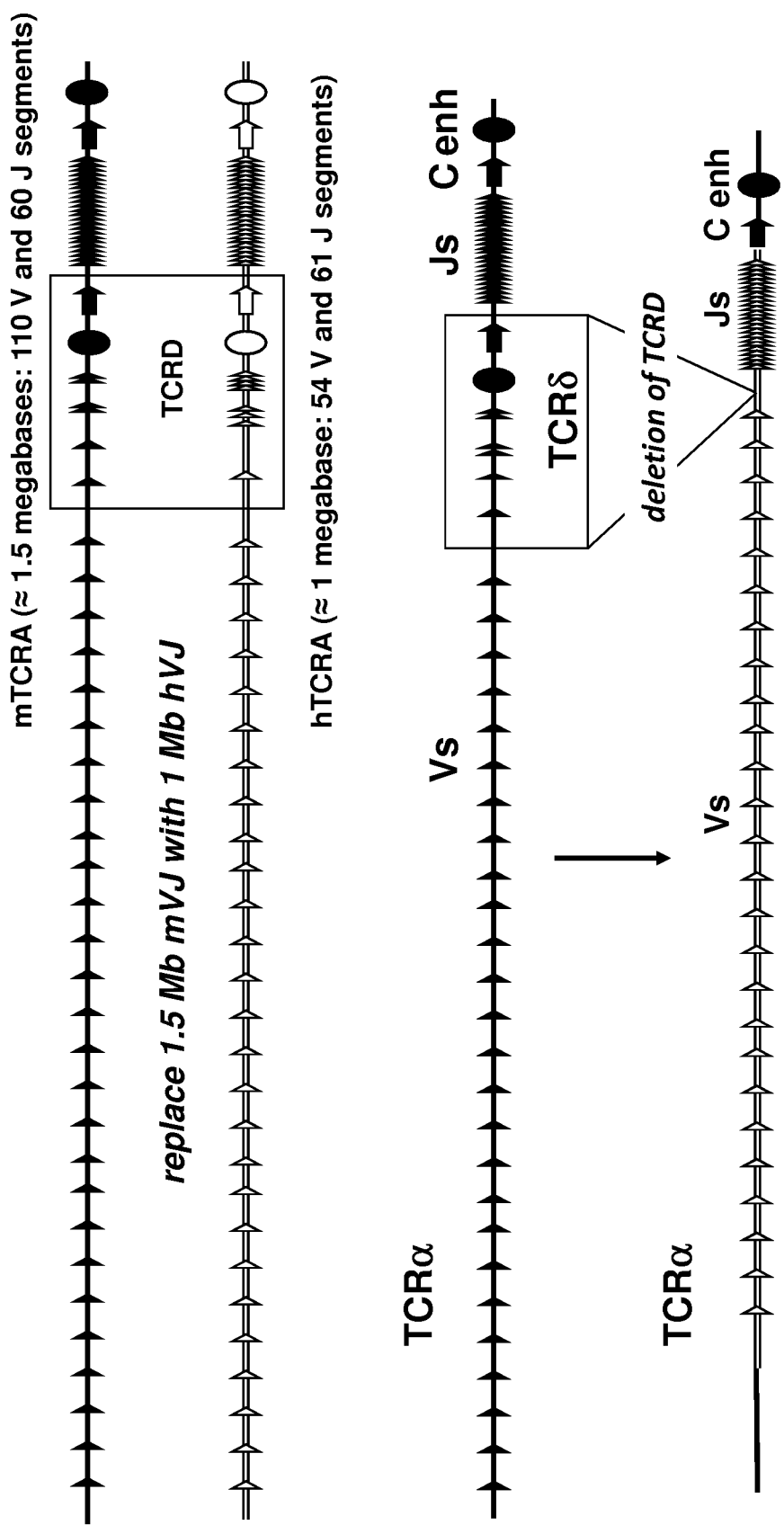
FIG. 2 depicts (not to scale) the general organization of a mouse (top panel, first locus) and human (top panel, second locus) TCRα locus. The bottom panel illustrates a strategy for replacing TCRα variable region segments in a mouse (closed symbols) with human TCRα variable region segments (open symbols) at the endogenous mouse locus on chromosome 14; a humanized TCRα locus having human Vα and Jα segments is shown with a mouse constant region and a mouse enhancer; in the embodiment shown, the TCRδ locus is deleted in the course of humanization.

The present invention provides genetically modified non-human animals, e.g., rodents, e.g., mice or rats, that express humanized T cell receptors. The present invention also relates to genetically modified non-human animals that comprise in their germline unrearranged T cell receptor variable gene loci. Also provided are embryos, cells, and tissues comprising the same; methods of making the same; as well as methods of using the same. Unless defined otherwise, all terms and phrases used herein include the meanings that the terms and phrases have attained in the art, unless the contrary is clearly indicated or clearly apparent from the context in which the term or phrase is used.

The term "conservative," when used to describe a conservative amino acid substitution, includes substitution of an amino acid residue by another amino acid residue having a side chain R group with similar chemical properties (e.g., charge or hydrophobicity). Conservative amino acid substitutions may be achieved by modifying a nucleotide sequence so as to introduce a nucleotide change that will encode the conservative substitution. In general, a conservative amino acid substitution will not substantially change the functional properties of interest of a protein, for example, the ability of a T cell to recognize a peptide presented by an MHC molecule. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet et al. ((1992) Exhaustive Matching of the Entire Protein Sequence Database, Science 256: 1443-45), hereby incorporated by reference. In some embodiments, the substitution is a moderately conservative substitution wherein the substitution has a nonnegative value in the PAM250 log-likelihood matrix.

Thus, encompassed by the invention is a genetically modified non-human animal expressing humanized TCR α and β polypeptides (and/or humanized TCRδ and TCRγ polypeptides) comprising conservative amino acid substitutions in the amino acid sequence described herein.

One skilled in the art would understand that in addition to the nucleic acid residues encoding humanized TCR α and β polypeptides described herein, due to the degeneracy of the genetic code, other nucleic acids may encode the polypeptides of the invention. Therefore, in addition to a genetically modified non-human animal that comprises in its genome nucleotide sequences encoding humanized TCR polypeptides described herein, a non-human animal that comprises in its genome nucleotide sequences that differ from those described herein due to the degeneracy of the genetic code are also provided.

The term "identity" when used in connection with sequence includes identity as determined by a number of different algorithms known in the art that can be used to measure nucleotide and/or amino acid sequence identity. In some embodiments described herein, identities are determined using a ClustalW v. 1.83 (slow) alignment employing an open gap penalty of 10.0, an extend gap penalty of 0.1, and using a Gonnet similarity matrix (MacVector™ 10.0.2, MacVector Inc., 2008). The length of the sequences compared with respect to identity of sequences will depend upon the particular sequences. In various embodiments, identity is determined by comparing the sequence of a mature protein from its N-terminal to its C-terminal. In various embodiments, when comparing a chimeric human/non-human sequence to a human sequence, the human portion of the chimeric human/non-human sequence (but not the non-human portion) is used in making a comparison for the purpose of ascertaining a level of identity between a human sequence and a human portion of a chimeric human/non-human sequence (e.g., comparing a human ectodomain of a chimeric human/mouse protein to a human ectodomain of a human protein).

The terms "homology" or "homologous" in reference to sequences, e.g., nucleotide or amino acid sequences, means two sequences which, upon optimal alignment and comparison, are identical in at least about 75% of nucleotides or amino acids, at least about 80% of nucleotides or amino acids, at least about 90-95% nucleotides or amino acids, e.g., greater than 97% nucleotides or amino acids. One skilled in the art would understand that, for optimal gene targeting, the targeting construct should contain arms homologous to endogenous DNA sequences (i.e., "homology arms"); thus, homologous recombination can occur between the targeting construct and the targeted endogenous sequence.

The term "operably linked" refers to a juxtaposition wherein the components so described are in a relationship permitting them to function in their intended manner. As such, a nucleic acid sequence encoding a protein may be operably linked to regulatory sequences (e.g., promoter, enhancer, silencer sequence, etc.) so as to retain proper transcriptional regulation. In addition, various portions of the humanized protein of the invention may be operably linked to retain proper folding, processing, targeting, expression, and other functional properties of the protein in the cell. Unless stated otherwise, various domains of the humanized protein of the invention are operably linked to each other.

The term "replacement" in reference to gene replacement refers to placing exogenous genetic material at an endogenous genetic locus, thereby replacing all or a portion of the endogenous gene with an orthologous or homologous nucleic acid sequence. In one instance, an endogenous non-human gene or fragment thereof is replaced with a corresponding human gene or fragment thereof. A corresponding human gene or fragment thereof is a human gene or fragment that is an ortholog of, a homolog of, or is substantially identical or the same in structure and/or function, as the endogenous non-human gene or fragment thereof that is replaced. As demonstrated in the Examples below, nucleotide sequences of endogenous non-human TCR α and β variable gene loci were replaced by nucleotide sequences corresponding to human TCR α and β variable gene loci.

"Functional" as used herein, e.g., in reference to a functional protein, refers to a protein that retains at least one biological activity normally associated with the native protein. For example, in some embodiments of the invention, a replacement at an endogenous locus (e.g., replacement at endogenous non-human TCRα, TCRβ, TCRδ and/or TCRγ variable gene loci) results in a locus that fails to express a functional endogenous protein.

TCR locus or TCR gene locus (e.g., TCRα locus or TCRβ locus), as used herein, refer to the genomic DNA comprising the TCR coding region, including the entire TCR coding region, including unrearranged V(D)J sequences, enhancer, sequence, constant sequence(s), and any upstream or downstream (UTR, regulatory regions, etc.), or intervening DNA sequence (introns, etc.). TCR variable locus or TCR variable gene locus (e.g., TCRα variable gene locus or TCRβ variable gene locus), refers to genomic DNA comprising the region that includes TCR variable region segments (V(D)J region) but excludes TCR constant sequences and, in various embodiments, enhancer sequences. Other sequences may be included in the TCR variable gene locus for the purposes of genetic manipulation (e.g., selection cassettes, restriction sites, etc.), and these are encompassed herein.

Genetically Modified TCR Animals

In various embodiments, the invention generally provides genetically modified non-human animals wherein the non-human animals comprise in the genome unrearranged humanized TCR variable gene loci.

T cells bind epitopes on small antigenic determinants on the surface of antigen-presenting cells that are associated with a major histocompatibility complex (MHC; in mice) or human leukocyte antigen (HLA; in humans) complex. T cells bind these epitopes through a T cell receptor (TCR) complex on the surface of the T cell. T cell receptors are heterodimeric structures composed of two types of chains: an α (alpha) and β (beta) chain, or a γ (gamma) and δ (delta) chain. The α chain is encoded by the nucleic acid sequence located within the α locus (on human or mouse chromosome 14), which also encompasses the entire δ locus, and the β chain is encoded by the nucleic acid sequence located within the β locus (on mouse chromosome 6 or human chromosome 7). The majority of T cells have an αβ TCR; while a minority of T cells bear a γδ TCR. Interactions of TCRs with MHC class I (presenting to CD8+ T cells) and MHC class II (presenting to CD4+ T cells) molecules are shown in FIG. 1 (closed symbols represent non-human sequences; open symbols represent human sequences, showing one particular embodiment of the TCR protein of the present invention).

T cell receptor α and β polypeptides (and similarly γ and δ polypeptides) are linked to each other via a disulfide bond. Each of the two polypeptides that make up the TCR contains an extracellular domain comprising constant and variable regions, a transmembrane domain, and a cytoplasmic tail (the transmembrane domain and the cytoplasmic tail also being a part of the constant region). The variable region of the TCR determines its antigen specificity, and similar to immunoglobulins, comprises 3 complementary determining regions (CDRs). Also similar to immunoglobulin genes, T cell receptor variable gene loci (e.g., TCRα and TCRβ loci) contain a number of unrearranged V(D)J segments (variable (V), joining (J), and in TCRβ and δ, diversity (D) segments). During T cell development in the thymus, TCRα variable gene locus undergoes rearrangement, such that the resultant TCR α chain is encoded by a specific combination of VJ segments (Vα/Jα sequence); and TCRβ variable gene locus undergoes rearrangement, such that the resultant TCR β chain is encoded by a specific combination of VDJ segments (Vβ/Dβ/Jβ sequence).

Interactions with thymic stroma trigger thymocytes to undergo several developmental stages, characterized by expression of various cell surface markers. A summary of characteristic cell surface markers at various developmental stages in the thymus is presented in Table 1. Rearrangement at the TCRβ variable gene locus begins at the DN2 stage and ends during the DN4 stage, while rearrangement of the TCRα variable gene locus occurs at the DP stage. After the completion of TCRβ locus rearrangement, the cells express TCRβ chain at the cell surface together with the surrogate a chain, pTα. See, Janeway's Immunobiology, Chapter 7, supra.

TABLE 1

Developmental Stages of T cells in the Thymus

| | Developmental Stage | | | | |
|---|---|---|---|---|---|
| | DN1 | DN2 | DN3 | DN4 | DP | SP |
| Marker(s) | CD44+/ CD25− | CD44+/ CD25+ | CD44$^{low}$/ CD25+ | CD44−/ CD25− | CD4+/ CD8+ | CD4+ or CD8+ |

Naive CD4+ and CD8+ T cells exit the thymus and enter the peripheral lymphoid organs (e.g., spleen) where they are exposed to antigens and are activated to clonally expand and differentiate into a number of effector T cells (Teff), e.g., cytotoxic T cells, $T_{REG}$ cells, $T_H17$ cells, $T_H1$ cells, $T_H2$ cells, etc. Subsequent to infection, a number of T cells persist as memory T cells, and are classified as either central memory T cells (Tcm) or effector memory T cells (Tem). Sallusto et al. (1999) Two subsets of memory T lymphocytes with distinct homing potentials and effector functions, Nature 401:708-12 and Commentary by Mackay (1999) Dual personality of memory T cells, Nature 401:659-60. Sallusto and colleagues proposed that, after initial infection, Tem cells represent a readily available pool of antigen-primed memory T cells in the peripheral tissues with effector functions, while Tcm cells represent antigen-primed memory T cells in the peripheral lymphoid organs that upon secondary challenge can become new effector T cells. While all memory T cells express CD45RO isoform of CD45 (naïve T cells express CD45RA isoform), Tcm are characterized by expression of L-selectin (also known as CD62L) and CCR7+, which are important for binding to and signaling in the peripheral lymphoid organs and lymph nodes. Id. Thus, all T cells found in the peripheral lymphoid organs (e.g., naïve T cells, Tcm cells, etc.) express CD62L. In addition to CD45RO, all memory T cells are known to express a number of different cell surface markers, e.g., CD44. For summary of various cell surface markers on T cells, see Janeway's Immunobiology, Chapter 10, supra.

While TCR variable domain functions primarily in antigen recognition, the extracellular portion of the constant domain, as well as transmembrane, and cytoplasmic domains of the TCR also serve important functions. A complete TCR receptor complex requires more than the α and β or γ and δ polypeptides; additional molecules required include CD3γ, CD3δ, and CD3ε, as well as the ξ chain homodimer (t). At the completion of TCRβ rearrangement, when the cells express TCRβ/pTα, this pre-TCR complex exists together with CD3 on the cell surface. TCRα (or pTα) on the cell surface has two basic residues in its transmembrane domain, one of which recruits a CD3γε heterodimer, and another recruits via their respective acidic residues. TCRβ has an additional basic residue in its transmembrane domain that is believed to recruit CD386 heterodimer. See, e.g., Kuhns et al. (2006) Deconstructing the Form and Function of the TCR/CD3 Complex, Immunity 24:133-39; Wucherpfennig et al. (2009) Structural Biology of the T-cell Receptor: Insights into Receptor Assembly, Ligand Recognition, and Initiation of Signaling, Cold Spring Harb. Perspect. Biol. 2:a005140. The assembled complex, comprising TCRαβ heterodimer, CD3γε, CD38Σ, and ξξ, is expressed on the T cell surface. The polar residues in the transmembrane domain have been suggested to serve as quality control for exiting endoplasmic reticulum; it has been demonstrated that in the absence of CD3 subunits, TCR chains are retained in the ER and targeted for degradation. See, e.g., Call and Wucherpfennig (2005) The T Cell Receptor: Critical Role of the Membrane Environment in Receptor Assembly and Function, Annu. Rev. Immunol. 23:101-25.

CD3 and ξ chains of the assembled complex provide components for TCR signaling as TCRαβ heterodimer (or TCRγ 6 heterodimer) by itself lacks signal transducing activity. The CD3 chains possess one Immune-Receptor-Tyrosine-based-Activation-Motif (ITAM) each, while the ξ chain contains three tandem ITAMs. ITAMs contain tyrosine residues capable of being phosphorylated by associated kinases. Thus, the assembled TCR-CD3 complex contains 10 ITAM motifs. See, e.g., Love and Hayes (2010) ITAM-Mediated Signaling by the T-Cell Antigen Receptor, Cold Spring Harb. Perspect. Biol. 2:e002485. Following TCR engagement, ITAM motifs are phosphorylated by Src family tyrosine kinases, Lck and Fyn, which initiates a signaling cascade, resulting in Ras activation, calcium mobilization, actin cytoskeleton rearrangements, and activation of transcription factors, all ultimately leading to T cell differentiation, proliferation, and effector actions. Id., see also, Janeway's Immunobiology, 7$^{th}$ Ed., Murphy et al. eds., Garland Science, 2008; both incorporated herein by reference.

Additionally, TCRβ transmembrane and cytoplasmic domains are thought to have a role in mitochondrial targeting and induction of apoptosis; in fact, naturally occurring N-terminally truncated TCRβ molecules exist in thymocytes. Shani et al. (2009) Incomplete T-cell receptor—β peptides target the mitochondrion and induce apoptosis, Blood 113:3530-41. Thus, several important functions are served by the TCR constant region (which, in various embodiments, comprises a portion of extracellular as well as transmembrane and cytoplasmic domains); and in various embodiments the structure of this region should be taken into consideration when designing humanized TCRs or genetically modified non-human animals expressing the same.

Mice transgenic for rearranged T cell receptor sequences are known in the art. The present invention relates to genetically modified non-human animals (e.g., rodents, e.g., rats, mice) that comprise unrearranged human or humanized T cell variable gene loci that are capable of rearranging to form nucleic acid sequences that encode human T cell receptor variable domains, including animals that comprise T cells that comprise rearranged human variable domains and non-human (e.g., mouse or rat) constant regions. The present invention also provides non-human animals (e.g., rodents, e.g., rats, mice) that are capable of generating a diverse repertoire of human T cell receptor variable region sequences; thus, the present invention provides non-human animals that express TCRs with fully human variable domains in response to an antigen of interest and that bind an epitope of the antigen of interest. In some embodiments, provided are non-human animals that generate a diverse T cell receptor repertoire capable of reacting with various antigens, including but not limited to antigens presented by APCs.

In one embodiment, the invention provides genetically modified non-human animals (e.g., rodents, e.g., rats, mice) that comprise in their genome unrearranged human TCR variable region segments (V(D)J segments), wherein the unrearranged human TCR variable region segments replace, at an endogenous non-human (e.g., rodent) TCR variable gene locus (e.g., TCRα,β, δ, and/or γ variable gene locus), endogenous non-human TCR variable region segments. In one embodiment, unrearranged human TCR variable gene locus replaces endogenous non-human TCR variable gene locus.

In another embodiment, the invention provides genetically modified non-human animals (e.g., rodents, e.g., rats, mice) that comprise in their genome unrearranged human TCR variable region segments (V(D)J segments), wherein the unrearranged human TCR variable region segments are operably linked to a non-human TCR constant region gene sequence resulting in a humanized TCR locus, wherein the humanized TCR locus is at a site in the genome other than the endogenous non-human TCR locus. Thus, in one embodiment, a non-human animal (e.g., rodent, e.g., mouse, rat) comprising a transgene that comprises unrearranged human TCR variable region segments operably linked to non-human TCR constant region sequence is also provided.

In one aspect, the genetically modified non-human animals of the invention comprise in their genome human TCR variable region segments, while retaining non-human (e.g., rodent, e.g., mouse, rat) TCR constant gene segments. In various embodiments, constant regions include transmembrane domain and the cytoplasmic tail of the TCR. Thus, in various embodiments of the present invention, the genetically modified non-human animals retain endogenous non-human TCR transmembrane domain and cytoplasmic tail. In other embodiments, non-human animals comprise non-human non-endogenous TCR constant gene sequences, e.g., non-human non-endogenous TCR transmembrane domain and cytoplasmic tail. As indicated above, the constant region of the TCR participates in a signaling cascade initiated during antigen-primed T cell activation; thus, endogenous TCR constant region interacts with a variety of non-human anchor and signaling proteins in the T cell. Thus, in one aspect, the genetically modified non-human animals of the invention express humanized T cell receptors that retain the ability to recruit a variety of endogenous non-human anchor or signaling molecules, e.g., CD3 molecules (e.g., CD3γ, CD3δ, CD3ε), the chain, Lck, Fyn, ZAP-70, etc. A nonlimiting list of molecules that are recruited to the TCR complex is described in Janeway's Immunobiology, supra. In addition, similar to VELOCIMMUNE® mice, which exhibit normal B cell development and normal clonal selection processes believed to be due at least in part to the placement of variable regions at the endogenous mouse loci and the maintenance of mouse constant domains, in one aspect, the non-human animals of the present invention exhibit normal T cell development and T cell differentiation processes.

In some embodiments, a non-human animal is provided that comprises in its genome unrearranged human TCRα variable region segments, wherein the unrearranged human TCRα variable region segments are operably linked to a non-human TCRα constant region gene sequence resulting in a humanized TCRα locus. In one embodiment, the humanized TCRα locus is at a site in the genome other than the endogenous non-human TCRα locus. In another embodiment, the unrearranged human TCRα variable region segments replace endogenous non-human TCRα variable region segments while retaining endogenous non-human TCRα constant region. In one embodiment, the unrearranged human TCRα variable gene locus replaces endogenous non-human TCRα variable gene locus. In some embodiments, the animal retains endogenous non-human TCRβ variable region and constant region gene sequences. Thus, the animal expresses a TCR that comprises a chimeric human/non-human (i.e., humanized) TCRα chain and a non-human TCRβ chain.

In other embodiments, a non-human animal is provided that comprises in its genome unrearranged human TCRβ variable region segments, wherein the unrearranged human TCRβ variable region segments are operably linked to a non-human TCR constant region gene sequence resulting in a humanized TCRβ locus. In one embodiment, the humanized TCRβ locus is at a site in the genome other than the endogenous non-human TCRβ locus. In another embodiment, the unrearranged human TCRβ variable region segments replace endogenous non-human TCRβ variable region segments while retaining endogenous non-human TCRβ constant region. In one embodiment, the unrearranged human TCRβ variable gene locus replaces endogenous non-human TCRβ variable gene locus. In some embodiments, the animal retains endogenous non-human TCRα variable region and constant region gene sequences. Thus, the animal expresses a TCR that comprises a chimeric human/non-human (i.e., humanized) TCRβ chain and a non-human TCRα chain.

In some specific embodiments, the invention provides a genetically modified non-human animal (e.g., rodent, e.g., mouse or rat) that comprises in its genome (a) an unrearranged T cell receptor (TCR) α variable gene locus comprising at least one human Vα segment and at least one human Jα segment, operably linked to an endogenous non-human (e.g., rodent, e.g., mouse or rat) TCRα constant gene sequences, and/or (b) an unrearranged TCRβ variable gene locus comprising at least one human Vβ segment, at least one human Dβ segment, and at least one human Jβ segment, operably linked to an endogenous non-human (e.g., rodent, e.g., mouse or rat) TCRβ constant gene sequence.

In various embodiments of the invention, the unrearranged human or humanized TCR variable gene locus (e.g., TCRα and/or TCRβ variable gene locus gene locus) is comprised in the germline of the non-human animal (e.g., rodent, e.g., mouse or rat). In various embodiments, the replacements of TCR V(D)J segments by unrearranged human TCR V(D)J segments (e.g., Vα and Jα, and/or Vβ and Dβ and Jβ segments) are at an endogenous non-human TCR variable locus (or loci), wherein the unrearranged human V and J and/or V and D and J segments are operably linked to non-human TCR constant region genes.

In some embodiments of the invention, the non-human animal comprises two copies of the unrearranged human or humanized TCRα variable gene locus and/or two copies of the unrearranged human or humanized TCRβ variable gene locus. Thus, the non-human animal is homozygous for one or both unrearranged human or humanized TCRα and TCRβ variable gene locus. In some embodiments of the invention, the non-human animal comprises one copy of the unrearranged human or humanized TCRα variable gene locus and/or one copy of the unrearranged human or humanized TCRβ variable gene locus. Thus, the non-human animal is heterozygous for one or both unrearranged human or humanized TCRα and TCRβ variable gene locus.

In one embodiment, the unrearranged TCRα variable gene locus comprising human variable region segments (e.g., human Vα and Jα segments) is positioned in the non-human genome such that the human variable region segments replace corresponding non-human variable region segments. In one embodiment, the unrearranged TCRα variable gene locus comprising human variable region segments replaces endogenous TCRα variable gene locus. In one aspect, endogenous non-human Vα and Jα segments are incapable of rearranging to form a rearranged Vα/Jα sequence. Thus, in one aspect, the human Vα and Jα segments in the unrearranged TCRα variable gene locus are capable of rearranging to form a rearranged human Vα/Jα sequence.

Similarly, in one embodiment, the unrearranged TCRβ variable gene locus comprising human variable region segments (e.g., human Vβ, Dβ, and Jβ segments) is positioned in the non-human genome such that the human variable region segments replace corresponding non-human variable region segments. In one embodiment, the unrearranged TCRβ variable gene locus comprising human variable region segments replaces endogenous TCRβ variable gene locus. In one aspect, endogenous non-human Vβ, Dβ, and Jβ segments are incapable of rearranging to form a rearranged Vβ/Dβ/Jβ sequence. Thus, in one aspect, the human Vβ, Dβ, and Jβ segments in the unrearranged TCRβ variable gene locus are capable of rearranging to form a rearranged human Vαβ/Dβ/Jβ sequence.

In yet another embodiment, both the unrearranged TCRα and β variable gene loci comprising human variable region segments replace respective endogenous TCRα and β variable gene loci. In one aspect, endogenous non-human Vα and Jα segments are incapable of rearranging to form a rearranged Vα/Jα sequence, and endogenous non-human Vβ, Dβ, and Jβ segments are incapable of rearranging to form a rearranged Vβ/Dβ/Jβ sequence. Thus, in one aspect, the human Vα and Jα segments in the unrearranged TCRα variable gene locus are capable of rearranging to form a rearranged human Vα/Jα sequence and the human Vβ, Dβ, and Jβ segments in the unrearranged TCRβ variable gene locus are capable of rearranging to form a rearranged human Vαβ/Dβ/Jβ sequence.

In some aspects of the invention, the non-human animal comprising a humanized TCRα and/or TCRβ gene locus (comprising an unrearranged TCRα and/or TCRβ variable gene locus) retains an endogenous non-human TCRα and/or TCRβ variable gene locus. In one embodiment, the endogenous non-human TCRα and/or TCRβ variable gene locus is a non-functional locus. In one embodiment, the non-functional locus is an inactivated locus, e.g., an inverted locus (e.g., the coding nucleic acid sequence of the variable gene locus is in inverted orientation with respect to the constant region sequence, such that no successful rearrangements are possible utilizing variable region segments from the inverted locus). In one embodiment, the humanized TCRα and/or TCRβ variable gene locus is positioned between the endogenous non-human TCRα and/or TCRβ variable gene locus and the endogenous non-human TCRα and/or TCRβ constant gene locus.

The number, nomenclature, position, as well as other aspects of V and J and/or V, D, and J segments of the human and mouse TCR loci may be ascertained using the IMGT database, available at www.imgt.org. The mouse TCRα variable locus is approximately 1.5 megabases and comprises a total of 110Vα and 60 Jα segments (FIG. 2). The human TCRα variable locus is approximately 1 megabase and comprises a total of 54Vα and 61Jα segments, with 45Vα and 50Jα believed to be functional. Unless stated otherwise, the numbers of human V(D)J segments referred to throughout the specification refers to the total number of V(D)J segments. In one embodiment of the invention, the genetically modified non-human animal (e.g., rodent, e.g., mouse or rat) comprises at least one human Vα and at least one human Jα segment. In one embodiment, the non-human animal comprises a humanized TCRα locus that comprises 1, 2, 3, 4, 5, 6, 7, 8, 9, 10, 15, 20, 23, 25, 30, 35, 40, 45, 48, 50, or up to 54 human Vα segments. In some embodiments, the humanized TCRα locus comprises 2, 8, 23, 35, 48, or 54 human Vα segments. Thus, in some embodiments, the humanized TCRα locus in the non-human animal may comprise 5%, 10%, 15%, 20%, 25%, 30%, 35%, 40%, 45%, 50%, 55%, 60%, 65%, 70%, 75%, 80%, 85%, 90%, 95%, 96%, 97%, 98% 99%, or 100% of human Vα; in some embodiments, it may comprise about 2%, about 3%, about 15%, about 65%, about 90%, or 100% of human Vα.

In one embodiment, the non-human animal comprises a humanized TCRα locus that comprises a DNA fragment comprising a contiguous human sequence of human Vα 40 to Vα41 (Vα segment is also referred to as "TRAV" or "TCRAV") and a DNA fragment comprising a contiguous human sequence of 61 human Jα segments (Jα segment is also referred to as "TRAJ" or "TCRAJ"). In one embodiment, the non-human animal comprises a humanized TCRα locus that comprises a DNA fragment comprising a contiguous human sequence of human TRAV35 to TRAV41 and a DNA fragment comprising a contiguous human sequence of 61 human TRAJs. In one embodiment, the non-human animal comprises a humanized TCRα locus that comprises a DNA fragment comprising a contiguous human sequence of human TRAV22 to TRAV41 and a DNA fragment comprising a contiguous human sequence of 61 human TRAJs. In one embodiment, the non-human animal comprises a humanized TCRα locus that comprises a DNA fragment comprising a contiguous human sequence of human TRAV13-2 to TRAV41 and a DNA fragment comprising a contiguous human sequence of 61 human TRAJs. In one embodiment, the non-human animal comprises a humanized TCRα locus that comprises a DNA fragment comprising a contiguous human sequence of human TRAVδ to TRAV41 and 61 human TRAJs. In one embodiment, the non-human animal comprises a humanized TCRα locus that comprises a DNA fragment comprising a contiguous human sequence of human TRAV1-1 to TRAV 41 and 61 human TRAJs. In various embodiments, the DNA fragments comprising contiguous human sequences of human TCRα variable region segments also comprise restriction enzyme sites, selection cassettes, endonucleases sites, or other sites inserted to facilitate cloning and selection during the locus humanization process. In various embodiments, these additional sites do not interfere with proper functioning (e.g., rearrangement, splicing, etc.) of various genes at the TCRα locus.

In one embodiment, the humanized TCRα locus comprises 61 human Jα segments, or 100% of human Jα segments. In a particular embodiment, humanized TCRα locus comprises 8 human Vα segments and 61 human Jα segments; in another particular embodiment, humanized TCRα locus comprises 23 human Vα segments and 61 human Jα segments. In another particular embodiment, the humanized TCRα locus comprises a complete repertoire of human Vα and Jα segments, i.e., all human variable α region gene segments encoded by the α locus, or 54 human Vα and 61 human Jα segments. In various embodiments, the non-human animal does not comprise any endogenous non-human Vα or Jα segments at the TCRα locus.

Figure 6:
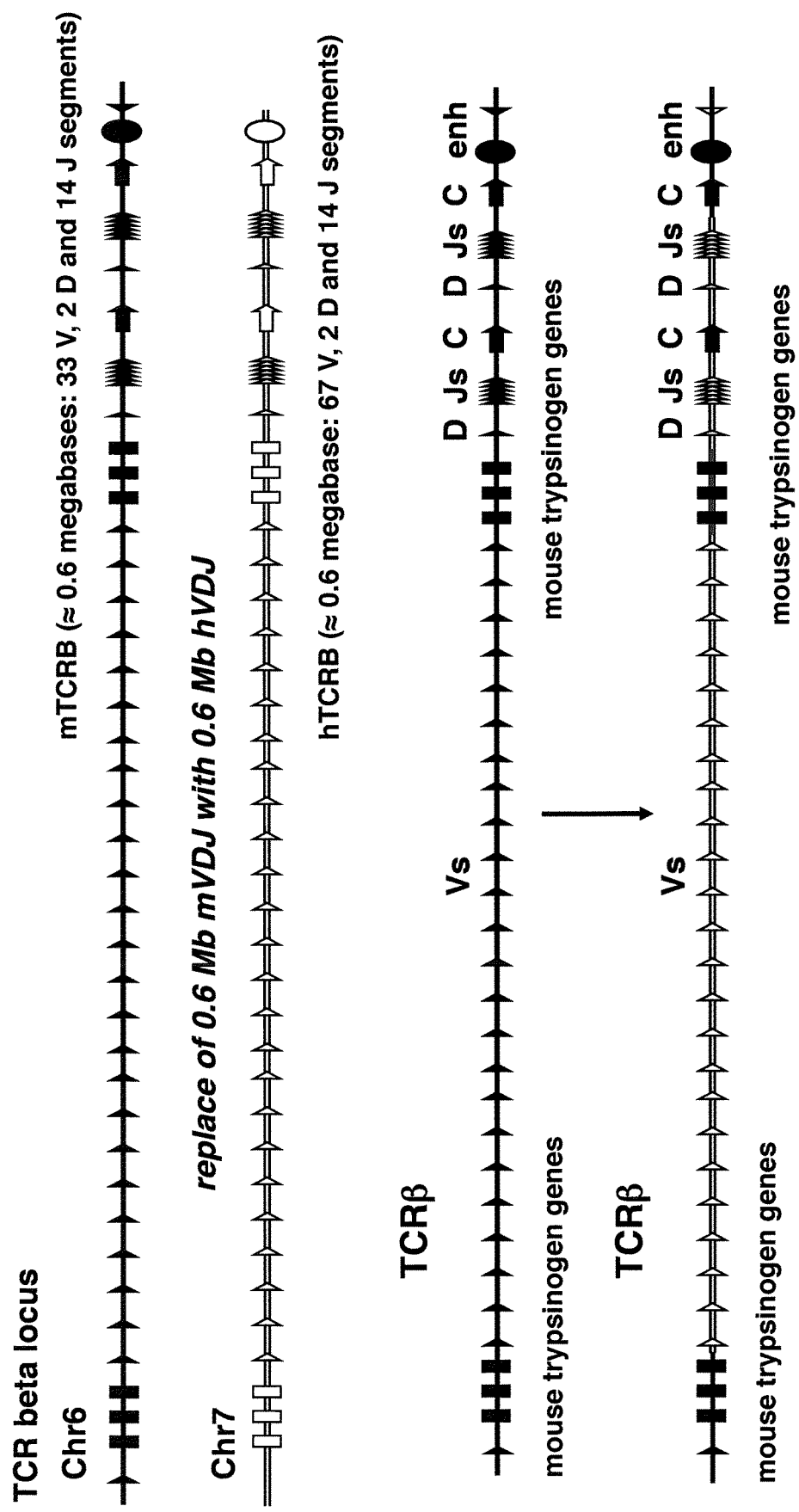
FIG. 6 depicts (not to scale) the general organization of a mouse (top panel, first locus; on mouse chromosome 6) and human (top panel, second locus; on human chromosome 7) TCRβ loci. The bottom panel illustrates a strategy for replacing TCRβ variable region segments in the mouse (closed symbols) with human TCRβ variable region segments (open symbols) at the endogenous mouse locus on mouse chromosome 6. The humanized TCR locus having human Vβ, Dβ, and Jβ segments is shown with mouse constant regions and a mouse enhancer; in the embodiment shown, the humanized locus retains mouse trypsinogen genes (solid rectangles); and in the particular embodiment shown, a single mouse V segment is retained upstream of the 5' mouse trypsinogen genes.

The mouse TCRβ variable locus is approximately 0.6 megabases and comprises a total of 33 Vβ, 2 Dβ, and 14 Jβ segments (FIG. 6). The human TCRβ variable locus is approximately 0.6 megabases and comprises a total of 67 Vβ, 2 Dβ, and 14 Jβ segments. In one embodiment of the invention, the genetically modified non-human animal (e.g., rodent, e.g., mouse or rat) comprises at least one human Vβ, at least one human Dβ, and at least one human Jα segment. In one embodiment, the non-human animal comprises a humanized TCRβ locus that comprises 1, 2, 3, 4, 5, 6, 7, 8, 9, 10, 15, 20, 23, 25, 30, 35, 40, 45, 48, 50, 55, 60, or up to human 67 Vβ segments. In some embodiments, the humanized TCRβ locus comprises 8, 14, 40, 66, or human 67 Vβ segments. Thus, in some embodiments, the humanized TCRβ locus in the non-human animal may comprise 5%, 10%, 15%, 20%, 25%, 30%, 35%, 40%, 45%, 50%, 55%, 60%, 65%, 70%, 75%, 80%, 85%, 90%, 95%, 96%, 97%, 98% 99%, or 100% of human Vβ; in some embodiments, it may comprise about 20%, about 60%, about 15%, about 98%, or 100% of human Vβ.

In one embodiment, the non-human animal comprises a humanized TCRβ locus that comprises a DNA fragment comprising a contiguous human sequence of human Vβ18 to Vβ29-1 (Vβ segment is also referred to as "TRBV" or "TCRBV"). In one embodiment, the non-human animal comprises a humanized TCRβ locus that comprises a DNA fragment comprising a contiguous human sequence of human TRBV18 to TRBV29-1, a separate DNA fragment comprising a contiguous human sequence of human Dβ1-Jβ1 (i.e., human Dβ1-Jβ1-1-Jβ1-6 segments), and a separate DNA fragment comprising a contiguous human sequence of human Dβ2-Jβ2 (i.e., human Dβ2-Jβ2-1-Jβ2-7 segments). In one embodiment, the non-human animal comprises a humanized TCRβ locus that comprises a DNA fragment comprising a contiguous human sequence of human TRBV6-5 to TRBV29-1, a separate DNA fragment comprising a contiguous human sequence of human Dβ1-Jβ1 (i.e., human Dβ1-Jβ1-1-Jβ1-6 segments), and a separate DNA fragment comprising a contiguous human sequence of human Dβ2-Jβ2 (i.e., human Dβ2-Jβ2-1-Jβ2-7 segments). In one embodiment, the non-human animal comprises a humanized TCRβ locus that comprises a DNA fragment comprising a contiguous human sequence of human TRBV1 to TRBV29-1, a separate DNA fragment comprising a contiguous human sequence of human Dβ1-Jβ1, and a separate DNA fragment comprising a contiguous human sequence of human Dβ2-Jβ2. In one embodiment, the non-human animal comprises a humanized TCRβ locus that comprises a DNA fragment comprising a contiguous human sequence of human TRBV1 to TRBV29-1, a separate DNA fragment comprising a contiguous human sequence of human Dβ1-Jβ1, a separate DNA fragment comprising a contiguous human sequence of human Dβ1-Jβ1, a separate DNA fragment comprising a contiguous human sequence of human Dβ2-Jβ2, and a separate DNA fragment comprising the sequence of human TRBV30. In various embodiments, the DNA fragments comprising contiguous human sequences of human TCRβ variable region segments also comprise restriction enzyme sites, selection cassettes, endonucleases sites, or other sites inserted to facilitate cloning and selection during the locus humanization process. In various embodiments, these additional sites do not interfere with proper functioning (e.g., rearrangement, splicing, etc.) of various genes at the TCRβ locus.

In one embodiment, the humanized TCRβ locus comprises 14 human Jβ segments, or 100% of human Jβ segments, and 2 human Dβ segments or 100% of human Jβ segments. In another embodiment, the humanized TCRβ locus comprises at least one human Vβ segment, e.g., 14 human Vβ segments, and all mouse Dβ and Jβ segments. In a particular embodiment, humanized TCRβ locus comprises 14 human Vβ segments, 2 human D3 segments, and 14 human Jβ segments. In another particular embodiment, the humanized TCRβ locus comprises a complete repertoire of human Vβ, Dβ, and Jβ segments, i.e., all human variable (3 region gene segments encoded by the β locus or 67 human Vβ, 2 human Vβ, and 14 human Jβ segments. In one embodiment, the non-human animal comprises one (e.g., 5') non-human Vβ segment at the humanized TCRβ locus. In various embodiments, the non-human animal does not comprise any endogenous non-human Vβ, Dβ, or Jβ segments at the TCRβ locus.

In various embodiments, wherein the non-human animal (e.g., rodent) comprises a repertoire of human TCRα and TCRβ (and optionally human TCRδ and TCRγ) variable region segments (e.g., a complete repertoire of variable region segments), the repertoire of various segments (e.g., the complete repertoire of various segments) is utilized by the animal to generate a diverse repertoire of TCR molecules to various antigens.

In various aspects, the non-human animals comprise contiguous portions of the human genomic TCR variable loci that comprise V, D, and J, or D and J, or V and J, or V segments arranged as in an unrearranged human genomic variable locus, e.g., comprising promoter sequences, leader sequences, intergenic sequences, regulatory sequences, etc., arranged as in a human genomic TCR variable locus. In other aspects, the various segments are arranged as in an unrearranged non-human genomic TCR variable locus. In various embodiments of the humanized TCRα and/or β locus, the humanized locus can comprise two or more human genomic segments that do not appear in a human genome juxtaposed, e.g., a fragment of V segments of the human V locus located in a human genome proximal to the constant region, juxtaposed with a fragment of V segments of the human V locus located in a human genome at the upstream end of the human V locus.

Figure 5:
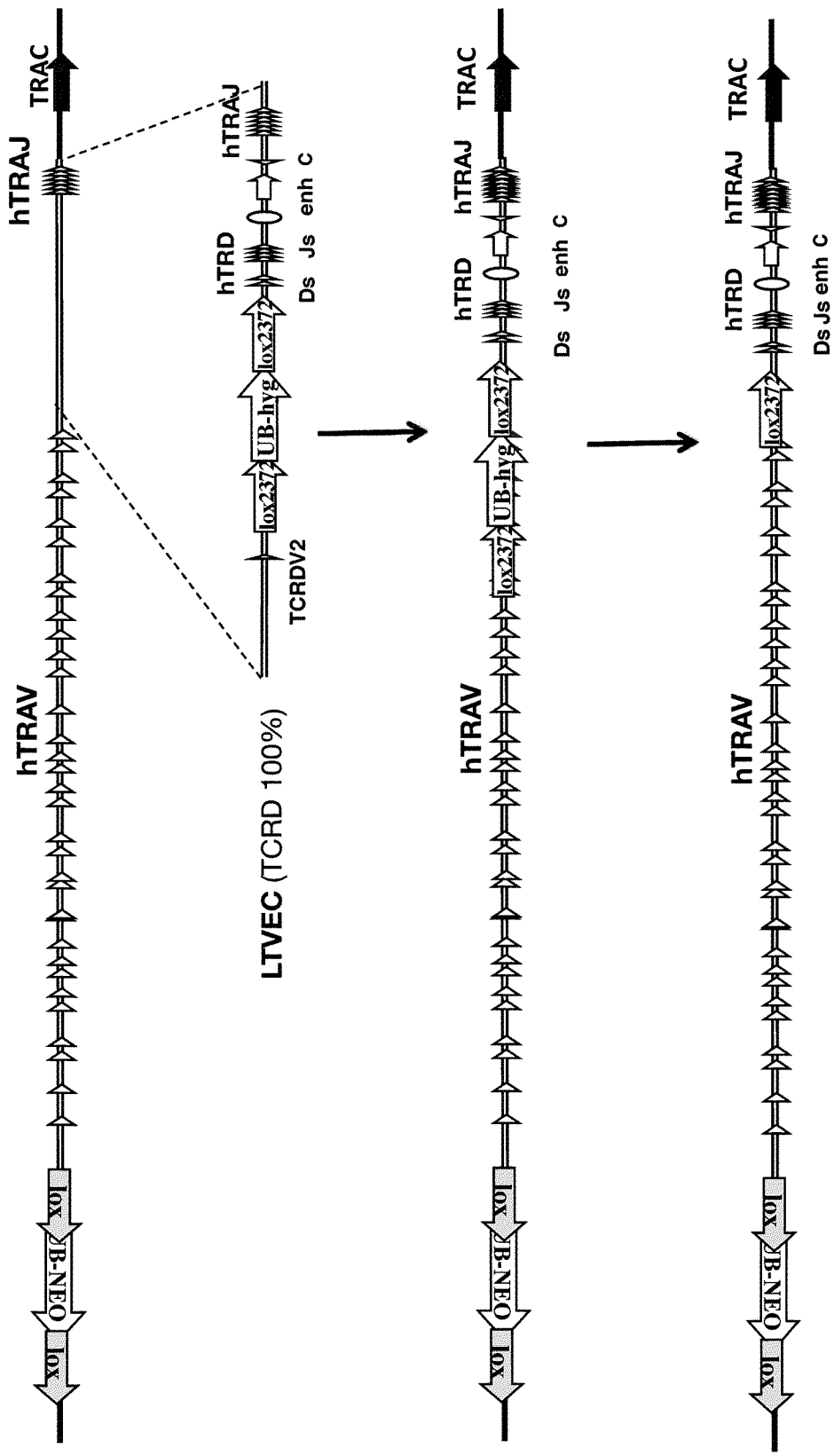
FIG. 5 depicts (not to scale) one embodiment of mouse TCRα locus humanization strategy, in which human TCR δ sequences (TCRδ Vs, TCRδ Ds, TCRδ Js, TCRδ enh (enhancer), and TCRδ constant (C)) are also placed at the humanized TCRα locus. Mouse sequence is indicated by closed symbols; human sequence is indicated by open symbols. LTVEC refers to a large targeting vector; hTRD=human TCRδ.

In both mouse and human, the TCRδ gene segments are located with the TCRα locus (see FIGS. 2 and 5). TCRδ J and D segments are located between Vα and Jα segments, while TCRδ V segments are interspersed throughout the TCRα locus, with the majority located among various Vα segments. The number and locations of various TCRβ segments can be determined from the IMGT database. Due to the genomic arrangement of TCRβ gene segments within the TCRα locus, successful rearrangement at the TCRα locus generally deletes the TCRδ gene segments.

In some embodiments of the invention, a non-human animal comprising an unrearranged human TCRα variable gene locus also comprises at least one human Vδ segment, e.g., up to complete repertoire of human VB segments. Thus, in some embodiments, the replacement of endogenous TCRα variable gene locus results in a replacement of at least one non-human VB segment with a human VB segment. In other embodiments, the non-human animal of the invention comprises a complete repertoire of human Vδ, Dδ, and Jδ segments at the unrearranged humanized TCRα locus; in yet other embodiments, the non-human animal comprises a complete unrearranged human TCRδ locus at the unrearranged humanized TCRα locus (i.e., a TCRδ locus including human variable region segments, as well as human enhancer and constant region). An exemplary embodiment for constructing an unrearranged humanized TCRα locus comprising complete unrearranged TCRδ locus is depicted in FIG. 5.

In yet another embodiment, the non-human animal of the invention further comprises an unrearranged humanized TCRγ locus, e.g., a TCRγ locus comprising at least one human Vγ and at least one human Jγ segments (e.g., a complete repertoire of human Vγ and human Jγ variable region segments). The human TCRγ locus is on human chromosome 7, while the mouse TCRγ locus is on mouse chromosome 13. See the IMGT database for more detail on the TCRγ locus.

In one aspect, the non-human animal (e.g., rodent, e.g., mouse or rat) comprising humanized TCRα and β variable gene loci (and, optionally humanized TCRβ/γ variable gene loci) described herein expresses a humanized T cell receptor comprising a human variable region and a non-human (e.g., rodent, e.g., mouse or rat) constant region on a surface of a T cell. In some aspects, the non-human animal is capable or expressing a diverse repertoire of humanized T cell receptors that recognize a variety of presented antigens.

In various embodiments of the invention, the humanized T cell receptor polypeptides described herein comprise human leader sequences. In alternative embodiments, the humanized TCR receptor nucleic acid sequences are engineered such that the humanized TCR polypeptides comprise non-human leader sequences.

The humanized TCR polypeptides described herein may be expressed under control of endogenous non-human regulatory elements (e.g., rodent regulatory elements), e.g., promoter, silencer, enhancer, etc. The humanized TCR polypeptides described herein may alternatively be expressed under control of human regulatory elements. In various embodiments, the non-human animals described herein further comprise all regulatory and other sequences normally found in situ in the human genome.

In various embodiments, the human variable region of the humanized TCR protein is capable of interacting with various proteins on the surface of the same cell or another cell. In one embodiment, the human variable region of the humanized TCR interacts with MHC proteins (e.g., MHC class I or II proteins) presenting antigens on the surface of the second cell, e.g., an antigen presenting cell (APC). In some embodiments, the MHC I or II protein is a non-human (e.g., rodent, e.g., mouse or rat) protein. In other embodiments, the MHC I or II protein is a human protein. In one aspect, the second cell, e.g., the APC, is an endogenous non-human cell expressing a human or humanized MHC molecule. In a different embodiment, the second cell is a human cell expressing a human MHC molecule.

In one aspect, the non-human animal expresses a humanized T cell receptor with a non-human constant region on the surface of a T cell, wherein the receptor is capable of interacting with non-human molecules, e.g., anchor or signaling molecules expressed in the T cell (e.g., CD3 molecules, the ξ chain, or other proteins anchored to the TCR through the CD3 molecules or the ξ chain).

Thus, in one aspect, a cellular complex is provided, comprising a non-human T-cell that expresses a TCR that comprises a humanized TCRα chain as described herein and humanized TCRβ chain as described herein, and a non-human antigen-presenting cell comprising an antigen bound to an MHC I or MHC II. In one embodiment, the non-human constant TCRα and TCRβ chains are complexed with a non-human zeta (ξ) chain homodimer and CD3 heterodimers. In one embodiment, the cellular complex is an in vivo cellular complex. In one embodiment, the cellular complex is an in vitro cellular complex.

The genetically modified non-human animal may be selected from a group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In one aspect, the non-human animal is a mammal. In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

In a specific embodiment, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In another embodiment, the mouse is a 129 strain selected from the group consisting of a strain that is 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more strains selected from the group consisting of Wistar, LEA, Sprague Dawley, Fischer, F344, F6, and Dark Agouti.

Thus, in one embodiment, the invention provides a genetically modified mouse comprising in its genome an unrearranged human or humanized TCR variable gene locus, e.g., TCRα, TCRβ, TCRδ, and/or TCRγ variable gene locus. In some embodiments, the unrearranged human or humanized TCR variable gene locus replaces endogenous mouse TCR variable gene locus. In other embodiments, unrearranged human or humanized TCR variable gene locus is at a site in the genome other than the corresponding endogenous mouse TCR locus. In some embodiments, human or humanized unrearranged TCR variable gene locus is operably linked to mouse TCR constant region.

In one embodiment, a genetically modified mouse is provided, wherein the mouse comprises in its genome an unrearranged T cell receptor (TCR) α variable gene locus comprising at least one human Jα segment and at least one human Vα segment, operably linked to a mouse TCRα constant gene sequence, and an unrearranged TCRβ variable gene locus comprising at least one human Jβ segment, at least one human Dβ segment, and at least one human Vβ segment, operably linked to a mouse TCRβ constant gene sequence. In one specific embodiment, the mouse comprises in its genome an unrearranged TCRα variable gene locus comprising a complete repertoire of human Jα segments and a complete repertoire of human Vα segments, operably linked to a mouse TCRα constant gene sequence, and an unrearranged TCRβ variable gene locus comprising a complete repertoire of human Jβ segments, a complete repertoire of human Dβ segments, and a complete repertoire of human Vβ segments, operably linked to a mouse TCRβ constant gene sequence.

In some embodiments, the unrearranged TCRα variable gene locus comprising human TCRα variable region segments replaces endogenous mouse TCRα variable gene locus, and the unrearranged TCRβ variable gene locus comprising human TCRβ variable region segments replaces the endogenous mouse TCRβ variable gene locus. In some embodiments, the endogenous mouse Vα and Jα segments are incapable of rearranging to form a rearranged Vα/Jα sequence, and the endogenous mouse Vβ, Dβ, and Jβ segments are incapable of rearranging to form a rearranged Vβ/Dβ/Jβ sequence. In some embodiments, the human Vα and Jα segments rearrange to form a rearranged human Vα/Jα sequence, and the human Vβ, Dβ, and Jβ segments rearrange to form a rearranged human Vβ/Dβ/Jβ sequence.

In various embodiments, the non-human animals (e.g., rodents, e.g., mice or rats) described herein produce T cells that are capable of undergoing thymic development, progressing from DN1 to DN2 to DN3 to DN4 to DP and to CD4 or CD8 SP T cells. Such T cells of the non-human animal of the invention express cell surface molecules typically produced by a T cell during a particular stage of thymic development (e.g., CD25, CD44, Kit, CD3, pTα, etc.). Thus, the non-human animals described herein express pTα complexed with TCRβ at the DN3 stage of thymic development. The non-human animals described herein express T cells capable of undergoing thymic development to produce CD4+ and CD8+ T cells. Normally, in the thymus the physiological ratio of CD4+ to CD8+ T cells is between about 2:1 and 3:1. See, e.g., Ge and Stanley (2008) The O-fucose glycan in the ligand-binding domain of Notch 1 regulates embryogenesis and T cell development, Proc. Natl. Acad. Sci. USA 105:1539-44. Thus, in one embodiment, the non-human animals described herein produce CD4+ and CD8+ T cells in the thymus at a ratio of between about 2:1 and 3:1 (CD4+:CD8+).

In various embodiments, the non-human animals described herein produce T cells that are capable of undergoing normal T cell differentiation in the periphery. In some embodiments, the non-human animals described herein are capable of producing a normal repertoire of effector T cells, e.g., CTL (cytotoxic T lymphocytes), $T_H1$, $T_H2$, $T_{REG}$, $T_H17$, etc. Thus, in these embodiments, the non-human animals described herein generate effector T cells that fulfill different functions typical of the particular T cell type, e.g., recognize, bind, and respond to foreign antigens. In various embodiments, the non-human animals described herein produce effector T cells that kill cells displaying peptide fragments of cytosolic pathogens expressed in the context of MHC I molecules; recognize peptides derived from antigens degraded in intracellular vesicles and presented by MHC II molecules on the surface of macrophages and induce macrophages to kill microorganisms; produce cytokines that drive B cell differentiation; activate B cells to produce opsonizing antibodies; induce epithelial cells to produce chemokines that recruit neutrophils to infection sites; etc.

In additional embodiments, the non-human animals described herein comprise a normal number of CD3+ T cells in the periphery, e.g., in the spleen. In some embodiments, the percent of peripheral CD3+ T cells in the non-human animals described herein is the comparable to that of the wild type animals (i.e., animals comprising all endogenous TCR variable region segments). In one embodiment, the non-human animals described herein comprise a normal ratio of splenic CD3+ T cells to total splenocytes.

In other aspects, the non-human animals described herein are capable of generating a population of memory T cells in response an antigen of interest. For example, the non-human animals generate both central memory T cells (Tcm) and effector memory T cells (Tem) to an antigen, e.g., antigen of interest (e.g., antigen being tested for vaccine development, etc.).

DN1 and DN2 cells that do not receive sufficient signals (e.g., Notch signals) may develop into B cells, myeloid cells (e.g., dendritic cells), mast cells and NK cells. See, e.g., Yashiro-Ohtani et al. (2010) Notch regulation of early thymocyte development, Seminars in Immunology 22:261-69. In some embodiments, the non-human animals described herein develop normal numbers of B cells, myeloid cells (e.g., dendritic cells), mast cells and NK cells. In some embodiments, the non-human animals described herein develop normal dendritic cell population in the thymus.

The predominant type of T cell receptors expressed on the surface of T cells is TCRα/β, with the minority of the cells expressing TCRδ/γ. In some embodiments of the invention, the T cells of the non-human animals comprising humanized TCRα and/or (3 loci exhibit normal utilization of TCRα/β and TCRδ/γ loci, e.g., utilization of TCRα/β and TCRδ/γ loci that is similar to the wild type animal (e.g., the T cells of the non-human animals described herein express TCRα/β and TCRδ/γ proteins in comparable proportions to that expressed by wild type animals). Thus, in some embodiments, the non-human animals comprising humanized TCRα/β and endogenous non-human TCRδ/γ loci exhibit normal utilization of all loci.

In addition to genetically engineered non-human animals described herein, a non-human embryo (e.g., a rodent embryo, e.g., mouse or a rat embryo) is also provided, wherein the embryo comprises a donor ES cell that is derived from a non-human animal (e.g., a rodent, e.g., a mouse or a rat) as described herein. In one aspect, the embryo comprises an ES donor cell that comprises an unrearranged humanized TCR locus, and host embryo cells.

Also provided is a tissue, wherein the tissue is derived from a non-human animal (e.g., a mouse or a rat) as described herein, and expresses a humanized TCR polypeptide (e.g., TCRα and/or TCRβ, or TCRδ, and/or TCRγ polypeptide).

In addition, a non-human cell isolated from a non-human animal as described herein is provided. In one embodiment, the cell is an ES cell. In one embodiment, the cell is a T cell. In one embodiment, the T cell is a CD4+ T cell. In another embodiment, the T cell is a CD8+ T cell.

Also provided is a non-human cell comprising a chromosome or fragment thereof of a non-human animal as described herein. In one embodiment, the non-human cell comprises a nucleus of a non-human animal as described herein. In one embodiment, the non-human cell comprises the chromosome or fragment thereof as the result of a nuclear transfer.

Also provided is a non-human cell that expresses a TCR protein comprising a human variable region and a non-human constant region. The TCR protein may comprise TCRα, TCRβ 3, or a combination thereof. In one embodiment, the cell is a T cell, e.g., a CD4+ or a CD8+ T cell.

In one aspect, a non-human induced pluripotent cell comprising an unrearranged humanized TCR locus encoding a humanized TCR polypeptide as described herein is provided.

In one embodiment, the induced pluripotent cell is derived from a non-human animal as described herein.

In one aspect, a hybridoma or quadroma is provided, derived from a cell of a non-human animal as described herein. In one embodiment, the non-human animal is a rodent, e.g., a mouse or rat.

Also provided is a method for making a genetically modified non-human animal (e.g., rodent, e.g., mouse or rat) described herein. The method for making a genetically modified non-human animal results in the animal whose genome comprises a humanized unrearranged TCR locus (e.g., a humanized unrearranged TCRα, TCRβ, TCRδ, and/or TCRγ locus). In one embodiment, a method for making a genetically modified non-human animal (e.g., rodent, e.g., mouse or rat) that expresses a T cell receptor comprising a human variable region and a non-human (e.g., rodent, e.g., mouse or rat) constant region on a surface of a T cell is provided, wherein the method comprises replacing in a first non-human animal an endogenous non-human TCRα variable gene locus with an unrearranged humanized TCRα variable gene locus comprising at least one human Vα segment and at least one human Jα segment, wherein the humanized TCRα variable gene locus is operably linked to endogenous TCRα constant region; replacing in a second non-human animal an endogenous non-human TCRβ variable gene locus with an unrearranged humanized TCRβ variable gene locus comprising at least one human Vβ segment, one human Dβ segment, and one human Jβ segment, wherein the humanized TCRβ variable gene locus is operably linked to endogenous TCR constant region; and breeding the first and the second non-human animal to obtain a non-human animal that expresses a T cell receptor comprising a human variable region and a non-human constant region. In other embodiments, the invention provides methods of making a genetically modified non-human animal whose genome comprises a humanized unrearranged TCRα locus, or a non-human animal whose genome comprises a humanized unrearranged TCRβ locus, generated according to the methods described herein. In various embodiments, the replacements are made at the endogenous loci. In some embodiments, the method utilizes one or more targeting constructs made using VELOCIGENE® technology, introducing the construct(s) into ES cells, and introducing targeted ES cell clones into a mouse embryo using VELOCIMOUSE® technology, as described in the Examples. In some embodiments, the ES cells are derived from a mouse that is a mix of 129 and C57BL/6 strains. In various embodiments, the method comprises progressive humanization strategy, wherein a construct comprising additional variable region segments is introduced into ES cells at each subsequent step of humanization, ultimately resulting in a mouse comprising a complete repertoire of human variable region segments (see, e.g., FIGS. 3 and 7).

Thus, nucleotide constructs used for generating genetically engineered non-human animals described herein are also provided. In one aspect, the nucleotide construct comprises: 5' and 3' homology arms, a human DNA fragment comprising human TCR variable region gene segment(s), and a selection cassette flanked by recombination sites. In one embodiment, the human DNA fragment is a TCRα gene fragment and it comprises at least one human TCRα variable region segment. In another embodiment, the human DNA fragment is a TCRβ fragment and it comprises at least one human TCRβ variable region gene segment. In one aspect, at least one homology arm is a non-human homology arm and it is homologous to non-human TCR locus (e.g., non-human TCRα or TCRβ locus).

A selection cassette is a nucleotide sequence inserted into a targeting construct to facilitate selection of cells (e.g., ES cells) that have integrated the construct of interest. A number of suitable selection cassettes are known in the art. Commonly, a selection cassette enables positive selection in the presence of a particular antibiotic (e.g., Neo, Hyg, Pur, CM, Spec, etc.). In addition, a selection cassette may be flanked by recombination sites, which allow deletion of the selection cassette upon treatment with recombinase enzymes. Commonly used recombination sites are loxP and Frt, recognized by Cre and Flp enzymes, respectively, but others are known in the art.

In one embodiment, the selection cassette is located at the 5' end the human DNA fragment. In another embodiment, the selection cassette is located at the 3' end of the human DNA fragment. In another embodiment, the selection cassette is located within the human DNA fragment, e.g., within the human intron. In another embodiment, the selection cassette is located at the junction of the human and mouse DNA fragment.

Various exemplary embodiments of the targeting strategy for generating genetically engineered non-human animals, the constructs, and the targeting vectors used for the same are presented in FIGS. 3, 4, 5, 7, and 8.

Upon completion of gene targeting, ES cells or genetically modified non-human animals are screened to confirm successful incorporation of exogenous nucleotide sequence of interest or expression of exogenous polypeptide (e.g., human TCR variable region segments). Numerous techniques are known to those skilled in the art, and include (but are not limited to) Southern blotting, long PCR, quantitative PCT (e.g., real-time PCR using TAQMAN®), fluorescence in situ hybridization, Northern blotting, flow cytometry, Western analysis, immunocytochemistry, immunohistochemistry, etc. In one example, non-human animals (e.g., mice) bearing the genetic modification of interest can be identified by screening for loss of mouse allele and/or gain of human allele using a modification of allele assay described in Valenzuela et al. (2003) High-throughput engineering of the mouse genome coupled with high-resolution expression analysis, Nature Biotech. 21(6):652-659. Other assays that identify a specific nucleotide or amino acid sequence in the genetically modified animals are known to those skilled in the art.

The disclosure also provides a method of modifying a TCR variable gene locus (e.g., TCRα, TCRβ, TCRδ, and/or TCRγ gene locus) of a non-human animal to express a humanized TCR protein described herein. In one embodiment, the invention provides a method of modifying a TCR variable gene locus to express a humanized TCR protein on a surface of a T cell wherein the method comprises replacing in a non-human animal an endogenous non-human TCR variable gene locus with an unrearranged humanized TCR variable gene locus. In one embodiment wherein the TCR variable gene locus is a TCRα variable gene locus, the unrearranged humanized TCR variable gene locus comprises at least one human Vα segment and at least one human Jα segment. In one embodiment wherein the TCR variable gene locus is a TCRβ variable gene locus, the unrearranged humanized TCR variable gene locus comprises at least one human Vβ segment, at least one human Dβ segment, and at least one human Jβ segment. In various aspects, the unrearranged humanized TCR variable gene locus is operably linked to the corresponding endogenous non-human TCR constant region.

A humanized TCR protein made by a non-human animal (e.g., rodent, e.g., mouse or rat) as described herein is also provided, wherein the humanized TCR protein comprises a human variable region and a non-human constant region. Thus, the humanized TCR protein comprises human complementary determining regions (i.e., human CDR1, 2, and 3) in its variable domain and a non-human constant region.

Although the Examples that follow describe a genetically engineered non-human animal whose genome comprises humanized TCRα and/or humanized TCRβ variable gene locus, one skilled in the art would understand that a similar strategy may be used to produce genetically engineered animals whose genome comprises humanized TCRδ and/or TCRγ variable gene locus. A genetically engineered non-human animal with humanization of all four TCR variable gene loci is also provided.

Use of Genetically Modified TCR Animals

In various embodiments, the genetically modified non-human animals of the invention make T cells with humanized TCR molecules on their surface, and as a result, would recognize peptides presented to them by MHC complexes in a human-like manner. The genetically modified non-human animals described herein may be used to study the development and function of human T cells and the processes of immunological tolerance; to test human vaccine candidates; to generate TCRs with certain specificities for TCR gene therapy; to generate TCR libraries to disease associated antigens (e.g., tumor associated antigens (TAAs); etc.

There is a growing interest in T cell therapy in the art, as T cells (e.g., cytotoxic T cells) can be directed to attack and lead to destruction of antigen of interest, e.g., viral antigen, bacterial antigen, tumor antigen, etc., or cells that present it. Initial studies in cancer T cell therapy aimed at isolation of tumor infiltrating lymphocytes (TILs; lymphocyte populations in the tumor mass that presumably comprise T cells reactive against tumor antigens) from tumor cell mass, expanding them in vitro using T cell growth factors, and transferring them back to the patient in a process called adoptive T cell transfer. See, e.g., Restifo et al. (2012) Adoptive immunotherapy for cancer: harnessing the T cell response, Nature Reviews 12:269-81; Linnermann et al. (2011) T-Cell Receptor Gene Therapy: Critical Parameters for Clinical Success, J. Invest. Dermatol. 131:1806-16. However, success of these therapies have thus far been limited to melanoma and renal cell carcinoma; and the TIL adoptive transfer is not specifically directed to defined tumor associated antigens (TAAs). Linnermann et al., supra.

Attempts have been made to initiate TCR gene therapy where T cells are either selected or programmed to target an antigen of interest, e.g., a TAA. Current TCR gene therapy relies on identification of sequences of TCRs that are directed to specific antigens, e.g., tumor associated antigens. For example, Rosenberg and colleagues have published several studies in which they transduced peripheral blood lymphocytes derived from a melanoma patient with genes encoding TCRα and β chains specific for melanoma-associated antigen MART-1 epitopes, and used resulting expanded lymphocytes for adoptive T cell therapy. Johnson et al. (2009) Gene therapy with human and mouse T-cell receptors mediates cancer regression and targets normal tissues expressing cognate antigen, Blood 114:535-46; Morgan et al. (2006) Cancer Regression in Patients After Transfer of Genetically Engineered Lymphocytes, Science 314: 126-29. The MART-1 specific TCRs were isolated from patients that experienced tumor regression following TIL therapy. However, identification of such TCRs, particularly high-avidity TCRs (which are most likely to be therapeutically useful), is complicated by the fact that most tumor antigens are self antigens, and TCRs targeting these antigens are often either deleted or possess suboptimal affinity, due primarily to immunological tolerance.

In various embodiments, the present invention solves this problem by providing genetically engineered non-human animals comprising in their genome an unrearranged human TCR variable gene locus. The non-human animal described herein is capable of generating T cells with a diverse repertoire of humanized T cell receptors. Thus, the non-human animals described herein may be a source of a diverse repertoire of humanized T cell receptors, e.g., high-avidity humanized T cell receptors for use in adoptive T cell transfer.

Thus, in one embodiment, the present invention provides a method of generating a T cell receptor to a human antigen comprising immunizing a non-human animal (e.g., a rodent, e.g., a mouse or a rat) described herein with an antigen of interest, allowing the animal to mount an immune response, isolating from the animal an activated T cell with specificity for the antigen of interest, and determining the nucleic acid sequence of the T cell receptor expressed by the antigen-specific T cell.

In one embodiment, the invention provides a method of producing a human T cell receptor specific for an antigen of interest (e.g., a disease-associated antigen) comprising immunizing a non-human animal described herein with the antigen of interest; allowing the animal to mount an immune response; isolating from the animal a T cell reactive to the antigen of interest; determining a nucleic acid sequence of a human TCR variable region expressed by the T cell; cloning the human TCR variable region into a nucleotide construct comprising a nucleic acid sequence of a human TCR constant region such that the human TCR variable region is operably linked to the human TCR constant region; and expressing from the construct a human T cell receptor specific for the antigen of interest. In one embodiment, the steps of isolating a T cell, determining a nucleic acid sequence of a human TCR variable region expressed by the T cell, cloning the human TCR variable region into a nucleotide construct comprising a nucleic acid sequence of a human TCR constant region, and expressing a human T cell receptor are performed using standard techniques known to those of skill the art.

In one embodiment, the nucleotide sequence encoding a T cell receptor specific for an antigen of interest is expressed in a cell. In one embodiment, the cell expressing the TCR is selected from a CHO, COS, 293, HeLa, PERC.6™ cell, etc.

The antigen of interest may be any antigen that is known to cause or be associated with a disease or condition, e.g., a tumor associated antigen; an antigen of viral, bacterial or other pathogenic origin; etc. Many tumor associated antigens are known in the art. A selection of tumor associated antigens is presented in Cancer Immunity (A Journal of the Cancer Research Institute) Peptide Database (archive.cancerimmunity.org/peptidedatabase/Tcellepitopes.htm). In some embodiments of the invention, the antigen of interest is a human antigen, e.g., a human tumor associated antigen. In some embodiments, the antigen is a cell type-specific intracellular antigen, and a T cell receptor is used to kill a cell expressing the antigen.

In one embodiment, provided herein is a method of identifying a T cell with specificity against an antigen of interest, e.g., a tumor associated antigen, comprising immunizing a non-human animal described herein with the antigen of interest, allowing the animal to mount an immune response, and isolating from the non-human animal a T cell with specificity for the antigen.

The present invention provides new methods for adoptive T cell therapy. Thus, provided herein is a method of treating or ameliorating a disease or condition (e.g., a cancer) in a subject (e.g., a mammalian subject, e.g., a human subject) comprising immunizing a non-human animal described herein with an antigen associated with the disease or condition, allowing the animal to mount an immune response, isolating from the animal a population of antigen-specific T cells, and infusing isolated antigen-specific T cells into the subject. In one embodiment, the invention provides a method of treating or ameliorating a disease or condition in a human subject, comprising immunizing the non-human animal described herein with an antigen of interest (e.g., a disease- or condition-associated antigen, e.g., a tumor associated antigen), allowing the animal to mount an immune response, isolating from the animal a population of antigen-specific T cells, determining the nucleic acid sequence of a T cell receptor expressed by the antigen-specific T cells, cloning the nucleic acid sequence of the T cell receptor into an expression vector (e.g., a retroviral vector), introducing the vector into T cells derived from the subject such that the T cells express the antigen-specific T cell receptor, and infusing the T cells into the subject. In one embodiment, the T cell receptor nucleic acid sequence is further humanized prior to introduction into T cells derived from the subject, e.g., the sequence encoding the non-human constant region is modified to further resemble a human TCR constant region (e.g., the non-human constant region is replaced with a human constant region). In some embodiments, the disease or condition is cancer. In some embodiments, an antigen-specific T cell population is expanded prior to infusing into the subject. In some embodiments, the subject's immune cell population is immunodepleted prior to the infusion of antigen-specific T cells. In some embodiments, the antigen-specific TCR is a high avidity TCR, e.g., a high avidity TCR to a tumor associated antigen. In some embodiments, the T cell is a cytotoxic T cell. In other embodiments, the disease or condition is caused by a virus or a bacterium.

In another embodiment, a disease or condition is an autoimmune disease. $T_{REG}$ cells are a subpopulation of T cells that maintain tolerance to self-antigens and prevent pathological self-reactivity. Thus, also provided herein are methods of treating autoimmune disease that rely on generation of antigen-specific $T_{REG}$ cells in the non-human animal of the invention described herein.

Also provided herein is a method of treating or ameliorating a disease or condition (e.g., a cancer) in a subject comprising introducing the cells affected by the disease or condition (e.g., cancer cells) from the subject into a non-human animal, allowing the animal to mount an immune response to the cells, isolating from the animal a population of T cells reactive to the cells, determining the nucleic acid sequence of a T cell receptor expressed by the T cells, cloning the T cell receptor sequence into a vector, introducing the vector into T cells derived from the subject, and infusing the subject's T cells harboring the T cell receptor into the subject.

Also provided herein is the use of a non-human animal as described herein to make nucleic acid sequences encoding human TCR variable domains (e.g., TCR α and/or β variable domains). In one embodiment, a method is provided for making a nucleic acid sequence encoding a human TCR variable domain, comprising immunizing a non-human animal as described herein with an antigen of interest, allowing the non-human animal to mount an immune response to the antigen of interest, and obtaining therefrom a nucleic acid sequence encoding a human TCR variable domain that binds the antigen of interest. In one embodiment, the method further comprises making a nucleic acid sequence encoding a human TCR variable domain that is operably linked to a non-human TCR constant region, comprising isolating a T cell from a non-human animal described herein and obtaining therefrom the nucleic acid sequence encoding TCR variable domain linked to TCR constant region.

Also provided herein is the use of a non-human animal as described herein to make a human therapeutic, comprising immunizing the non-human animal with an antigen of interest (e.g., a tumor associated antigen), allowing the non-human animal to mount an immune response, obtaining from the animal T cells reactive to the antigen of interest, obtaining from the T cells a nucleic acid sequence(s) encoding a humanized TCR protein that binds the antigen of interest, and employing the nucleic acid sequence(s) encoding a humanized TCR protein in a human therapeutic.

Thus, also provided is a method for making a human therapeutic, comprising immunizing a non-human animal as described herein with an antigen of interest, allowing the non-human animal to mount an immune response, obtaining from the animal T cells reactive to the antigen of interest, obtaining from the T cells a nucleic acid sequence(s) encoding a humanized T cell receptor that binds the antigen of interest, and employing the humanized T cell receptor in a human therapeutic.

In one embodiment, the human therapeutic is a T cell (e.g., a human T cell, e.g., a T cell derived from a human subject) harboring a nucleic acid sequence of interest (e.g., transfected or transduced or otherwise introduced with the nucleic acid of interest) such that the T cell expresses the humanized TCR protein with affinity for an antigen of interest. In one aspect, a subject in whom the therapeutic is employed is in need of therapy for a particular disease or condition, and the antigen is associated with the disease or condition. In one aspect, the T cell is a cytotoxic T cell, the antigen is a tumor associated antigen, and the disease or condition is cancer. In one aspect, the T cell is derived from the subject.

In another embodiment, the human therapeutic is a T cell receptor. In one embodiment, the therapeutic receptor is a soluble T cell receptor. Much effort has been expanded to generate soluble T cell receptors or TCR variable regions for use therapeutic agents. Generation of soluble T cell receptors depends on obtaining rearranged TCR variable regions. One approach is to design single chain TCRs comprising TCRα and TCRβ, and, similarly to scFv immunoglobulin format, fuse them together via a linker (see, e.g., International Application No. WO 2011/044186). The resulting scTv, if analogous to scFv, would provide a thermally stable and soluble form of TCRα/β binding protein. Alternative approaches included designing a soluble TCR having TCRβ constant domains (see, e.g., Chung et al., (1994) Functional three-domain single-chain T-cell receptors, Proc. Natl. Acad. Sci. USA. 91:12654-58); as well as engineering a non-native disulfide bond into the interface between TCR constant domains (reviewed in Boulter and Jakobsen (2005) Stable, soluble, high-affinity, engineered T cell receptors: novel antibody-like proteins for specific targeting of peptide antigens, Clinical and Experimental Immunology 142:454-60; see also, U.S. Pat. No. 7,569,664). Other formats of soluble T cell receptors have been described. The non-human animals described herein may be used to determine a sequence of a T cell receptor that binds with high affinity to an antigen of interest, and subsequently design a soluble T cell receptor based on the sequence.

A soluble T cell receptor derived from the TCR receptor sequence expressed by the non-human animal can be used to block the function of a protein of interest, e.g., a viral, bacterial, or tumor associated protein. Alternatively, a soluble T cell receptor may be fused to a moiety that can kill an infected or cancer cell, e.g., a cytotoxic molecules (e.g., a chemotherapeutic), toxin, radionuclide, prodrug, antibody, etc. A soluble T cell receptor may also be fused to an immunomodulatory molecule, e.g., a cytokine, chemokine, etc. A soluble T cell receptor may also be fused to an immune inhibitory molecule, e.g., a molecule that inhibits a T cell from killing other cells harboring an antigen recognized by the T cell. Such soluble T cell receptors fused to immune inhibitory molecules can be used, e.g., in blocking autoimmunity. Various exemplary immune inhibitory molecules that may be fused to a soluble T cell receptor are reviewed in Ravetch and Lanier (2000) Immune Inhibitory Receptors, Science 290:84-89, incorporated herein by reference.

The present invention also provides methods for studying immunological response in the context of human TCR, including human TCR rearrangement, T cell development, T cell activation, immunological tolerance, etc.

Also provided are methods of testing vaccine candidates. In one embodiment, provided herein is a method of determining whether a vaccine will activate an immunological response (e.g., T cell proliferation, cytokine release, etc.), and lead to generation of effector, as well as memory T cells (e.g., central and effector memory T cells).

EXAMPLES

The invention will be further illustrated by the following nonlimiting examples. These Examples are set forth to aid in the understanding of the invention but are not intended to, and should not be construed to, limit its scope in any way. The Examples do not include detailed descriptions of conventional methods that would be well known to those of ordinary skill in the art (molecular cloning techniques, etc.). Unless indicated otherwise, parts are parts by weight, molecular weight is average molecular weight, temperature is indicated in Celsius, and pressure is at or near atmospheric.

Example 1

Generation of Mice with Humanized TCR Variable Gene Loci

Mice comprising a deletion of endogenous TCR (α or β) variable loci and replacement of endogenous V and J or V, D, and J segments are made using VELOCIGENE® genetic engineering technology (see, e.g., U.S. Pat. No. 6,586,251 and Valenzuela, D. M., et al. (2003) High-throughput engineering of the mouse genome coupled with high-resolution expression analysis. Nat. Biotech. 21(6): 652-659), wherein human sequences derived from BAC libraries using bacterial homologous recombination are used to make large targeting vectors (LTVECs) comprising genomic fragments of human TCR variable loci flanked by targeting arms to target the LTVECs to endogenous mouse TCR variable loci in mouse ES cells. LTVECs re linearized and electroporated into a mouse ES cell line according to Valenzuela et al. ES cells are selected for hygromycin or neomycin resistance, and screened for loss of mouse allele or gain of human allele.

Targeted ES cell clones are introduced into 8-cell stage (or earlier) mouse embryos by the VELOCIMOUSE® method (Poueymirou, W. T. et al. (2007). F0 generation mice fully derived from gene-targeted embryonic stem cells allowing immediate phenotypic analyses. Nat. Biotech. 25: 91-99.). VELOCIMICE® (F0 mice fully derived from the donor ES cell) bearing humanized TCR loci are identified by screening for loss of endogenous TCR variable allele and gain of human allele using a modification of allele assay (Valenzuela et al.). F0 pups are genotyped and bred to homozygosity. Mice homozygous for humanized TCRα and/or TCRβ variable loci (e.g., comprising a subset of human TCRα and/or TCRβ variable segments) are made and phenotyped as described herein.

All mice were housed and bred in the specific pathogen-free facility at Regeneron Pharmaceuticals. All animal experiments were approved by IACUC and Regeneron Pharmaceuticals.

Example 2

Figure 3:
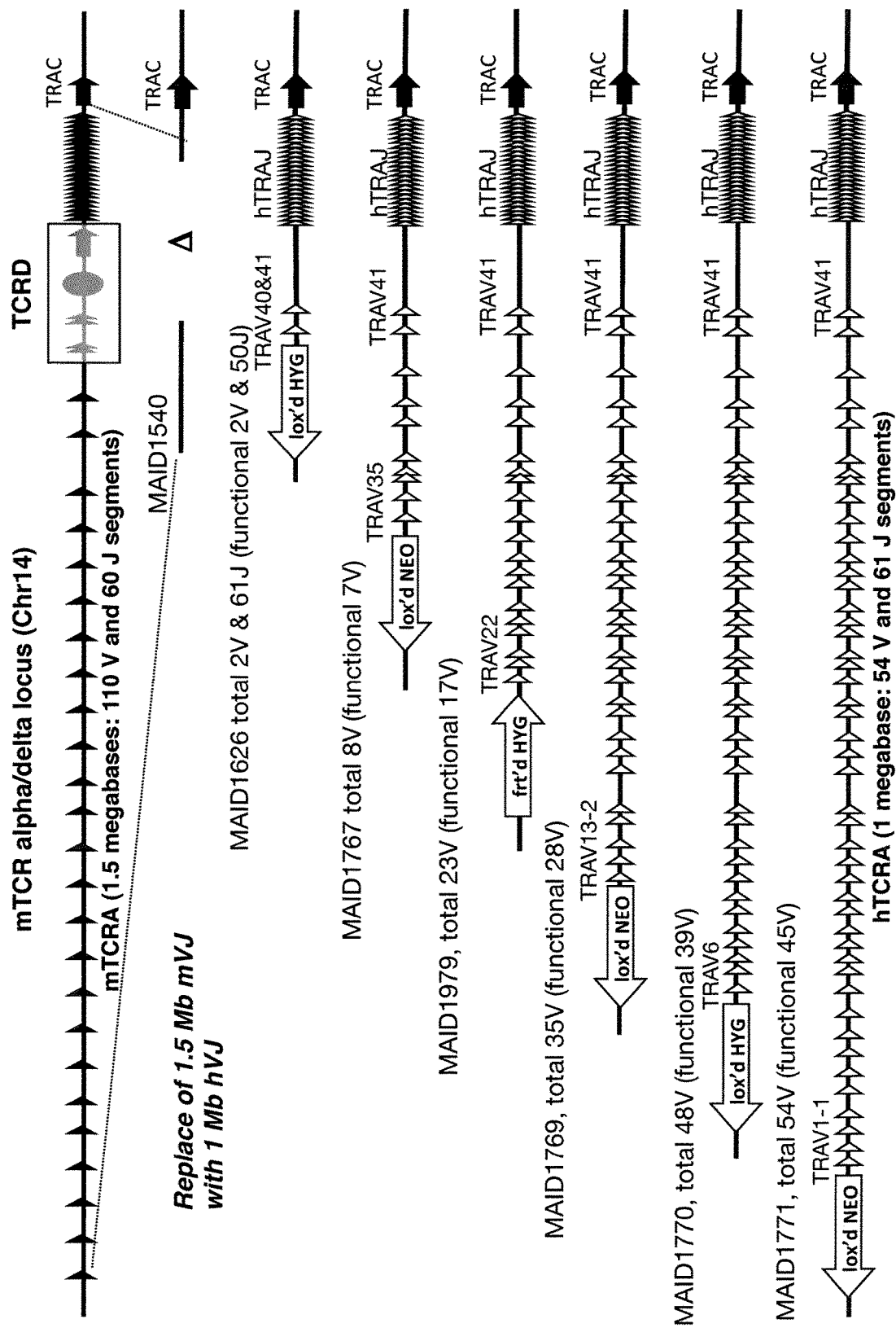
FIG. 3 depicts (not to scale) a progressive strategy for humanization of the mouse TCRα locus, wherein TCRα variable region gene segments are sequentially added upstream of an initial humanization of a deleted mouse locus (MAID1540). Mouse sequence is indicated by closed symbols; human sequence is indicated by open symbols. MAID refers to modified allele ID number. TRAV=TCR Vα segment, TRAJ=TCR Jα segment (hTRAJ=human TRAJ), TRAC=TCR Cα domain, TCRD=TCRδ.

Progressive Humanization of TCRα Variable Locus 1.5 megabases of DNA at mouse TCRα locus corresponding to 110 V and 60 J mouse segments was replaced with 1 megabase of DNA corresponding to 54V and 61J segments of human TCRα using a progressive humanization strategy summarized in FIGS. 2 and 3. Junctional nucleic acid sequences of various targeting vectors used for progressive humanization strategy of TCRα locus are summarized in Table 2, and included in the Sequence Listing.

TABLE 2

Junctional Nucleic Acid Sequences for Various TCRα Locus Targeting Vectors

| MAID NO. | SEQ ID NO | Description |
|---|---|---|
| 1626 | 1 | Junctional nucleic acid sequence between the 3' end of mouse sequence upstream of the TCRα variable locus and the 5' end of loxP-Ub-Hyg-loxP cassette. |
|  | 2 | Junctional nucleic acid sequence between the 3' end of loxP-Ub-Hyg-loxP cassette and the 5' end of human TCRVα40-TCRVα41-TCRJα1 insertion, including AsiSI site. |
|  | 3 | Junctional nucleic acid sequence between the 3' end of human TCRVα40-TCRVα41-TCRJα1 insertion and the 5' end of the mouse sequence downstream of the human TCRα variable locus, including NotI site. |
| 1767 | 4 | Junctional nucleic acid sequence between the 3' end of mouse sequence upstream of the TCRα variable locus and the 5' end of loxP-Ub-Neo-loxP cassette. |
|  | 5 | Junctional nucleic acid sequence between the 3' end of loxP-Ub-Neo-loxP cassette and the 5' end of human TCRVα35-TCRVα39 insertion, including AsiSI site. |
| 1979 | 6 | Junctional nucleic acid sequence between the 3' end of mouse sequence upstream of the TCRα variable locus and the 5' end of frt-Pgk-Hyg-frt cassette. |
|  | 7 | Junctional nucleic acid sequence between the 3' end of frt-Pgk-Hyg-frt cassette and the 5' end of human TCRVα22-TCRVα34 insertion, including AsiSI site. |
| 1769 | 8 | Junctional nucleic acid sequence between the 3' end of mouse sequence upstream of the TCRα variable locus and the 5' end of loxP-Ub-Neo-loxP cassette. |
|  | 9 | Junctional nucleic acid sequence between the 3' end of loxP-Ub-Neo-loxP cassette and the 5' end of human TCRVα13-2-TCRVα21 insertion, including AsiSI site. |
| 1770 | 10 | Junctional nucleic acid sequence between the 3' end of mouse sequence upstream of the TCRα variable locus and the 5' end of loxP-Ub-Hyg-loxP cassette. |
|  | 11 | Junctional nucleic acid sequence between the 3' end of loxP-Ub-Hyg-loxP cassette and the 5' end of human TCRVα6-TCRVα8-5 insertion, including AsiSI site. |
| 1771 | 12 | Junctional nucleic acid sequence between the 3' end of mouse sequence upstream and the TCRα variable locus to the 5' end of loxP-Ub-Neo-loxP cassette. |
|  | 13 | Junctional nucleic acid sequence between the 3' end of loxP-Ub-Neo-loxP cassette and the 5' end of human TCRVα1-1-TCRVα5 insertion, including AsiSI site. |

Human TCRα variable region segments are numbered as in IMGT database. At least 100 bp at each junction (about 50 bp from each end) are included in the Sequence Listing.

Figure 4A:
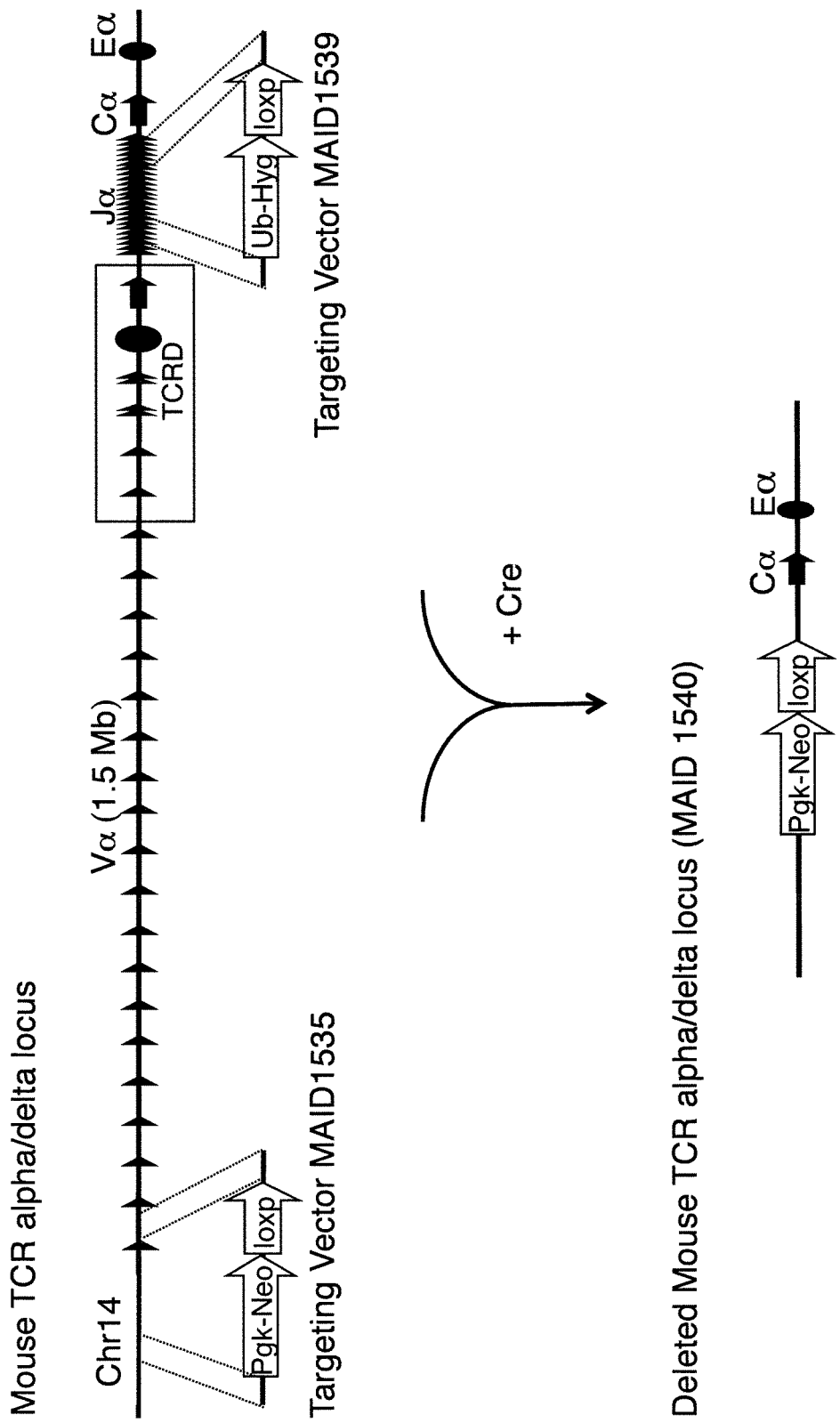
FIGS. 4A, 4B, 4C, 4D, 4E, 4F and 4G are a detailed depiction (not to scale) of progressive humanization strategy at the TCRα locus.

Specifically, as demonstrated in FIG. 4A, DNA from mouse BAC clone RP23-6A14 (Invitrogen) was modified by homologous recombination and used as a targeting vector (MAID 1539) to replace TCRAJ1-TCRAJ28 region of the endogenous mouse TCRα locus with a Ub-hygromycin cassette followed by a loxP site. DNA from mouse BAC clone RP23-117i19 (Invitrogen) was modified by homologous recombination and used as a targeting vector (MAID 1535) to replace ~15 kb region surrounding (and including) TCRAV1 of the endogenous mouse TCRα and δ locus with a PGK-neomycin cassette followed by a loxP site. ES cells bearing a double-targeted chromosome (i.e., a single endogenous mouse TCRα locus targeted with both targeting vectors) were confirmed by karyotyping and screening methods (e.g., TAQMAN™) known in the art. Modified ES cells were treated with CRE recombinase, thereby mediating the deletion of the region between the two loxP sites (i.e., the region consisting of the endogenous mouse TCRα locus from TCRAV1 to TCRAJ1) and leaving behind only a single loxP site, neomycin cassette and the mouse constant and enhancer regions. This strategy resulted in generation of a deleted mouse TCR α/δ locus (MAID 1540).

Figure 4B:
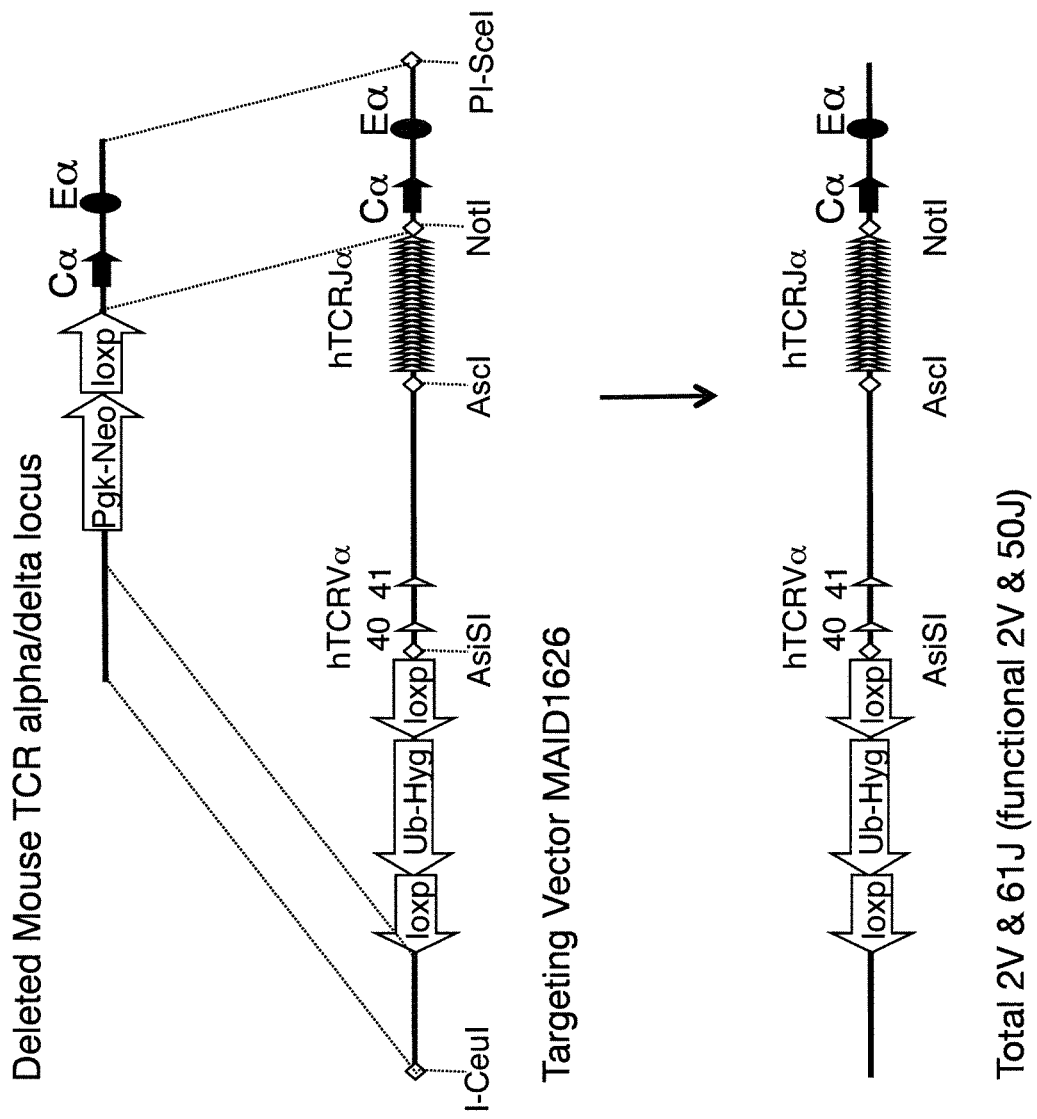

The first human targeting vector for TCRα had 191,660 bp of human DNA from the CTD2216p1 and CTD2285m07 BAC clones (Invitrogen) that contained the first two consecutive human TCRαV gene segments (TRAV40 & 41) and 61 TCRαJ (50 functional) gene segments. This BAC was modified by homologous recombination to contain a Not1 site 403 bp downstream (3') of the TCRαJ1 gene segment for ligation of a 3' mouse homology arm and a 5' AsiSI site for ligation of a 5' mouse homology arm. Two different homology arms were used for ligation to this human fragment: the 3' homology arm contained endogenous mouse TCRα sequences from the RP23-6A14 BAC clone and the 5' homology arm contained endogenous TCRα sequence 5' of mouse TCRαV from mouse BAC clone RP23-117i19. This mouse-human chimeric BAC was used as a targeting vector (MAID 1626) for making an initial insertion of human TCRα gene segments plus an upstream loxp-ub-hygromycin-loxp cassette at the mouse TCRα loci (FIG. 4B). The junctional nucleic acid sequences (SEQ ID NOs: 1-3) for the MAID 1626 targeting vector are described in Table 2.

Subsequently, a series of human targeting vectors were made that utilized the same mouse 5' arm that contained endogenous TCRα sequence 5' of mouse TCRαV from mouse BAC clone RP23-117i19 with alternating loxP-neomycin-loxP and loxP-hygromycin-loxP (or frt-hygromycin-frt for MAID 1979) selection cassettes.

Figure 4C:
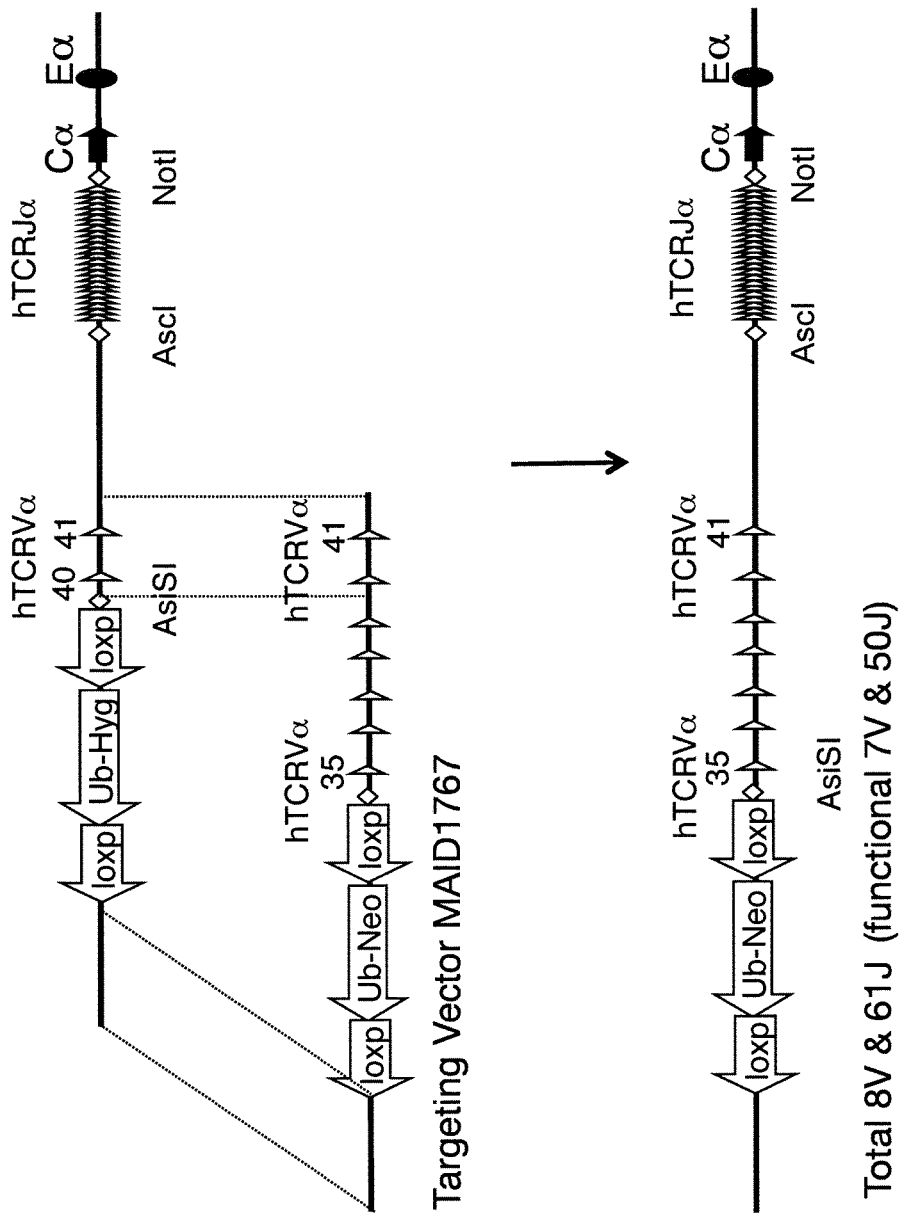

To generate a human TCRα mini-locus containing a total 8 human TCRαV (7 functional) and 61 human TCRαJ (50 functional) gene segments, DNA from human BAC clone RP11-349p11 (Invitrogen) was modified by homologous recombination and used as a targeting vector (MAID 1767) (FIG. 4C). This added 104,846 bp of human DNA containing the next 6 (5 functional) consecutive human TCRαV gene segments (TRAV35 to TRAV39) and a 5' loxP-ub-neomycin-loxP cassette. Resulting TCRα locus contained a 5'/oxp-ub-neomycin-loxP cassette plus a total of 8 human TCRαV (7 functional) and 61 human TCRαJ gene segments operably linked to mouse TCRα constant genes and enhancers. The junctional nucleic acid sequences (SEQ ID NOs: 4 and 5) for the MAID 1767 targeting vector are described in Table 2.

Figure 4D:
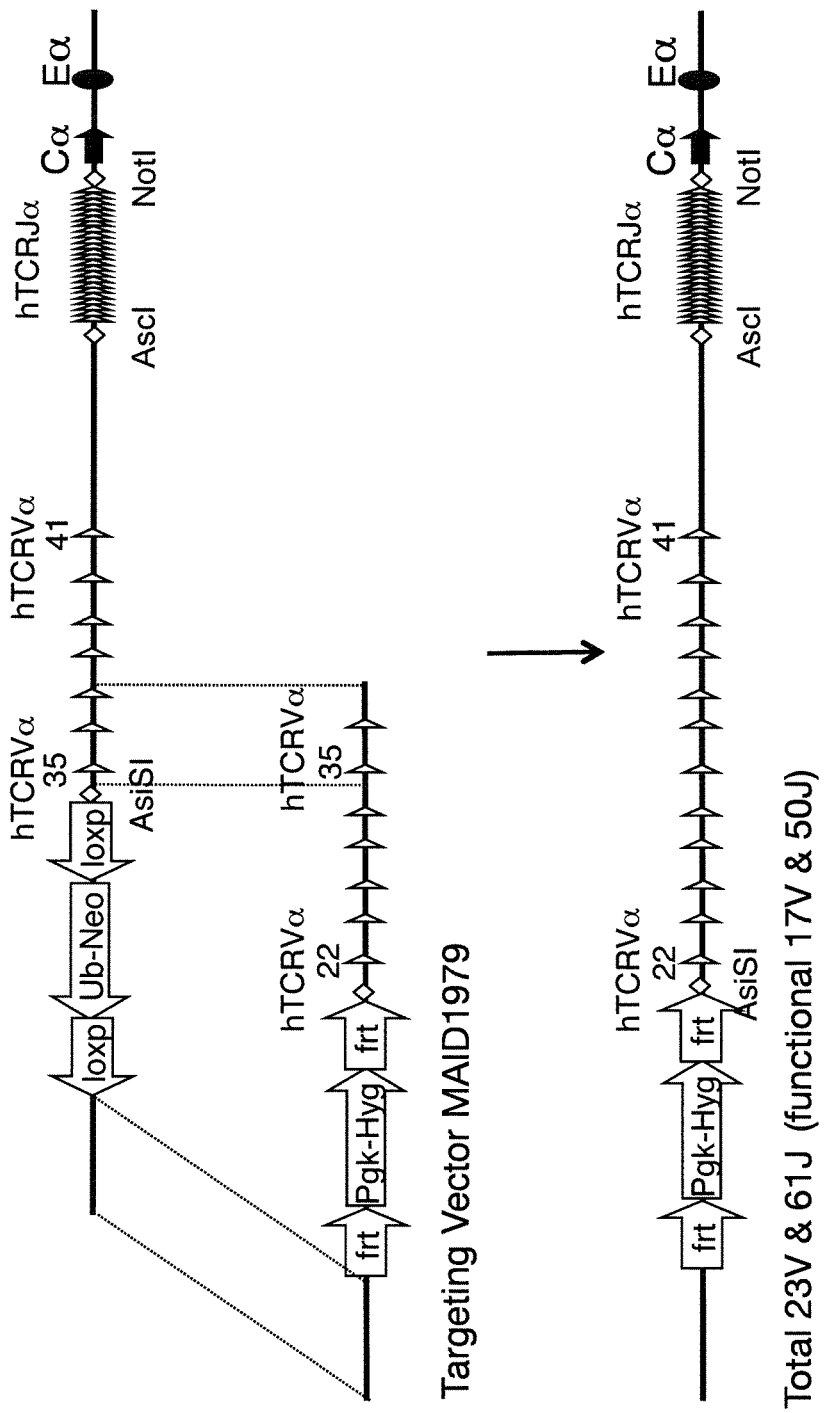

To generate a human TCRα mini-locus containing total of 23 human TCRαV (17 functional) and 61 human TCRα J gene segments, DNA from mouse BAC clone containing from 5' to 3': a unique I-Ceul site, a 20 kb mouse TCRA arm 5' of the mouse TCRA locus to be used for homologous recombination into ES cells, and a loxP-Ub-Hyg-loxP cassette in reverse orientation, was modified by bacterial homologous recombination to contain from 5' to 3': a unique I-Ceul site, a 20 kb mouse TCRA arm 5' of the mouse TCRA locus, an frt-pgk-Hyg-frt cassette, and a unique AsiSI site. DNA from human BAC clone RP11-622o20 (Invitrogen), harboring human TCRαV22-V34 was modified by homologous recombination to contain a Spec cassette flanked by unique I-Ceul and AsiSI sites. Subsequently, the Spec cassette in the modified human BAC clone was replaced by the sequence comprised between the I-Ceul and AsiSI sites in the modified mouse BAC clone by standard restriction digestion/ligation techniques. The resulting targeting vector (MAID 1979; FIG. 4D) added 136,557 bp of human DNA that contained the next 15 (10 functional) consecutive human TCRαJ gene segments (TRAV22 to TRAV34) and a 5' frt-pgk-Hyg-frt cassette. Resulting TCRα locus contained a 5' frt-pgk-Hyg-frt cassette plus a total of 23 human TCRαV (17 functional) and 61 human TCRαV gene segments operably linked to mouse TCRα constant genes and enhancers. The junctional nucleic acid sequences (SEQ ID NOs: 6 and 7) for the MAID 1979 targeting vector are described in Table 2.

Figure 4E:
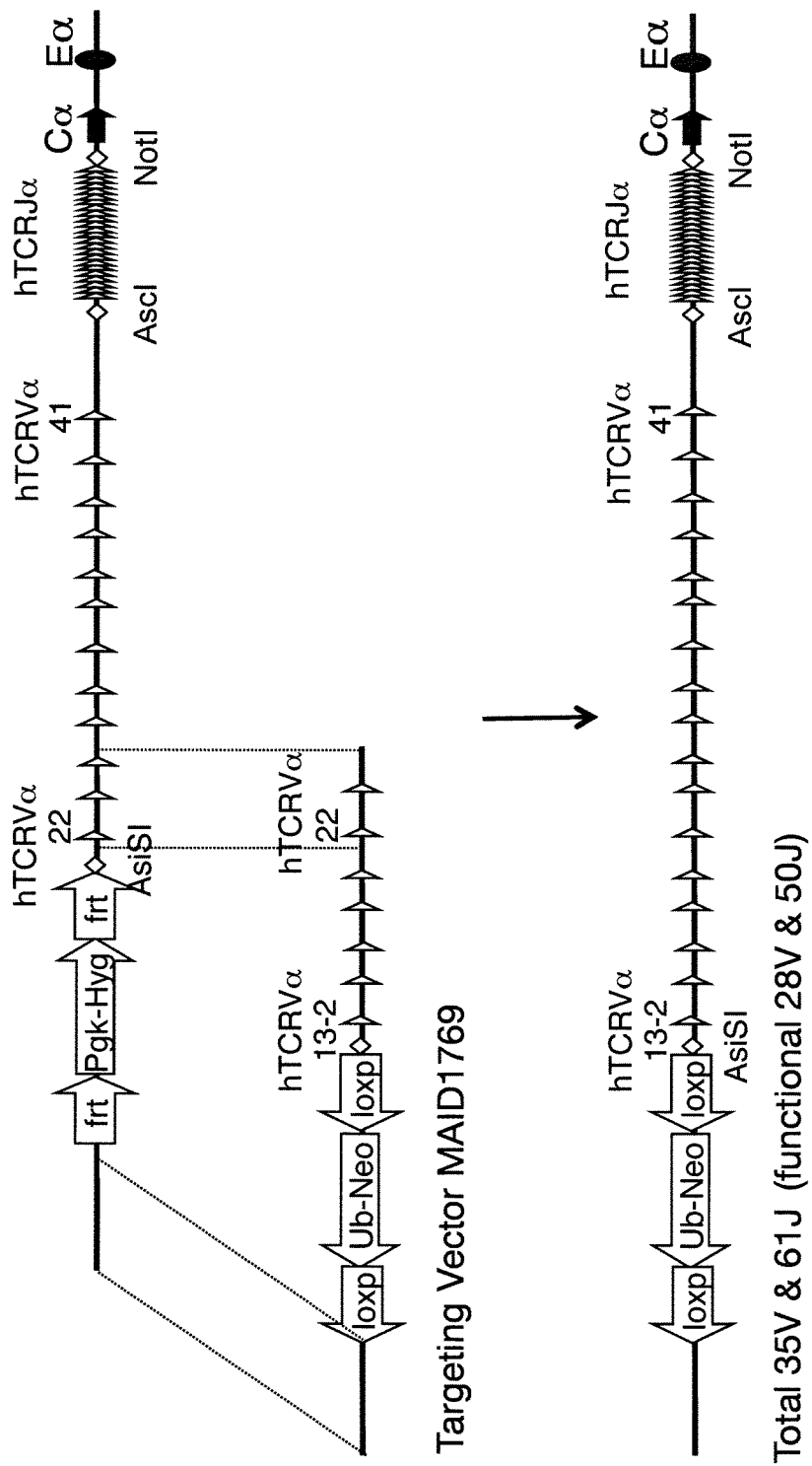

To generate human TCRα mini-locus containing a total of 35 human TCRαV (28 functional) and 61 human TCRαJ gene segments, DNA from human BAC clone CTD2501-k5 (Invitrogen) was modified by homologous recombination and used as a targeting vector (MAID 1769) (FIG. 4E). This added 124,118 bp of human DNA that contained the next 12 (11 functional) consecutive human TCRαV gene segments (TRAV13-2 to TRAV21) and a 5' loxp-ub-neomycin-loxP cassette. Resulting TCRα locus contained a 5' loxp-ub-neomycin-loxP cassette plus a total of 35 human TCRαV (28 functional) and 61 human TCRαJ gene segments operably linked to mouse TCRα constant genes and enhancers. The junctional nucleic acid sequences (SEQ ID NOs: 8 and 9) for the MAID 1769 targeting vector are described in Table 2.

Figure 4F:
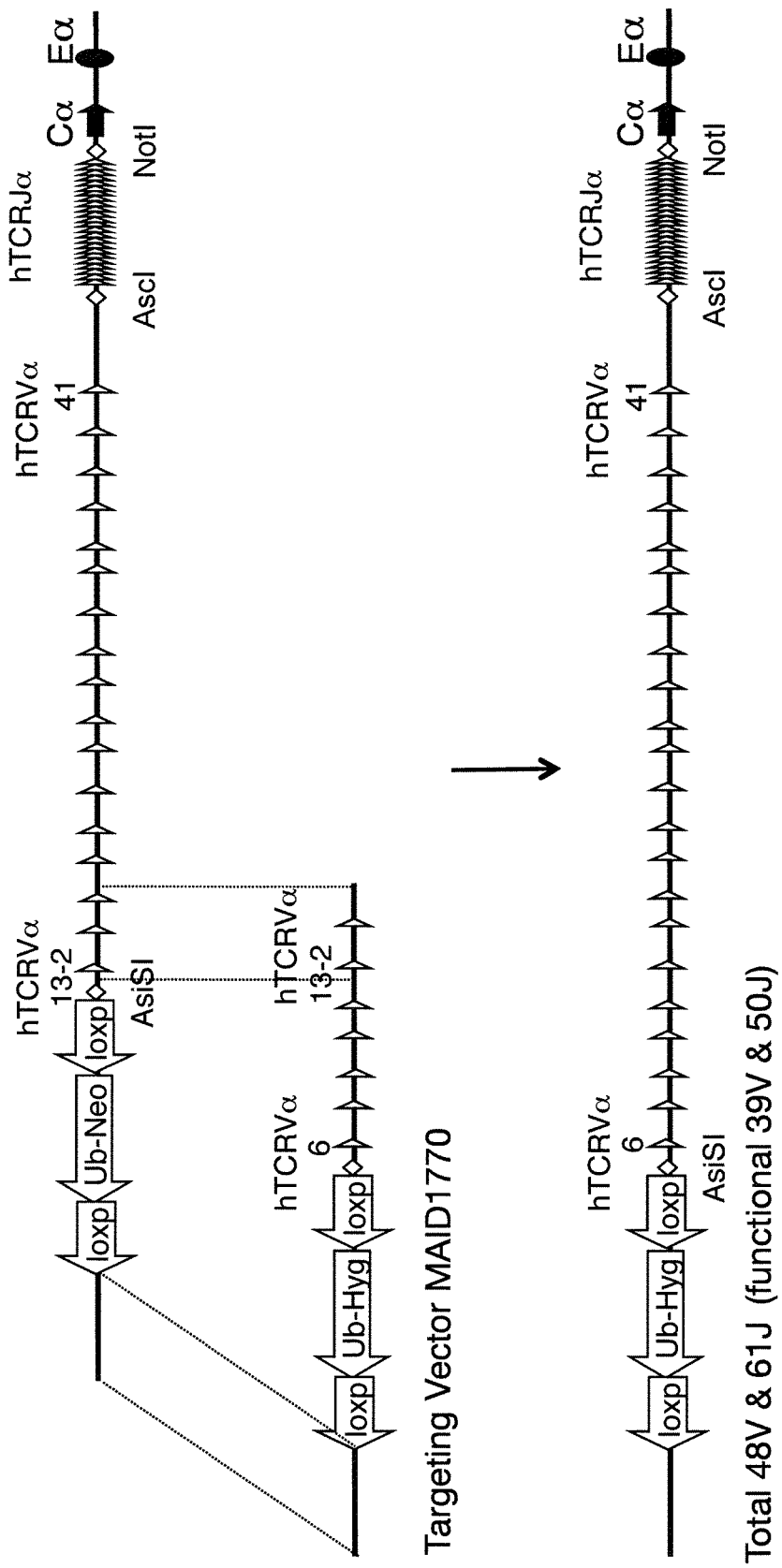

To generate a human TCRα mini-locus containing total of 48 human TCRαV (39 functional) and 61 human TCRαJ gene segments, DNA from human BAC clone RP11-92F11 (Invitrogen) was modified by homologous recombination and used as a targeting vector (MAID 1770) (FIG. 4F). This added 145,505 bp of human DNA that contained the next 13 (11 functional) consecutive human TCRαJ gene segments (TRAV6 to TRAV8.5) and a 5' loxp-ub-hygromycin-loxP cassette. Resulting TCRα locus contains a 5' loxp-ub-hygromycin-loxP cassette plus a total of 48 human TCRαV (39 functional) and 61 human TCRαJ gene segments operably linked to mouse TCRa constant genes and enhancers. The junctional nucleic acid sequences (SEQ ID NOs: 10 and 11) for the MAID 1770 targeting vector are described in Table 2.

Figure 4G:
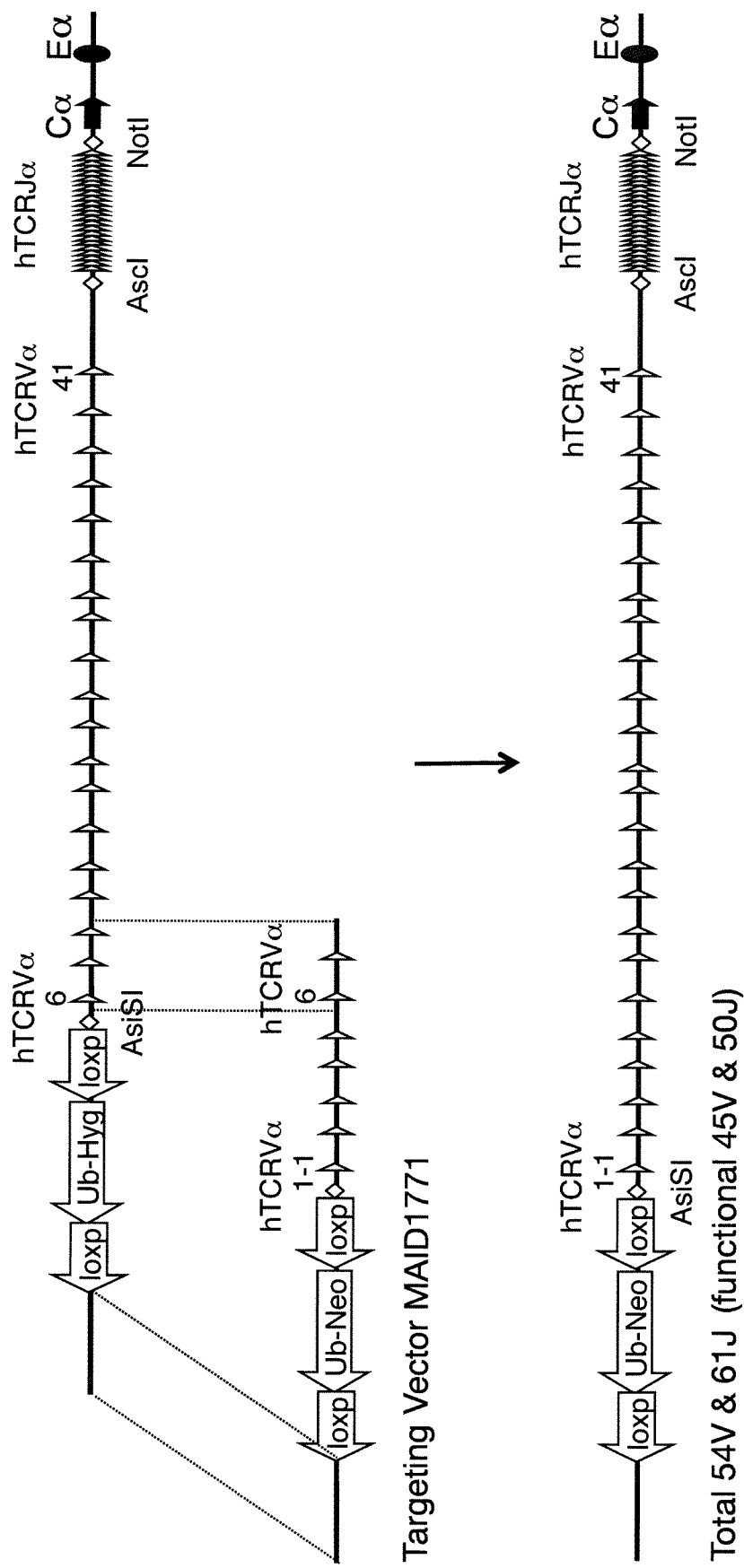

To generate a human TCRα mini-locus containing total of 54 human TCRαV (45 functional) and 61 human TCRαJ gene segments, DNA from human BAC clone RP11-780M2 (Invitrogen) was modified by homologous recombination and used as a targeting vector (MAID 1771) (FIG. 4G). This added 148,496 bp of human DNA that contained the next 6 (6 functional) consecutive human TCRαV gene segments (TRAV1-1 to TRAV5) and a 5' loxp-ub-neomycin-loxP cassette. Resulting TCRα locus contains a 5' loxp-ub-neomycin-loxP cassette plus a total of 54 human TCRαV (45 functional) and 61 human TCRαJ gene segment operably linked to mouse TCRα constant genes and enhancers. The junctional nucleic acid sequences (SEQ ID NOs: 12 and 13) for the MAID 1771 targeting vector are described in Table 2.

In any of the above steps, the selection cassettes are removed by deletion with Cre or Flp recombinase. In addition, human TCRδ locus may be introduced as depicted in FIG. 5.

Example 3

Figure 7:
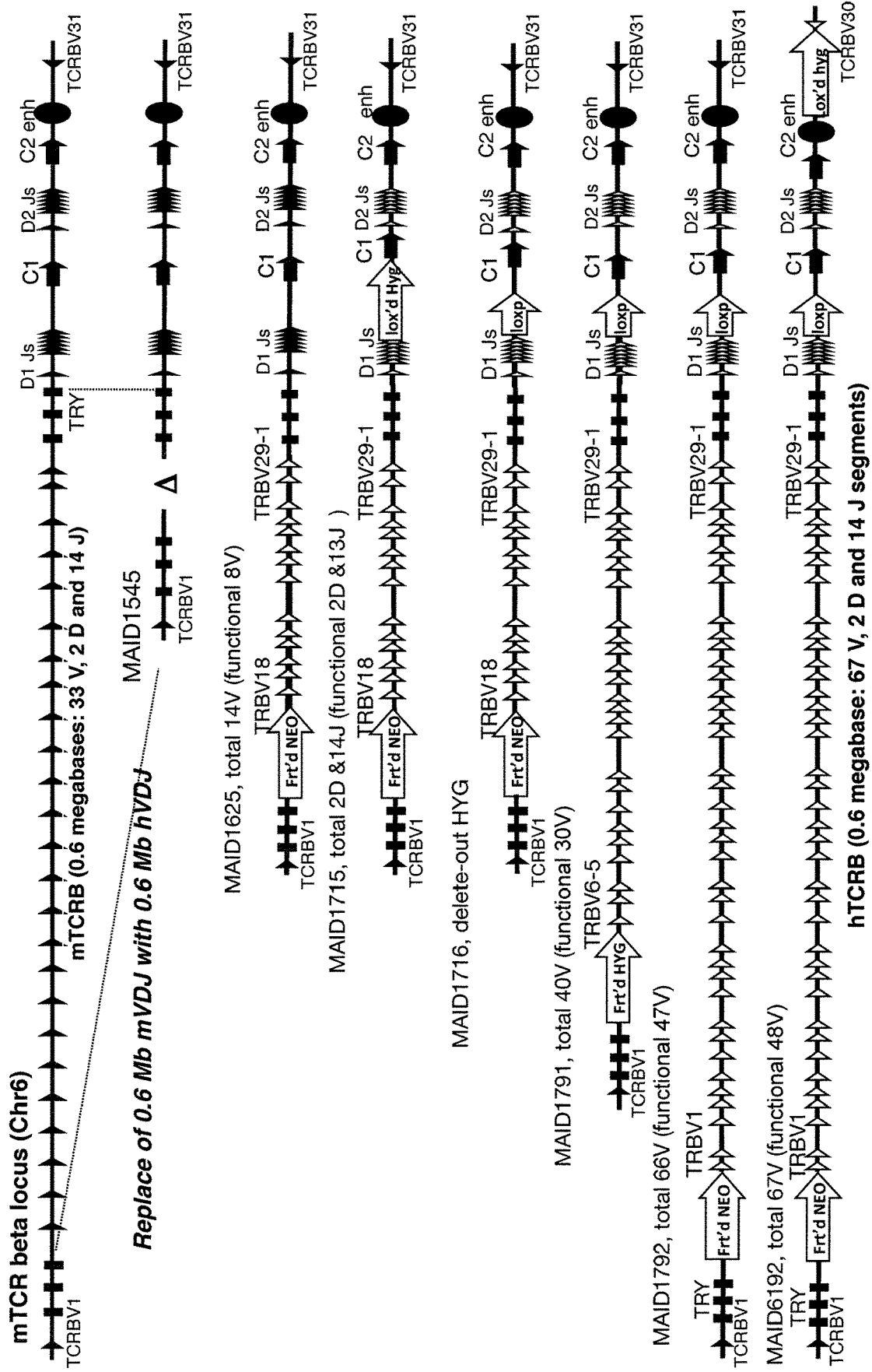
FIG. 7 depicts (not to scale) a progressive strategy for humanization of the mouse TCRβ locus, wherein TCRβ variable region gene segments are sequentially added to a deleted mouse TCRβ variable locus. Mouse sequence is indicated by closed symbols; human sequence is indicated by open symbols. MAID refers to modified allele ID number. TRBV or TCRBV=TCRβ V segment.

Progressive Humanization of TCRβ Variable Locus 0.6 megabases of DNA at mouse TCRβ locus corresponding to 33 V, 2 D, and 14 J mouse segments were replaced with 0.6 megabases of DNA corresponding to 67 V, 2D, and 14 J segments of human TCRβ using a progressive humanization strategy summarized in FIGS. 6 and 7. Junctional nucleic acid sequences of various targeting vectors used for progressive humanization strategy of TCRβ locus are summarized in Table 3, and included in the Sequence Listing.

TABLE 3

Junctional Nucleic Acid Sequences for Various TCRβ Locus Targeting Vectors

| MAID NO. | SEQ ID NO | Description |
|---|---|---|
| 1625 | 14 | Junctional nucleic acid sequence between the 3' end of mouse sequence upstream of the TCRβ variable locus (nearby the upstream mouse trypsinogen genes) and the 5' end of frt-Ub-Neo-frt cassette. |
| | 15 | Junctional nucleic acid sequence between the 3' end of frt-Ub-Neo-frt cassette and the 5' end of human TCRVβ18-TCRVβ29-1 insertion. |

TABLE 3-continued

Junctional Nucleic Acid Sequences for Various TCRβ Locus Targeting Vectors

| MAID NO. | SEQ ID NO | Description |
|---|---|---|
|  | 16 | Junctional nucleic acid sequence between the 3' end of human TCRVβ18-TCRVβ29-1 insertion and the 5' end of the mouse sequence downstream of the mouse TCRVβ segments (nearby downstream mouse trypsinogen genes). |
| 1715 | 17 | Junctional nucleic acid sequence between 3' of the downstream mouse trypsinogen genes and the 5' end of human TCRDβ1-TCRJβ1-1-TCRJβ1-6 insertion, including Iceul site. |
|  | 18 | Junctional nucleic acid sequence between the 3' end of human TCRDβ1-TCRJβ1-1-TCRJβ1-6 insertion and the 5' end of loxP-Ub-Hyg-loxP cassette. |
|  | 19 | Junctional nucleic acid sequence between the 3' end of loxP-Ub-Hyg-loxP cassette and the 5' end of mouse sequence nearby the mouse Cβ1 gene. |
|  | 20 | Junctional nucleic acid sequence between the 3' end of the mouse sequence nearby the mouse Cβ1 gene and the 5' end of human TCRDβ2-TCRJβ2-1-TCRJβ2-7 insertion, including NotI site. |
|  | 21 | Junctional nucleic acid sequence between the 3' end of human TCRDβ2-TCRJβ2-1-TCRJβ2-7 insertion and the 5' end of the mouse sequence downstream of the TCRβ variable locus (nearby the Cβ2 mouse sequence). |
| 1791 | 22 | Junctional nucleic acid sequence between the 3' end of mouse sequence upstream of the TCRβ variable locus (nearby the upstream mouse trypsinogen genes) and the 5' end of frt-Ub-Hyg-frt cassette. |
|  | 23 | Junctional nucleic acid sequence between the 3' end of frt-Ub-Hyg-frt cassette and the 5' end of human TCRVβ6-5-TCRVβ17 insertion. |
| 1792 | 24 | Junctional nucleic acid sequence between the 3' end of mouse sequence upstream of the TCRβ variable locus (nearby the upstream mouse trypsinogen genes) and the 5' end of frt-Ub-Neo-frt cassette. |
|  | 25 | Junctional nucleic acid sequence between the 3' end of frt-Ub-Hyg-frt cassette and the 5' end of human TCRVβ1-TCRVβ12-2 insertion. |
| 6192 | 26 | Junctional nucleic acid sequence between the 3' end of mouse sequence nearby the mouse Cβ2 gene and the 5' end of the human TCRBV30 exon 2 sequence. |
|  | 27 | Junctional nucleic acid sequence between the 3' end human TCRBV30 exon 1 sequence and the 5' end of mouse sequence downstream of TCRβ locus. |

Human TCRβ variable region segments are numbered as in IMGT database. At least 100 bp at each junction (about 50 bp from each end) are included in the Sequence Listing.

Figure 8A:
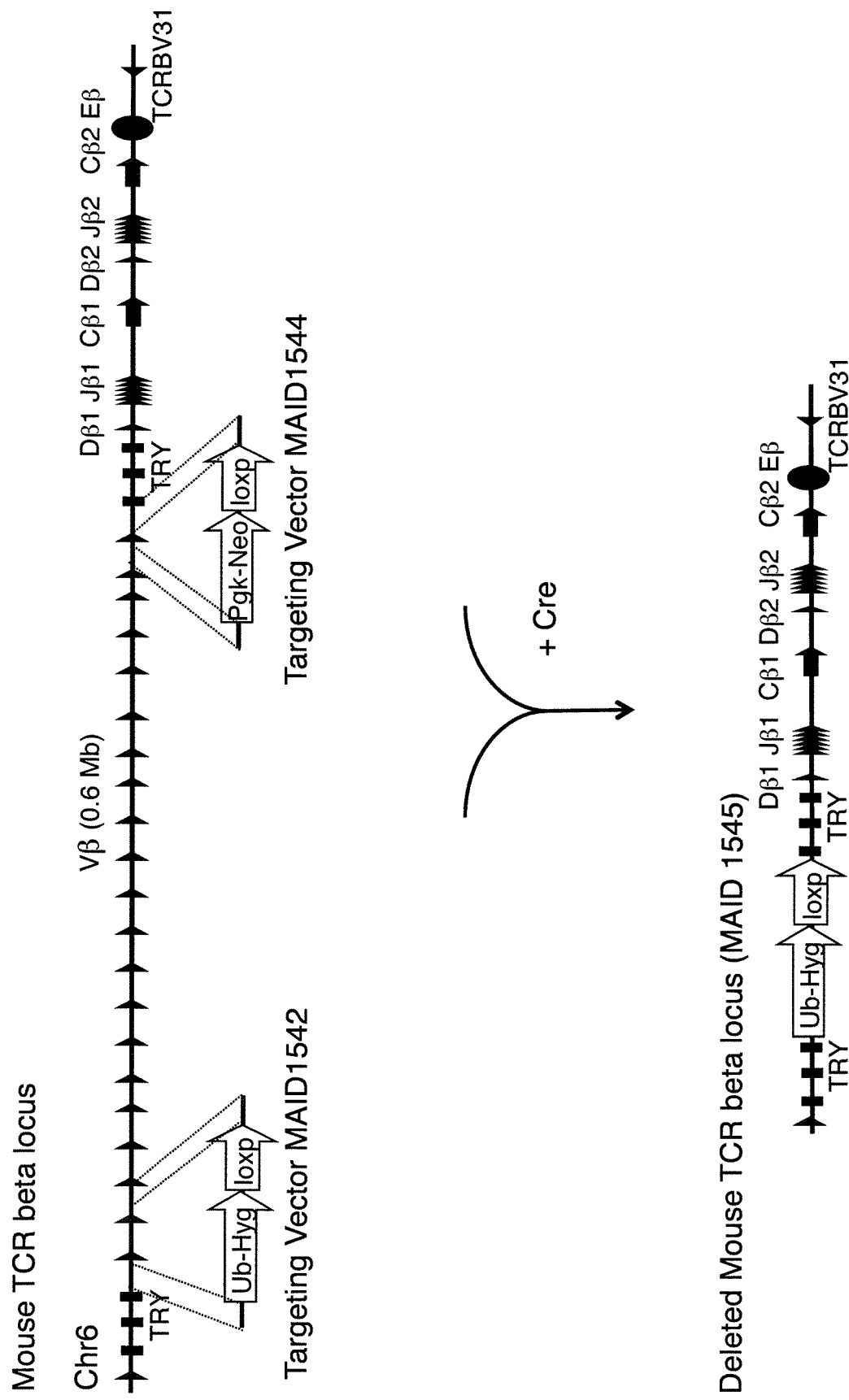
FIGS. 8A, 8B, 8C, 8D, 8E and 8F are a detailed depiction of progressive humanization strategy at the TCRβ locus.

Specifically, DNA from mouse BAC clone RP23-153p19 (Invitrogen) was modified by homologous recombination and used as a targeting vector (MAID 1544) to replace 17 kb region (including TCRBV30) just upstream of the 3' trypsinogen gene cluster in the endogenous mouse TCRβ locus with a PGK-neo cassette followed by a loxP site (FIG. 8A). DNA from mouse BAC clone RP23-461h15 (Invitrogen) was modified by homologous recombination and used as a targeting vector (MAID 1542) to replace 8355 bp region (including TCRBV2 and TCRBV3) downstream of 5' trypsinogen gene cluster in the endogenous mouse TCRβ locus with a Ub-hygromycin cassette followed by a loxP-site. ES cells bearing a double-targeted chromosome (i.e., a single endogenous mouse TCRβ locus targeted with both targeting vectors) were confirmed by karyotyping and screening methods (e.g., TAQMAN™) known in the art. Modified ES cells were treated with CRE recombinase, mediating the deletion of the region between the 5' and 3' loxP sites (consisting of the endogenous mouse TCRβ locus from TCRBV2 to TCRBV30) and leaving behind only a single loxP site, hygromycin cassette and the mouse TCRBDs, TCRBJs, constant, and enhancer sequences. One mouse TCRVβ was left upstream of the 5' cluster of trypsinogen genes, and one mouse TCRBβ was left downstream of the mouse Eβ, as noted in FIG. 8A.

Figure 8B:
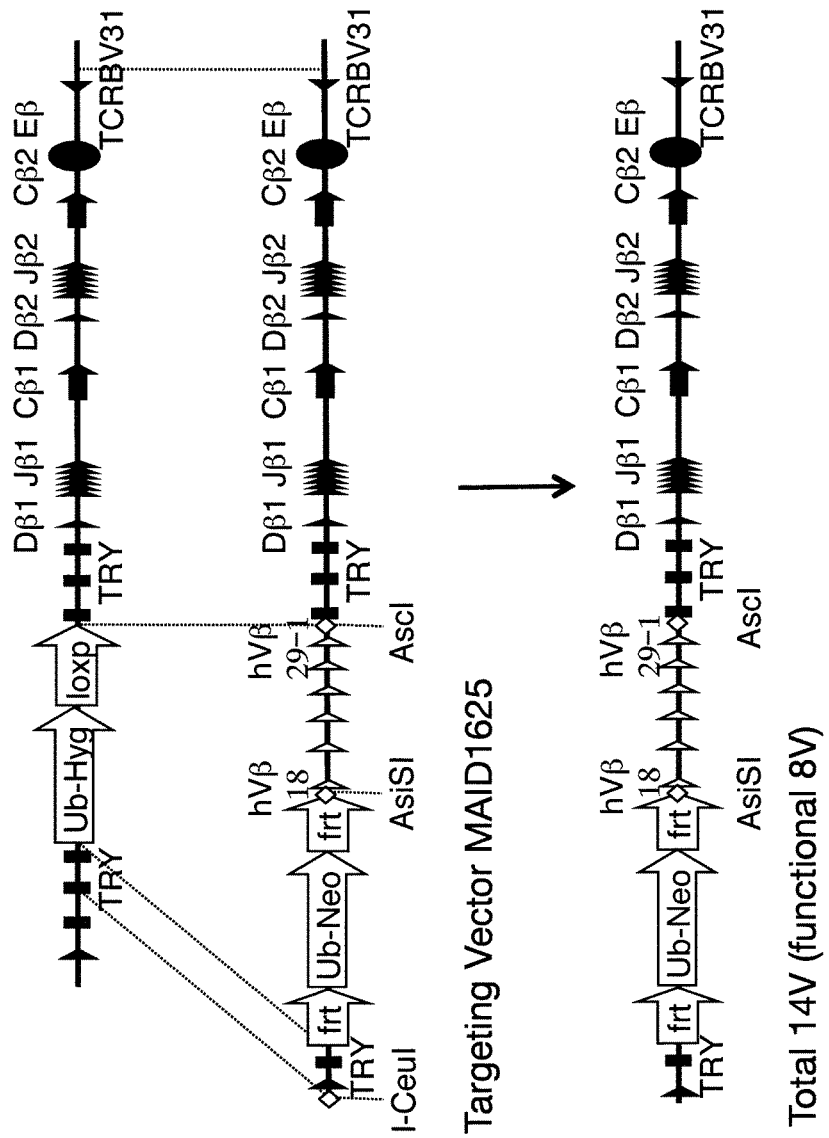
Figure 8C:
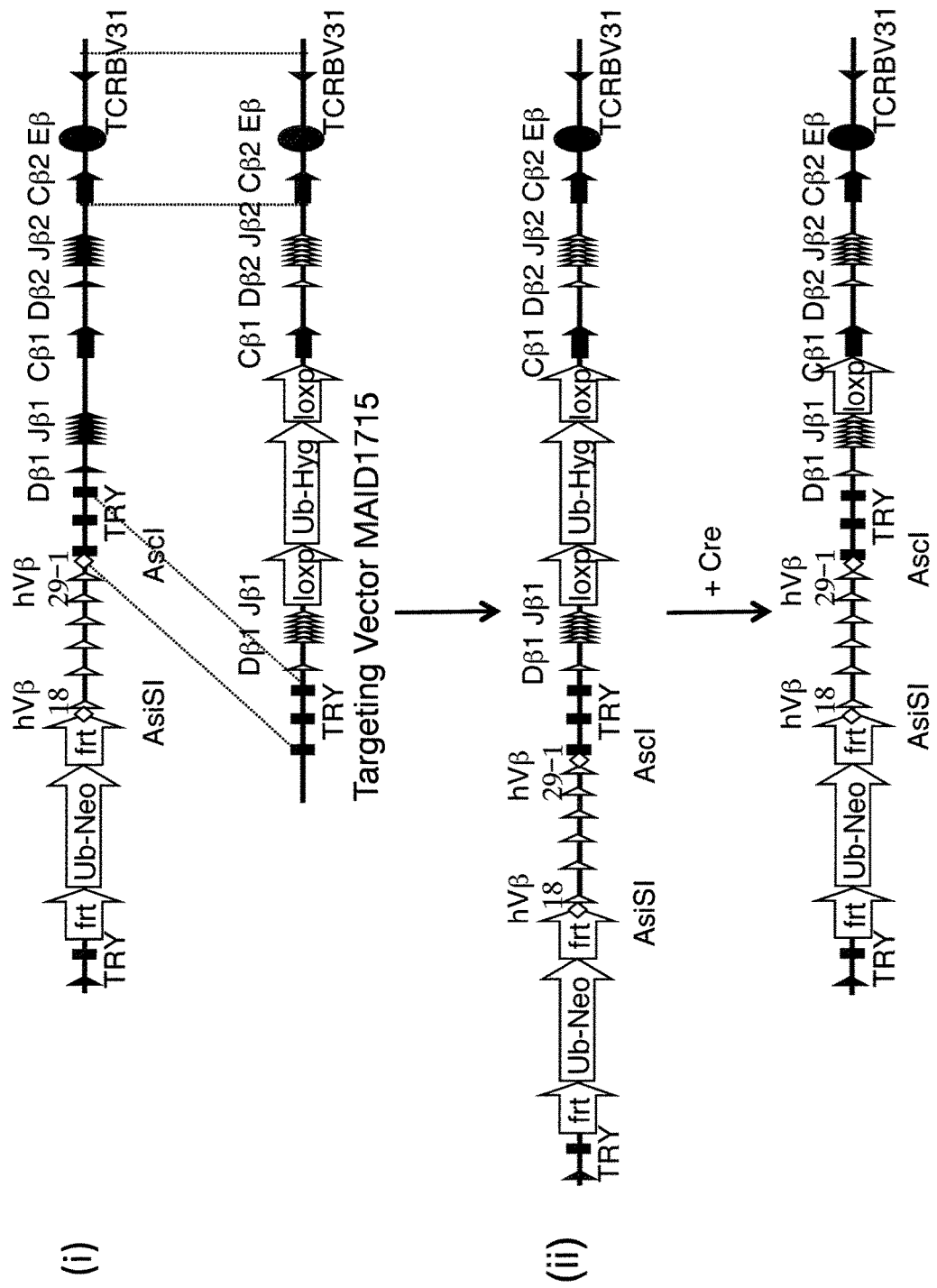

The first human targeting vector for TCRβ had 125,781 bp of human DNA from the CTD2559j2 BAC clone (Invitrogen) that contained the first 14 consecutive human TCRβV gene segments (TRBV18-TRBV29-1). This BAC was modified by homologous recombination to contain a 5' AsiSI site and a 3' AscI site for ligation of a 5' and 3' mouse homology arms. Two different homology arms were used for ligation to this human fragment: one set of homology arms contained endogenous TCRβ sequence surrounding the downstream mouse trypsinogen genes from the RP23-153p19 BAC clone and another set contained endogenous TCRβ sequence surrounding the upstream mouse trypsinogen genes from mouse BAC clone RP23-461 h15. This mouse-human chimeric BAC was used as a targeting vector (MAID 1625) for making an initial insertion of human TCRβ gene segments plus an upstream frt-ub-neomycin-frt cassette at the mouse TCRβ locus, and resulted in a human TCRβ mini-locus containing 14 human (8 functional) TCRβV (FIG. 8B). The junctional nucleic acid sequences (SEQ ID NOs: 14-16) for the MAID 1625 targeting vector are described in Table 3.

In order to replace mouse TCRβ D and J segments with human TCRβ D and J segments, DNA from mouse BAC clone RP23-302p18 (Invitrogen) and from human BAC clone RP11-701 D14 (Invitrogen) was modified by homologous recombination and used as a targeting vector (MAID 1715) into the ES cells that contained the TCRβV mini-locus described above (i.e., MAID 1625). This modification replaced ~18540 bp region (from 100 bp downstream of the polyA of the 3' trypsinogen genes to 100 bp downstream from the J segments in the D2 cluster which included mouse TCRBD1-J1, mouse constant 1, and mouse TCRBD2-J2) in the endogenous mouse TCRβ locus with ~25425 bp of sequence containing human TCRBD1-J1, loxP Ub-hygromycin-loxP cassette, mouse constant 1, human TCRBD2-J2 (FIG. 8C(i)). ES cells bearing a double-targeted chromosome (i.e., a single endogenous mouse TCRβ locus targeted with both targeting vectors) were confirmed by karyotyping and screening methods (e.g., TAQMAN™) known in the art. Modified ES cells were treated with CRE recombinase thereby mediating the deletion the hygromycin cassette leaving behind only a single loxP site downstream from human J segments in D1J cluster (FIG. 8C(ii)). The junctional nucleic acid sequences (SEQ ID NOs: 17-21) for the MAID 1715 targeting vector are described in Table 3.

Subsequently, a series of human targeting vectors were made that utilized the same mouse 5' arm that contained endogenous TCRβ sequence surrounding the upstream mouse trypsinogen genes from mouse BAC clone RP23-461h15 with alternating selection cassette.

Figure 8D:
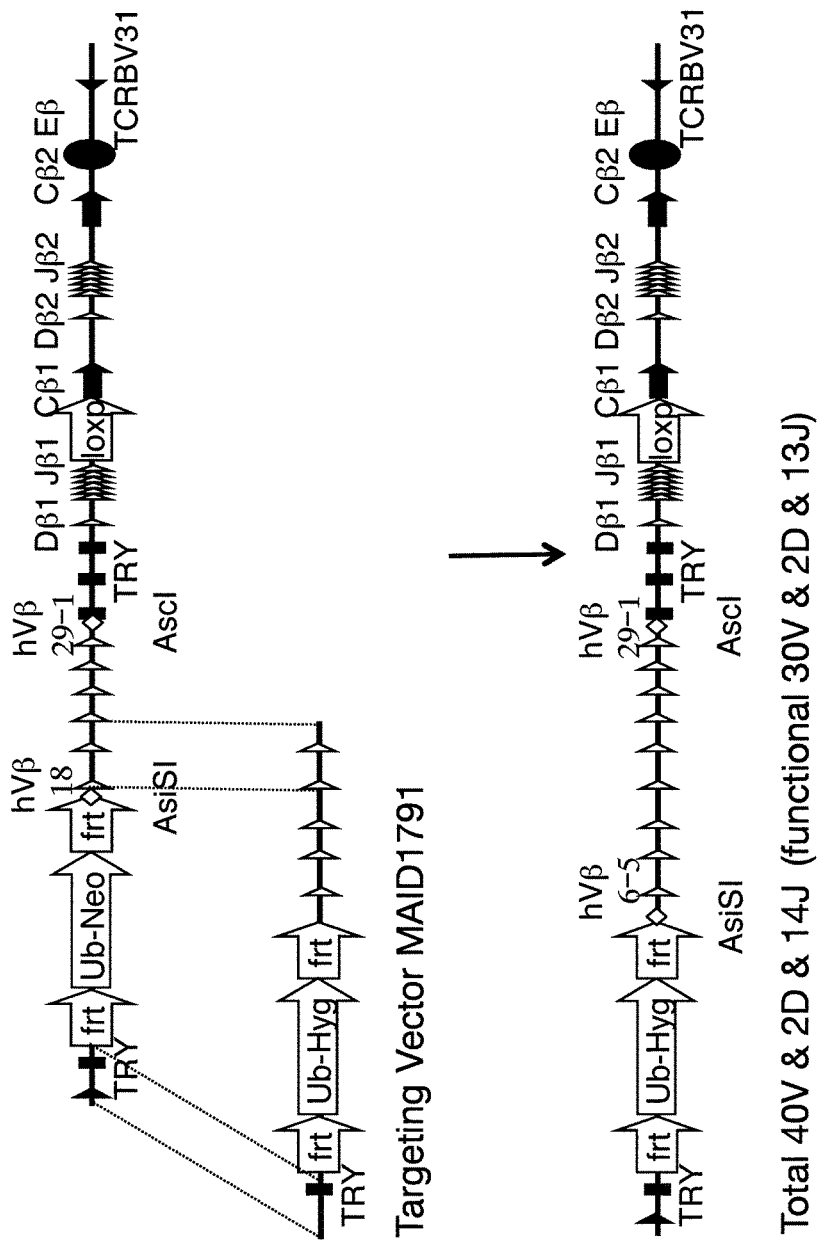

To generate a human TCRβ mini-locus containing a total 40 human TCRβ 3V (30 functional) and the human TCRβ D and J segments, DNA from human BAC clones RP11-134h14 and RP11-785k24 (Invitrogen) was modified by homologous recombination and combined into a targeting vector (MAID 1791) using standard bacterial homologous recombination, restriction digestion/ligation, and other cloning techniques. Introduction of the MAID 1791 targeting vector resulted in addition of 198,172 bp of human DNA that contained the next 26 (22 functional) consecutive human TCRβ V gene segments (TRBV6-5 to TRBV17) and a 5' frt-ub-hygromycin-frt cassette. Resulting TCRβ locus contained a 5' frt-ub-hygromycin-frt cassette plus a total of 40 human TCRβV (30 functional) and human TCRβ D and J gene segments operably linked to mouse TCRβ constant genes and enhancers (FIG. 8D). The junctional nucleic acid sequences (SEQ ID NOs: 22 and 23) for the MAID 1791 targeting vector are described in Table 3.

Figure 8E:
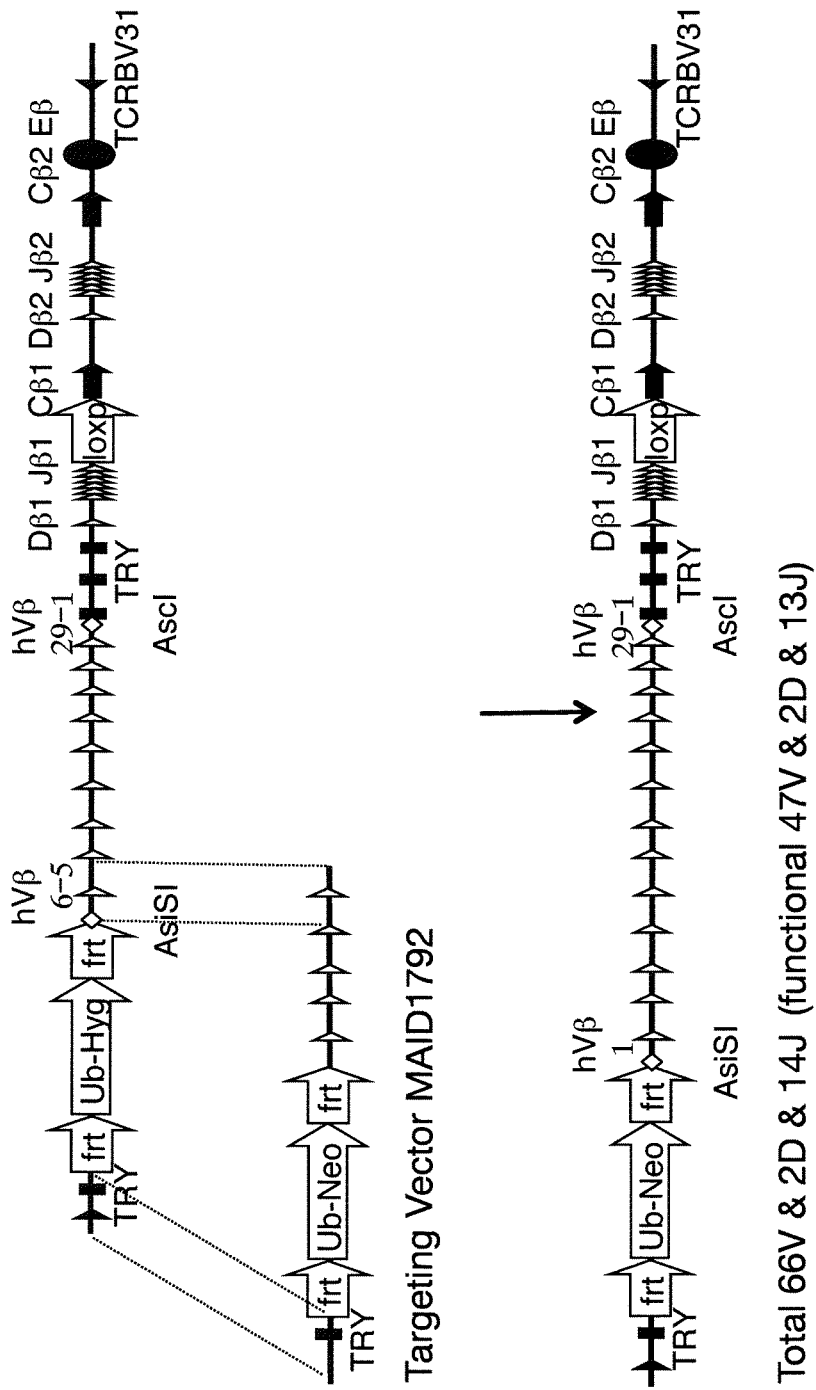

To generate a human TCRβ mini-locus containing a total 66 human TCRβV (47 functional) and the human TCRβ D and J segments, DNA from human BAC clone RP11-902B7 (Invitrogen) was modified by homologous recombination and used as a targeting vector (MAID 1792). This resulted in addition of 159,742 bp of human DNA that contained the next 26 (17 functional) consecutive human TCRβ V gene segments (TRBV1 to TRBV12-2) and a 5' frt-ub-neomycin-frt cassette. Resulting TCRβ locus contained a 5' frt-ub-neomycin-frt cassette plus a total of 66 human TCRβV (47 functional) and human TCRβ D and J gene segments operably linked to mouse TCRβ constant genes and enhancers. (FIG. 8E). The junctional nucleic acid sequences (SEQ ID NOs: 24 and 25) for the MAID 1792 targeting vector are described in Table 3.

In any of the above steps, the selection cassettes are removed by deletion with Cre or Flp recombinase. For example, as depicted in FIG. 7, MAID 1716 corresponds to MAID 1715 with the hygromycin cassette deletion.

Finally, a human TCRβ mini-locus containing a total 67 human TCRβV (48 functional) and the human TCRβ D and J segments was generated. Mouse TCRBV31 is located ~9.4 kb 3' of TCRBC2 (second TCRB constant region sequence) and is in the opposite orientation to the other TCRBV segments. The equivalent human V segment is TCRBV30, which is located in a similar position in the human TCRβ locus.

Figure 8F:
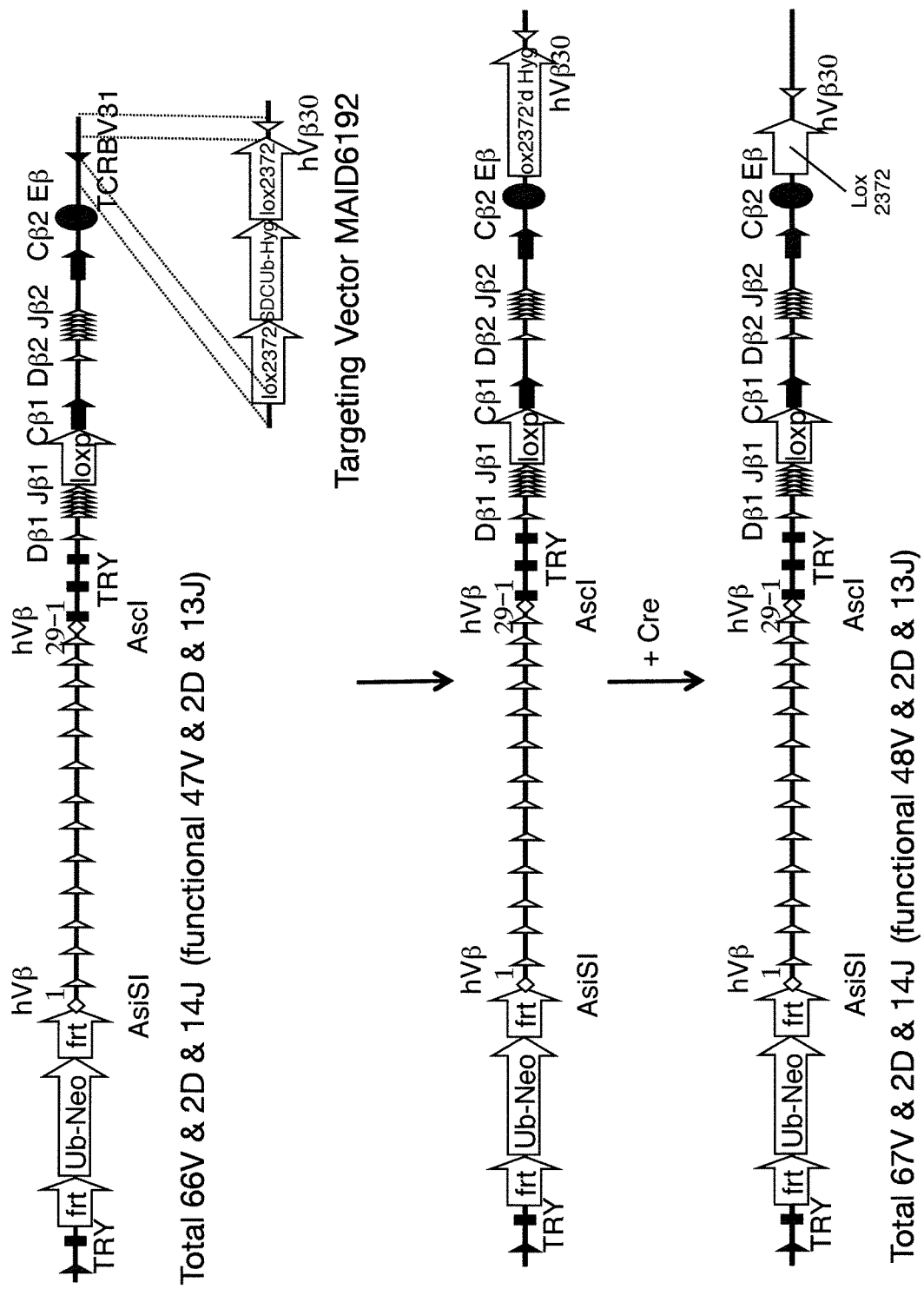

To humanize TCRBV31, the mouse BAC clone containing mouse TCRBV31, was modified by bacterial homologous recombination to make LTVEC MAID 6192 (FIG. 8F). The entire coding region, beginning at the start codon in exon 1, the intron, the 3' UTR, and the recombination signal sequences (RSS) of TCRBV31 were replaced with the homologous human TCRBV30 sequences. The 5' UTR was kept as mouse sequence. For selection, a self-deleting cassette (lox2372-Ubiquitin promoter-Hyg-PGKpolyA-Protamine promoter-Cre-SV40polyA-lox2372) was inserted in the intron (72 bp 3' of exon 1,289 bp 5' of exon 2). For simplicity, FIGS. 7 and 8 depict the selection cassette 3' of the hTCRBV30, while it was engineered to be located in the intron between exon 1 and exon 2 of the hTCRBV30 gene. The protamine promoter driving Cre expression is transcribed exclusively in post-meiotic spermatids, so the cassette is "self-deleted" in the F1 generation of mice.

The junctional nucleic acid sequences (SEQ ID NOs: 26 and 27) for the MAID 6192 targeting vector are described in Table 3. MAID 6192 DNA is electroporated into MAID1792 ES cells. ES cell clones are selected for hygromycin-resistance and screened for loss of mouse TCRB31 allele and gain of human TCRB30 allele.

Similar engineering strategy is used to optionally delete the remaining 5' mouse TCRβ V segment.

Example 4

Generation of TCRα/TCRβ Mice

At each step of progressive humanization of TCRα and TCRβ loci, mice homozygous for humanized TCRα variable locus may be bred with mice homozygous for humanized TCRβ variable locus to form progeny comprising humanized TCRα and TCRβ variable loci. Progeny are bred to homozygosity with respect to humanized TCRα and humanized TCRβ loci.

In one embodiment, mice homozygous for humanized TCRα variable locus comprising 8 human Vα and 61 human Jα (MAID 1767; "1767 HO") were bred with mice homozygous for humanized TCRβ variable locus comprising 14 human Vβ, 2 human Dβ, and 14 human Jβ (MAID 1716; "1716 HO"). Progeny were bred to homozygosity with respect to both humanized loci.

Example 5

Splenic T Cell Production in Mice Homozygous for Humanized TCRα and/or TCRβ Locus Spleens from wild type (WT) mice; mice with deleted mouse TCRα locus ("MAID1540", see FIG. 3); mice homozygous for human TCRα locus ("MAID 1767", see FIG. 3); mice with deleted TCRβ V segments with the exception of two remaining mouse V segments ("MAID1545", see FIG. 7); mice homozygous for human TCRβ locus, also comprising the two remaining mouse V segments ("MAID 1716", see FIG. 7); and mice homozygous for both human TCRα and TCRβ loci, with TCRβ locus also comprising the two remaining mouse V segments ("MAID 1767 1716") were perfused with Collagenase D (Roche Bioscience) and erythrocytes were lysed with ACK lysis buffer, followed by washing in RPMI medium.

Splenocytes from a single WT, MAID 1540, 1767, 1545, 1716, and 1716 1767 representative animal were evaluated by flow cytometry. Briefly, cell suspensions were made using standard methods. 1×10$^6$ cells were incubated with anti-mouse CD16/CD32 (2.4G2, BD) on ice for 10 minutes stained with the appropriate cocktail of antibodies for 30 minutes on ice. Following staining, cells were washed and then fixed in 2% formaldehyde. Data acquisition was performed on an LSRII/CantoII/LSRFortessa flow cytometer and analyzed with FlowJo.

Figure 9:
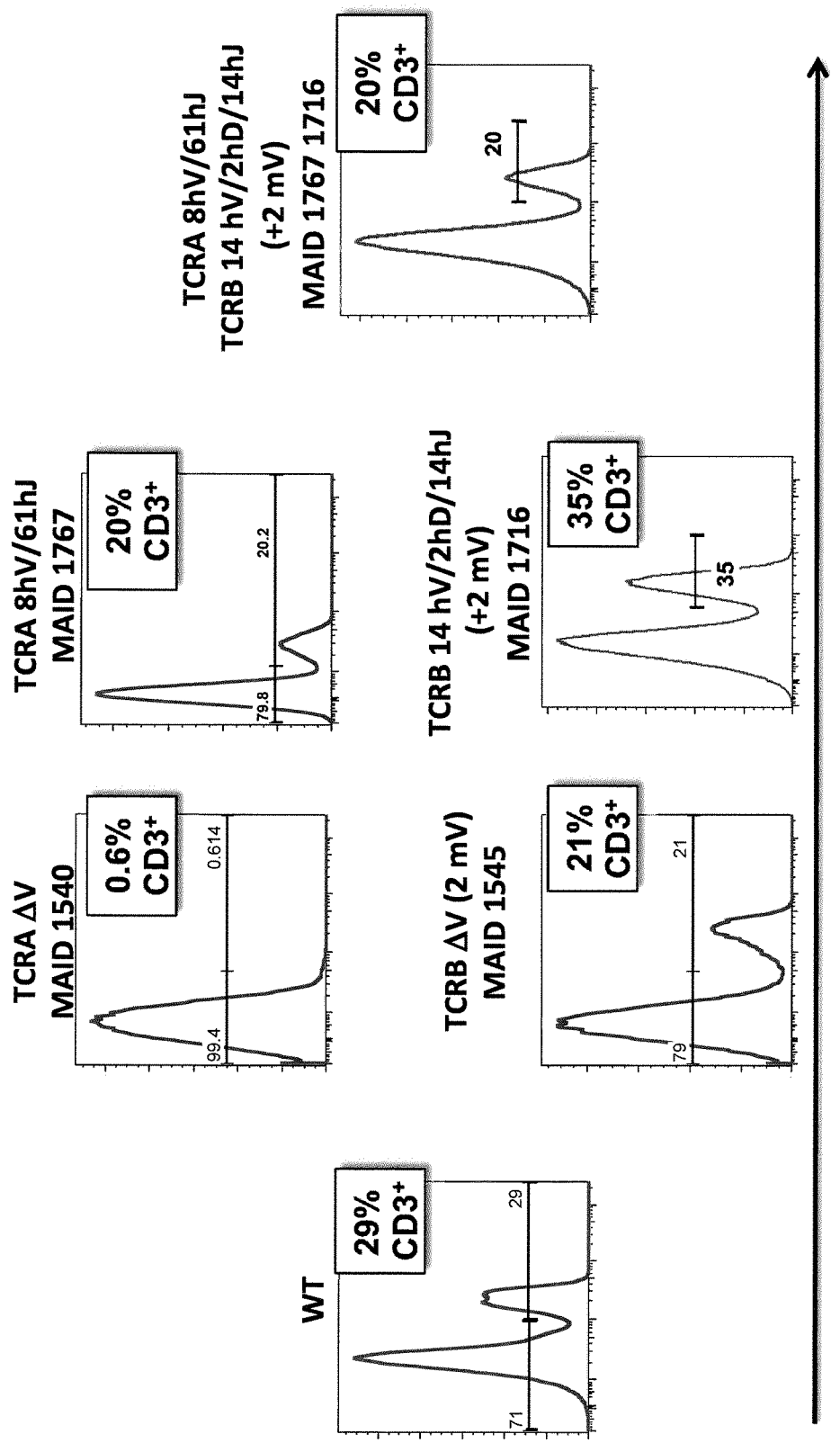
FIG. 9 depicts representative FACS analysis histograms for percent spleen cells (where Y axis is number of cells, X axis is mean fluorescence intensity, and the gate shows frequency of CD3+ T cells within the single lymphocyte population) stained with anti-CD3 antibody in a wild type (WT) mouse; a mouse homozygous for a deleted TCRα locus (first top panel; MAID 1540 of FIG. 3); a mouse homozygous for a deleted TCRα locus and comprising 8 human Vα and 61 human Jα segments (second top panel; MAID 1767 of FIG. 3 or a humanized TCRα mouse); a mouse homozygous for a deleted TCRβ locus with the exception of one upstream and one downstream mouse Vβ segments (first bottom panel; MAID 1545 of FIG. 7); a mouse homozygous for a deleted TCRβ locus with one upstream and one downstream mouse Vβ segments and comprising 14 human Vβ, 2 human Dβ, and 14 human Jβ segments (second bottom panel; MAID 1716 of FIG. 7 or a humanized TCRβ mouse); and a mouse homozygous for both TCRα and TCRβ loci deletions (with the exception of said two mouse Vβ segments) and comprising 8 human Vα and 61 human Jα segments at the endogenous TCRα locus as well as 14 human Vβ, 2 human Dβ, and 14 human Jβ segments at the endogenous TCRβ loci (MAID 1767/1716 or a humanized TCRα/β (mouse).

For staining of splenocytes, anti-mouse FITC-CD3 (17A2, BD) was used. As demonstrated in FIG. 9, mice with human TCR segments were able to produce significant numbers of CD3+ T cells, while mice with TCRα mouse locus deletion did not. Mice with TCRβ locus deletion also produced CD3+ T cells, presumably due to utilization of the remaining 3' mouse V segment (see below).

Example 6

Thymic T Cell Development in Mice Homozygous for Humanized TCRα and/or TCRβ Locus To determine whether mice homozygous for humanized TCRα and/or TCRβ locus exhibited normal T cell development in the thymus, splenocytes from four of each WT, 1767 HO, 1716 HO, and 1716 HO 1767 HO age matched animals (7-10 weeks old) were used in flow cytometry to evaluate production of T cells at various developmental stages, as well as to evaluate frequency and absolute number of each of DN, DP, CD4 SP, and CD8 SP T cells.

Cell type determinations were made based on the presence of CD4, CD8, CD44, and CD25 cell surface markers as summarized in Table 1. Correlation between cell type designation and expression of cell surface markers in the thymus is as follows: double negative (DN) cells (CD4– CD8–), double positive (DP) cells (CD4+ CD8+), CD4 single positive cells (CD4+ CD8–), CD8 single positive cells (CD4– CD8+), double negative 1/DN1 cells (CD4– CD8–, CD25– CD44+), double negative 2/DN2 cells (CD4– CD8–, CD25+ CD44+), double negative 3/DN3 cells (CD4– CD8–, CD25+ CD44–), double negative 4/DN4 cells (CD4– CD8–, CD25– CD44–).

Thymocytes were evaluated by flow cytometry. Briefly, cell suspensions were made using standard methods. Flow cytometry was conducted as described in Example 5. Antibodies used were: anti-mouse PE-CD44 (IM7, BioLegend), PeCy7-CD25 (PC61, BioLegend), APC-H7-CD8a (53-6.7, BD), and APC-CD4 (GK1.5, eBioscience).

Figure 10:
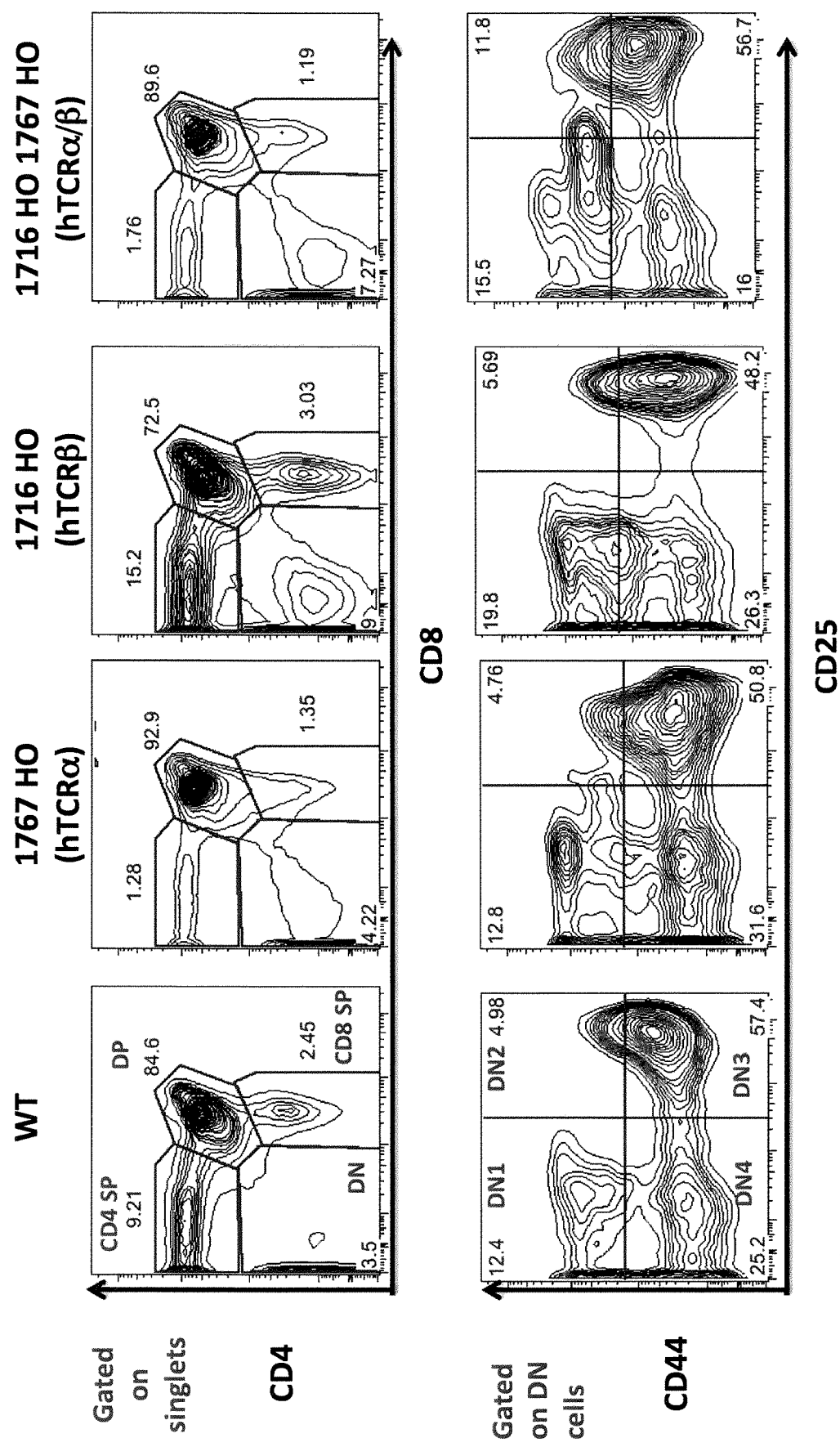
FIG. 10 is a representative FACS contour plot of mouse thymus cells from a WT, homozygous humanized TCRα (1767 HO; hTCRα); homozygous humanized TCRβ (1716 HO; hTCRβ); and homozygous humanized TCRα/β mouse (1716 HO 1767 HO; hTCRα/β) stained with anti-CD4 (Y axis) and anti-CD8 (X axis) antibodies (top panel), and anti-CD44 (Y axis) and anti-CD25 (X axis) antibodies (bottom panel). The FACS plot in the top panel allows to distinguish double negative (DN), double positive (DP), CD4 single positive (CD4 SP), and CD8 single positive (SP CD8) T cells. The FACS plot in the bottom panel allows to distinguish various stages of double negative T cells during T cell development (DN1, DN2, DN3, and DN4). 1716 and 1767 refer to MAID numbers as identified in FIGS. 3 and 7.
Figure 11:
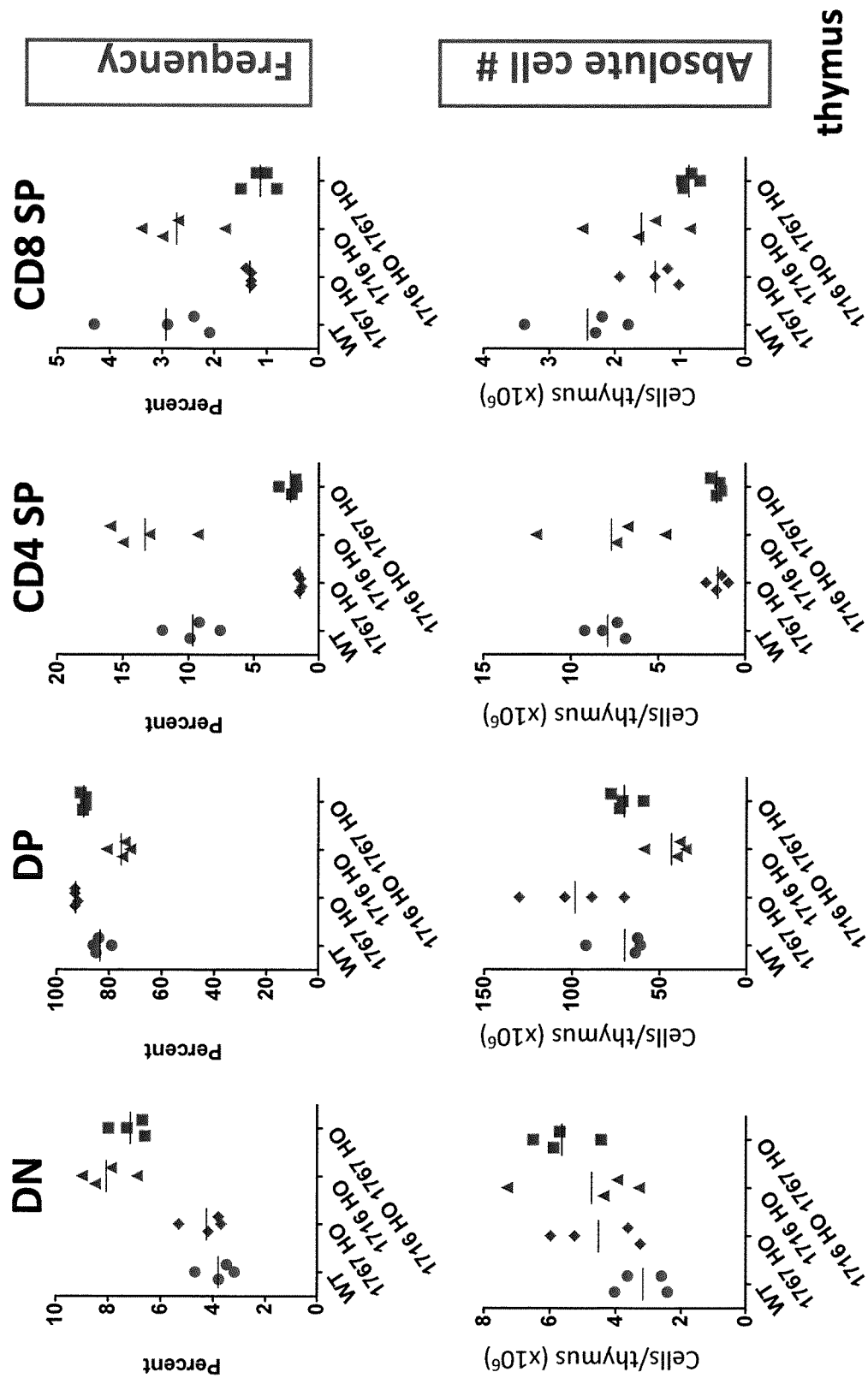
FIG. 11 demonstrates either frequency (top panel) or absolute number (bottom panel) of DN, DP, CD4 SP, and CD SP T cells in the thymus of either WT, hTCRα (1767 HO); hTCRβ (1716 HO); or hTCRα/β (1716 HO 1767 HO) mice (n=4).

As shown in FIGS. 10 and 11, mice homozygous for humanized TCRα, TCRβ, and both TCRα and TCRβ were able to produce a DN1, DN2, DN3, DN4, DP, CD4 SP, and CD8 SP T cells, indicating that the T cells produced from the humanized loci are capable of undergoing T cell development in the thymus.

Example 7

Splenic T Cell Differentiation in Mice Homozygous for Humanized TCRα and/or TCRβ Locus To determine whether mice homozygous for humanized TCRα and/or TCRβ locus exhibited normal T cell differentiation in the periphery (e.g., spleen), four of each WT, 1767 HO, 1716 HO, and 1716 HO 1767 HO age matched animals (7-10 weeks old) were used in flow cytometry to evaluate production of various T cell types in the spleen (CD3+, CD4+, CD8+, T naïve, Tcm, and Teff/em), as well as to evaluate the absolute number of each T cell type in the spleen.

Cell type determinations were made based on the presence of CD19 (B cell marker), CD3 (T cell marker), CD4, CD8, CD44, and CD62L (L-selectin) cell surface markers. Correlation between cell type designation and expression of cell surface markers in the spleen is as follows: T cells (CD3+), CD4 T cells (CD3+ CD4+ CD8–), CD8 T cells (CD3+ CD4–CD8+), CD4 effector/effector memory T cells (CD3+ CD4+ CD8–CD62L–CD44+), CD4 central memory T cells (CD3+ CD4+ CD8–CD62L+CD44+), CD4 naïve T cells (CD3+ CD4+ CD8–CD62L+CD44–), CD8 effector/effector memory T cells (CD3+ CD4–CD8+ CD62L–CD44+), CD8 central memory T cells (CD3+ CD4–CD8+ CD62L+CD44+), CD8 naïve T cells (CD3+ CD4–CD8+ CD62L+CD44–).

Splenocytes were evaluated by flow cytometry. Briefly, cell suspensions were made using standard methods. Flow cytometry was conducted as described in Example 5. Antibodies used were: anti-mouse FITC-CD3 (17A2, BD), PE-CD44 (IM7, BioLegend), PerCP-Cy5.5-CD62L (Mel-14, BioLegend), APC-H7-CD8a (53-6.7, BD), APC-CD4 (GK1.5, eBioscience), and V450-CD19 (1Dβ, BD).

Figure 12:
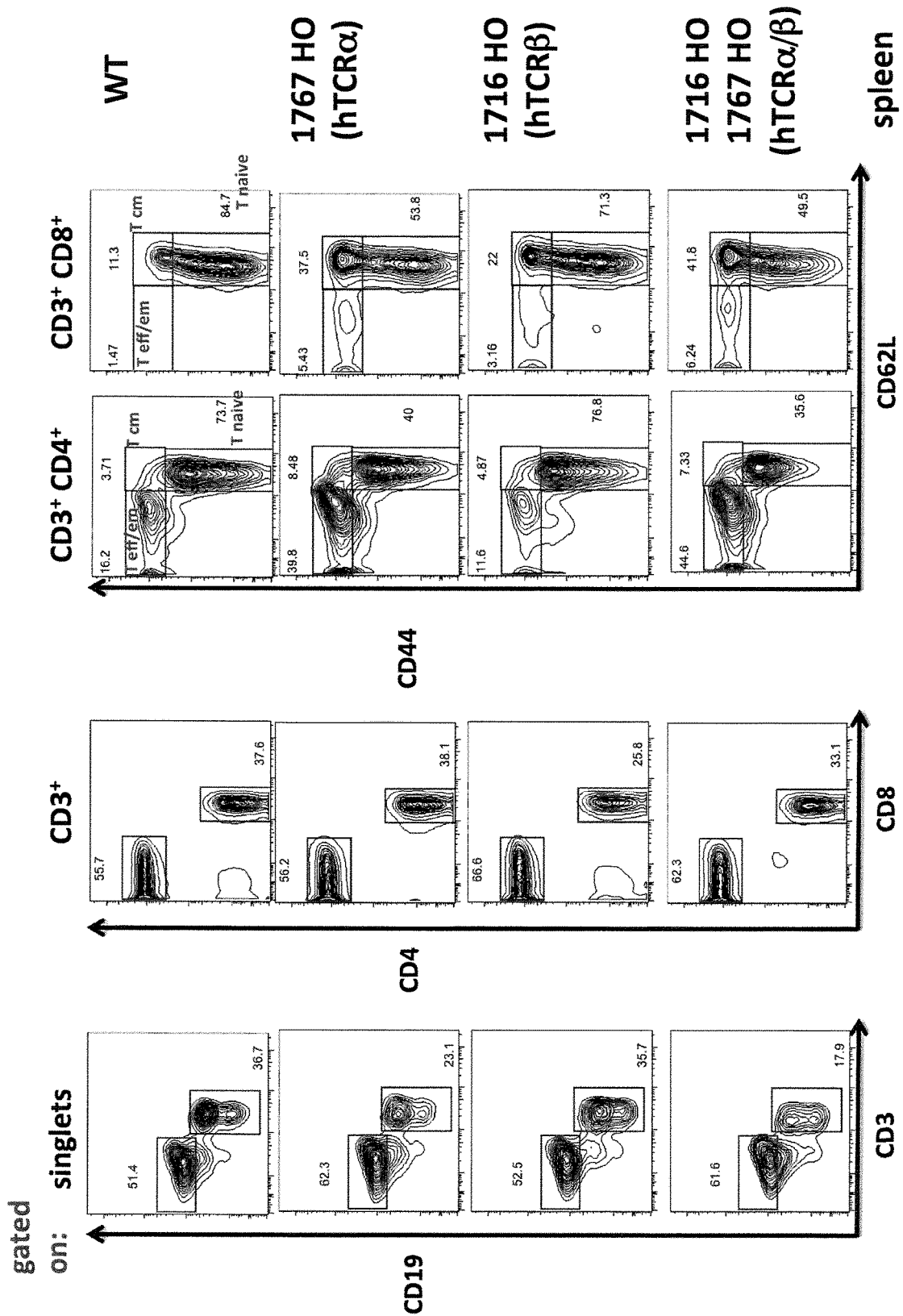
FIG. 12 is a representative FACS analysis of spleen cells of a WT, hTCRα (1767 HO); hTCRβ (1716 HO); or hTCRα/β (1716 HO 1767 HO) mouse: left panel represents analysis of singlet cells based anti-CD19 antibody (Y axis; stain for B lymphocytes) or anti-CD3 antibody (X axis; stain for T lymphocytes) staining; middle panel represents analysis of CD3+ cells based on anti-CD4 (Y axis) or anti-CD8 (X axis) antibody staining; and right panel represents analysis of either CD4+ or CD8+ cells based on anti-CD44 (Y axis) or anti-CD62L (X axis) antibody staining, the stains allow to distinguish various types of T cells in the periphery (naïve T cells vs. central memory T cells (Tcm) vs. effector or effector memory T cells (Teff/Tem)).
Figure 13:
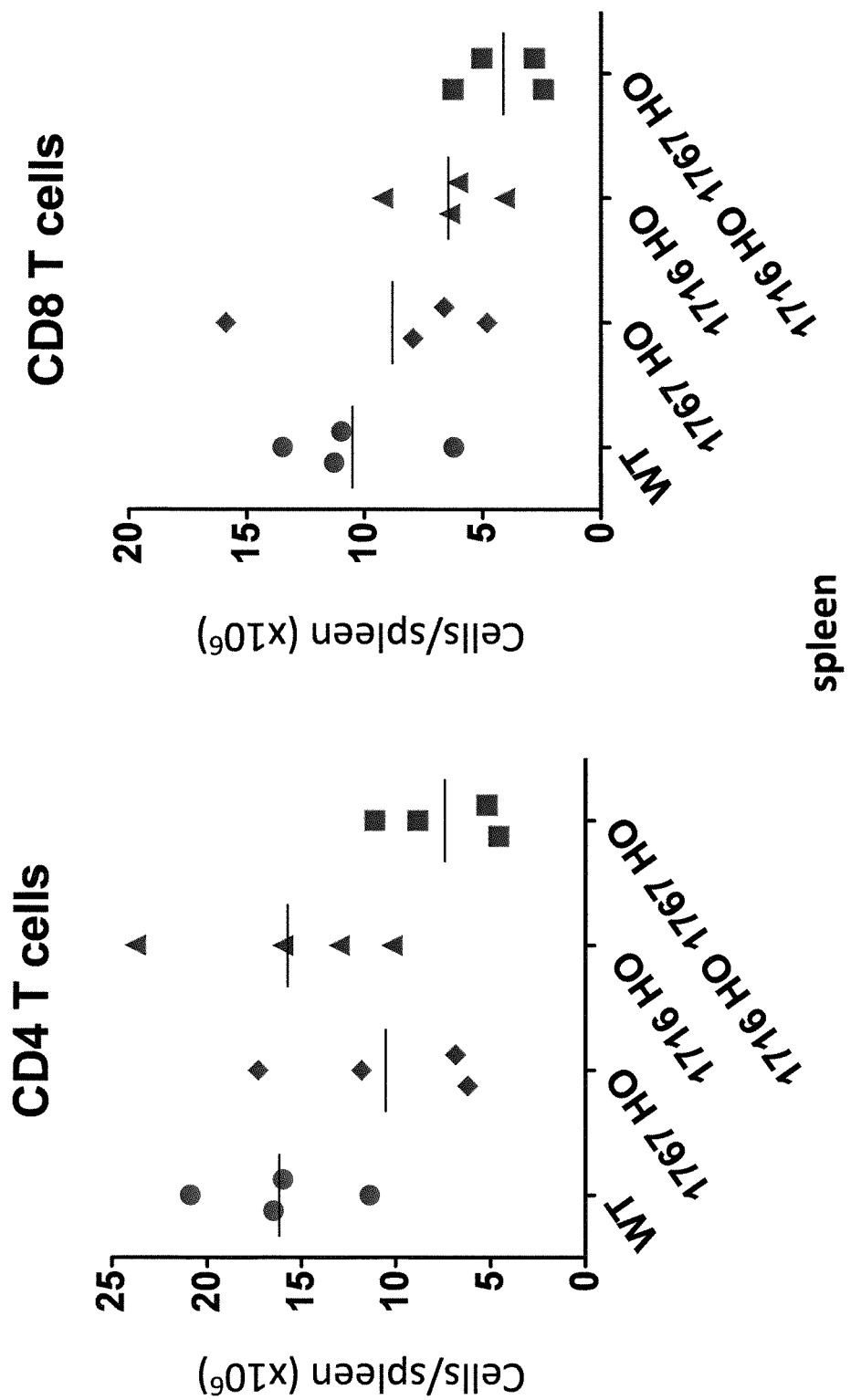
FIG. 13 demonstrates the number of CD4+ (left panel) or CD8+ (right panel) T cells per spleen (Y axes) of WT, hTCRα (1767 HO); hTCRβ (1716 HO); or hTCRα/β (1716 HO 1767 HO) mice (n=4).
Figure 14:
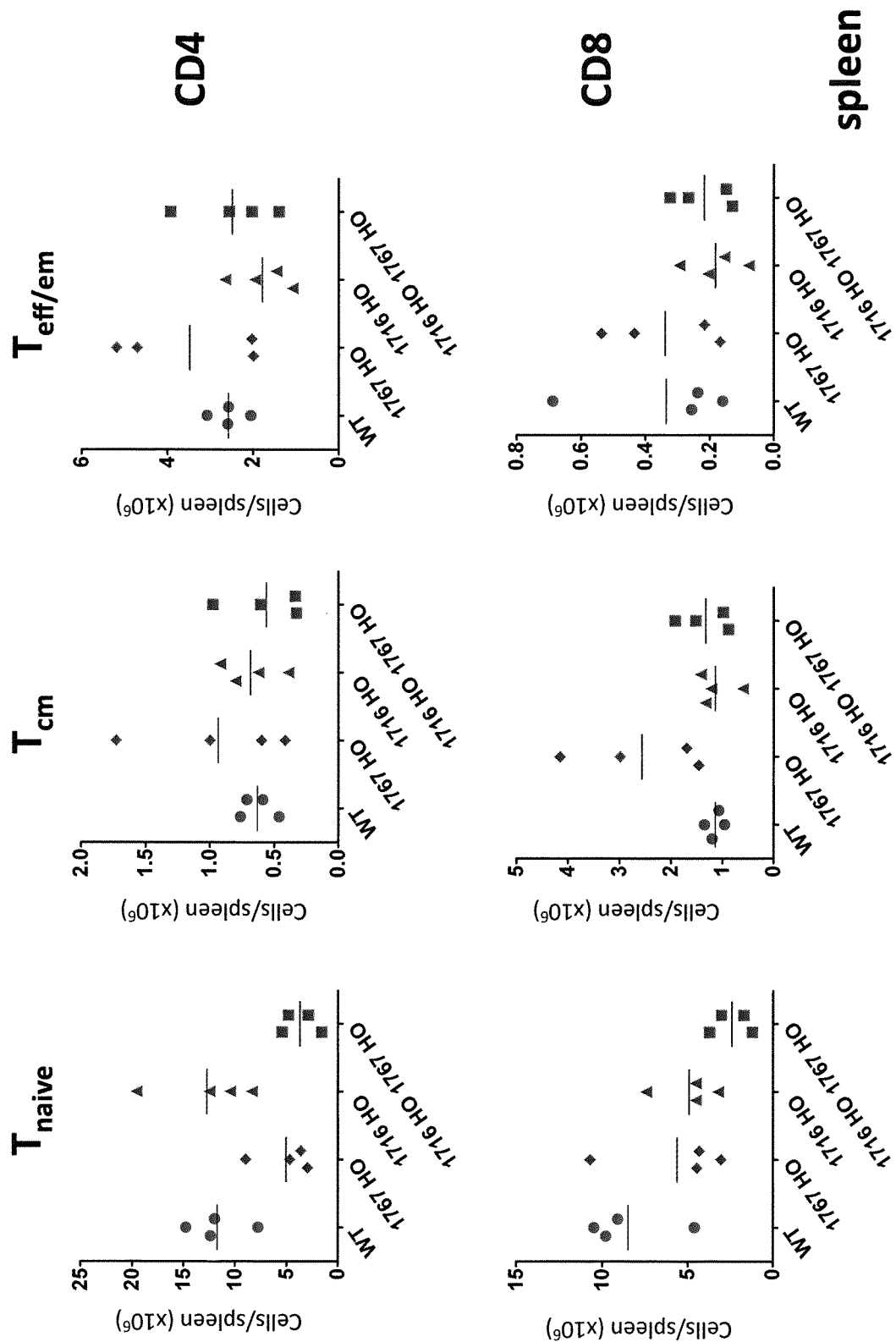
FIG. 14 demonstrates the number of T naïve, Tcm, and Teff/em cells per spleen (Y axes) of CD4+ (top panel) or CD8+ (bottom panel) T cells of WT, hTCRα (1767 HO); hTCRβ (1716 HO); or hTCRα/β (1716 HO 1767 HO) mice (n=4).

As shown in FIGS. 12-14, T cells in the spleen of mice homozygous for humanized TCRα, TCRβ, and both TCRα and TCRβ were able to undergo T cell differentiation, and both CD4+ and CD8+ T cells were present. In addition, memory T cells were detected in the spleens of the mice tested.

Example 8

Utilization of Human V Segments in Humanized TCR Mice

Expression of human TCRβ V segments was evaluated on protein and RNA level using flow cytometry and TAQMAN™ real-time PCR, respectively, in mice homozygous for humanized TCRβ locus (1716 HO) and mice homozygous for both humanized TCRβ and TCRα locus (1716 HO 1767 HO).

For flow cytometry, splenic T cell were prepared and analysis conducted as described in Example 5. For flow cytometry, TCRβ repertoire kit (IOTEST® Beta Mark, Beckman Coulter) was used. The kit contains anti-human antibodies specific for a number of human TCRBVs, e.g., hTRBV-18, -19, -20, -25, -27, -28, and -29.

Results are summarized in FIG. 15. The tables presented in FIG. 15A (CD8 T cell overlay) and FIG. 15B (CD4 T cell overlay) demonstrate that splenic T cells in both 1716 HO and 1716 HO 1767 HO mice utilized a number of human TCRβ V segments. The wild type mice were used as a negative control.

For real-time PCR, total RNA was purified from spleen and thymus using MAGMAX™-96 for Microarrays Total RNA Isolation Kit (Ambion by Life Technologies) according to manufacturer's specifications. Genomic DNA was removed using MAGMAX™TURBO™DNase Buffer and TURBO DNase from the MAGMAX kit listed above (Ambion by Life Technologies). mRNA (up to 2.5 ug) was reverse-transcribed into cDNA using SUPERSCRIPT® VILO™ Master Mix (Invitrogen by Life Technologies). cDNA was diluted to 2-5 ng/µL, and 10-25 ng cDNA was amplified with the TAQMAN® Gene Expression Master Mix (Applied Biosystems by Life Technologies) using the ABI 7900HT Sequence Detection System (Applied Biosystems), using the primers and Taqman MGB probes (Applied Biosystems) or BHQ1/BHQ-Plus probes (Biosearch Technologies) depicted in Table 4 according to manufacturer's instructions. The relative expression of each gene was normalized to the murine TCR beta constant 1 (TRBC1) control.

TABLE 4

Primers and Probes Used for Detecting RNA Expression of TCRβ V Segments and Constant Region in Humanized TCR Mice by Real-Time PCR (TAQMAN ™)

| TRBV | Sense Primer (5'-3') Sequence | SEQ ID NO | Antisense Primer (5'-3') Sequence | SEQ ID NO | Probe (5'-3') Sequence | SEQ ID NO |
|---|---|---|---|---|---|---|
| hTRBV 18 | CCGGCGTCATGCAGAA | 28 | GGGCTGCATCTCAGTCTTGC | 29 | FAM-CACCTGGTCAGGAGGAGG-MGB | 30 |
| hTRBV 19 | GGAATCACTCAGTCCCCAAAG | 31 | ATTCTGTTCACAACTCAGGGTCA | 32 | FAM-TCAGAAAGGAAGGACAGAAT-MGB | 33 |
| hTRBV 20 | CGAGCAAGGCGTCGAGAA | 34 | GGACAAGGTCAGGCTTGCA | 35 | FAM-ACAAGTTTCTCATCAACC-MGB | 36 |
| hTRBV 24 | TGTTACCCAGACCCCAAGGA | 37 | TCTGAGAACATTCCAGCATAATCCT | 38 | FAM-TAGGATCACAAAGACAGGAA-MGB | 39 |
| hTRBV 25 | TCCCCTGACCCTGGAGTCT | 40 | TGCTGGCACAGAGGTACTGAGA | 41 | FAM-CAGGCCCTCACATAC-MGB | 42 |
| hTRBV 27 | AAGCCCAAGTGACCCAGAA | 43 | ATTCTGAGAACAAGTCACTGTTAACTTC | 44 | FAM-CTCATCACAGTGACTGGAA-MGB | 45 |
| hTRBV 28 | GTGAAAGTAACCCAGAGCTCGAG | 46 | ATCCTGGACACATTCCAGAAAAAC | 47 | FAM-ATATCTAGTCAAAAGGACGGGA-MGB | 48 |
| hTRBV 29 | TGTCATTGACAAGTTTCCCATCAG | 49 | TGCTGTCTTCAGGGCTCATG | 50 | FAM-TCAACTCTGACTGTGAGCA-MGB | 51 |
| mTRBC 1 | CAGCCGCCTGAGGGTCTCT | 52 | GCCACTTGTCCTCCTCTGAAAG | 53 | FAM-TACCTTCTGGCACAATCCTCGCA-BHQ | 54 |

Figure 16A:
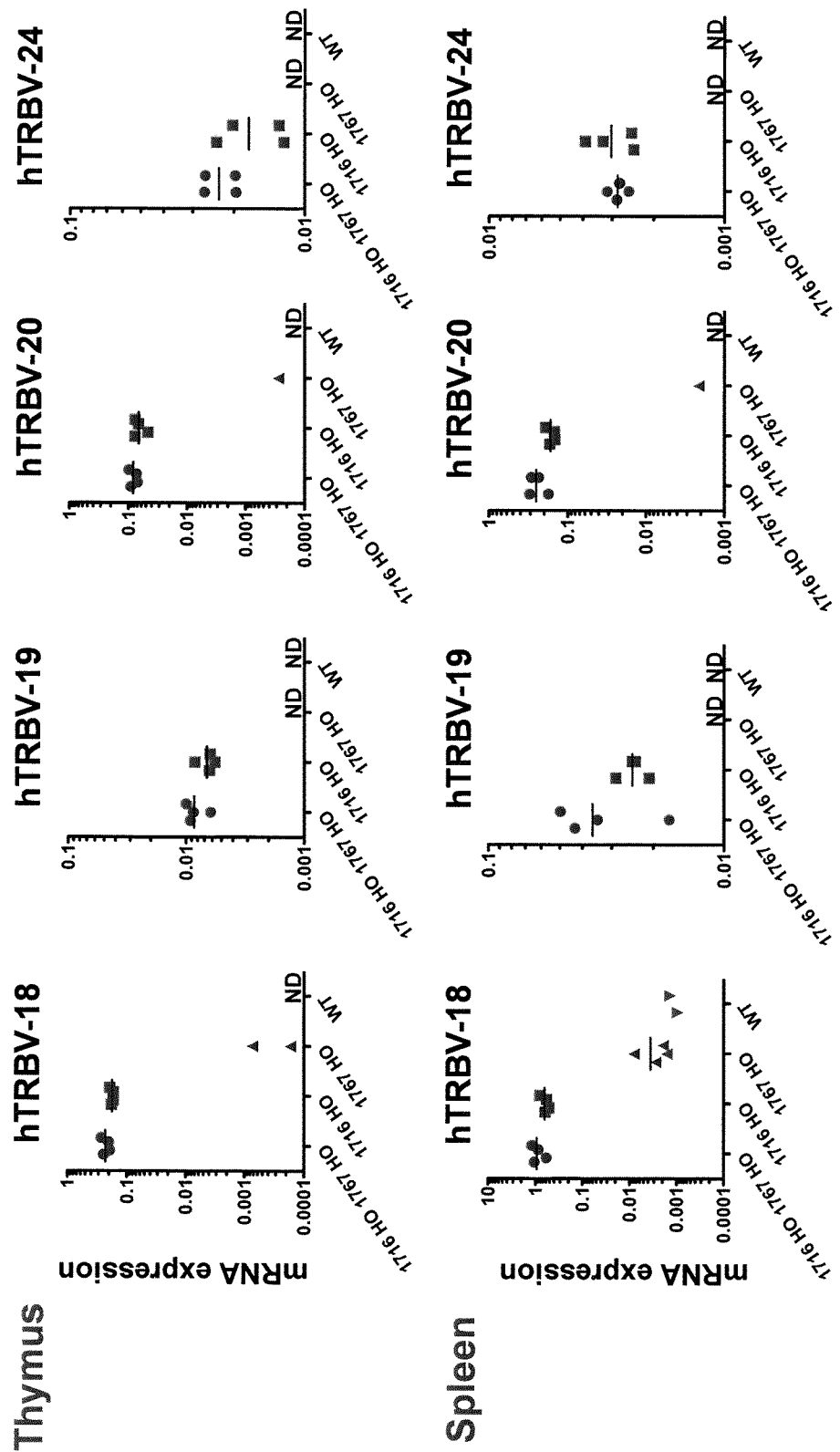
FIGS. 16A and 16B depict mRNA expression (Y axes) of various human TCRβ V segments present in WT, hTCRα (1767 HO); hTCRβ (1716 HO); or hTCRα/β (1716 HO 1767 HO) mice in thymic or splenic T cells.
Figure 16B:
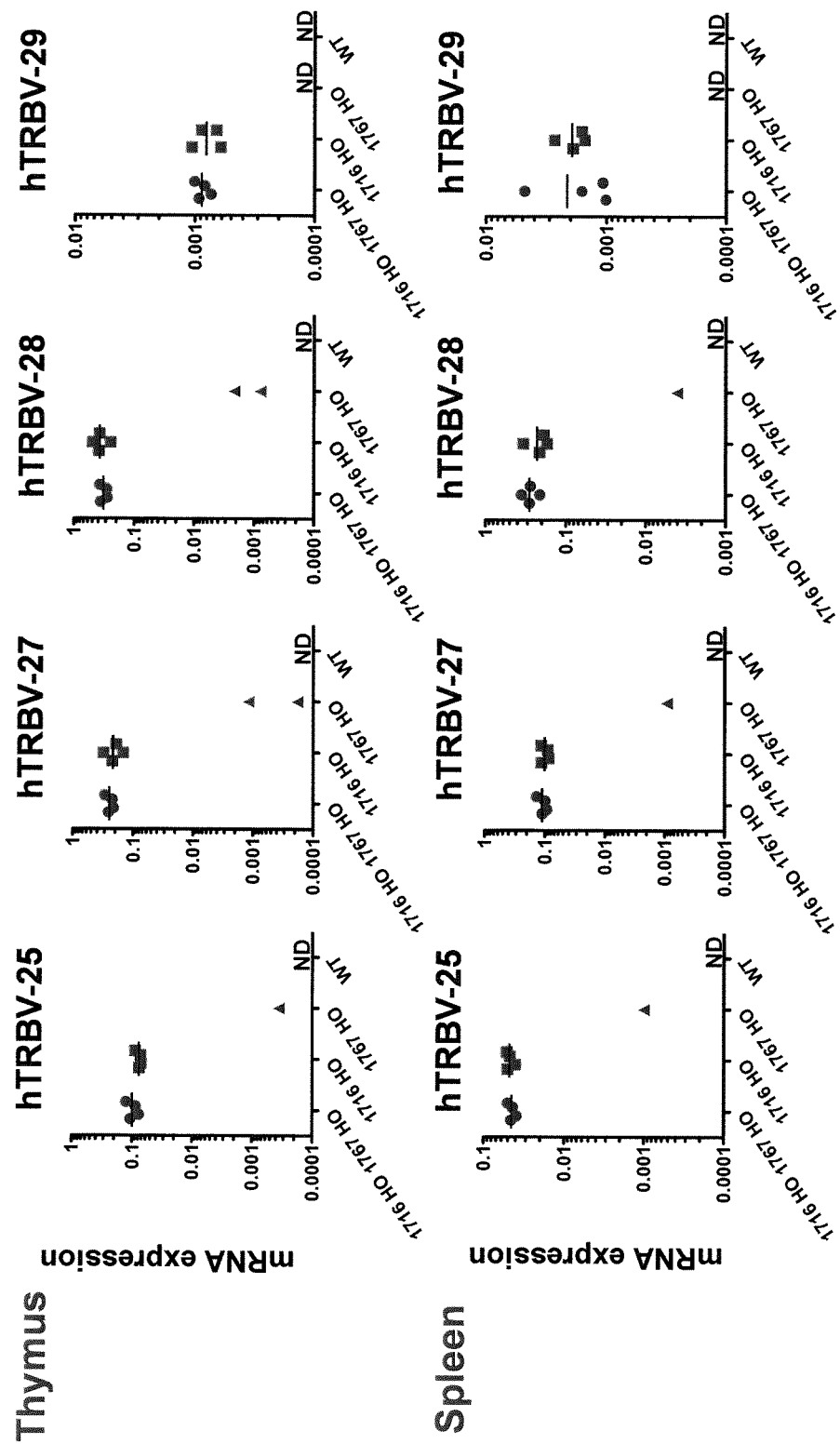

As demonstrated in FIGS. 16A-B, mice homozygous for humanized TCRβ locus (1716 HO) and mice homozygous for both humanized TCRβ and TCRα locus (1716 HO 1767 HO) exhibited RNA expression of various human TCRβ segments in both the thymus and the spleen. Mice also exhibited RNA expression of mouse TRBV-1 and TRBV-31 segments (data not shown), but no mouse TRBV-1 protein was detected by flow cytometry (data not shown).

Mouse TRBV-31 segment is replaced with human TRBV-30 segment as demonstrated in FIG. 8F, and mice are generated from MAID 6192 ES cells as described herein. The spleens and thymi of resulting homozygous animals are tested for utilization of human Vβ segments, including TRBV-30, by flow cytometry and/or real-time PCR as described herein. mTRBV-1 segment may also be deleted.

Example 9

T Cell Development in Mice Homozygous for 23 Human TCR Vα Segments

Homozygous humanized TCRα mice characterized in the previous examples contained 8 human Vα segments and 61 human Jα segments (1767 HO, see FIG. 3). Homozygous humanized TCRα mice comprising 23 human Vα segments and 61 human Jα segments (1979 HO, see FIG. 3) were tested for their ability to generate splenic CD3+ T cells and exhibit T cell development in the thymus.

Figure 17:
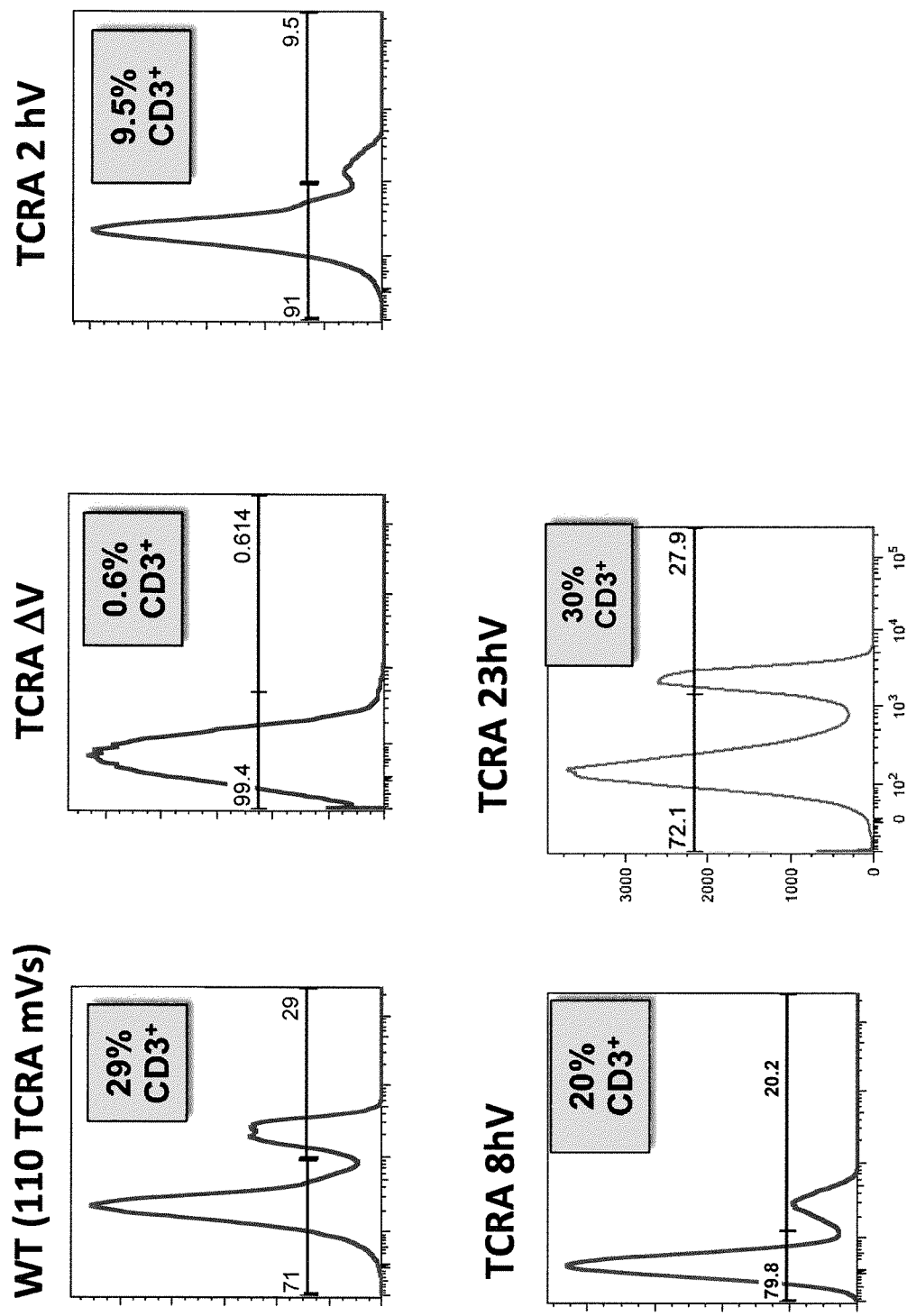
FIG. 17 depicts representative FACS histograms of spleen cells (where Y axis is number of cells, X axis is mean fluorescence intensity, and the gate shows frequency of CD3+ T cells within the single lymphocyte population) stained with anti-CD3 antibody in a WT mouse, a mouse homozygous for a deleted TCRα locus (TCRA ΔV), a mouse homozygous for deleted TCRα locus with 2 human V segments and 61 human J segments (TCRA 2 hV; MAID 1626 of FIG. 3), a mouse homozygous for deleted TCRα locus with 8 human V segments and 61 human J segments (TCRA 8 hV; MAID 1767 of FIG. 3), and a mouse homozygous for deleted TCRα locus with 23 human V segments and 61 human J segments (TCRA 23 hV; MAID 1979 of FIG. 3).
Figure 19:
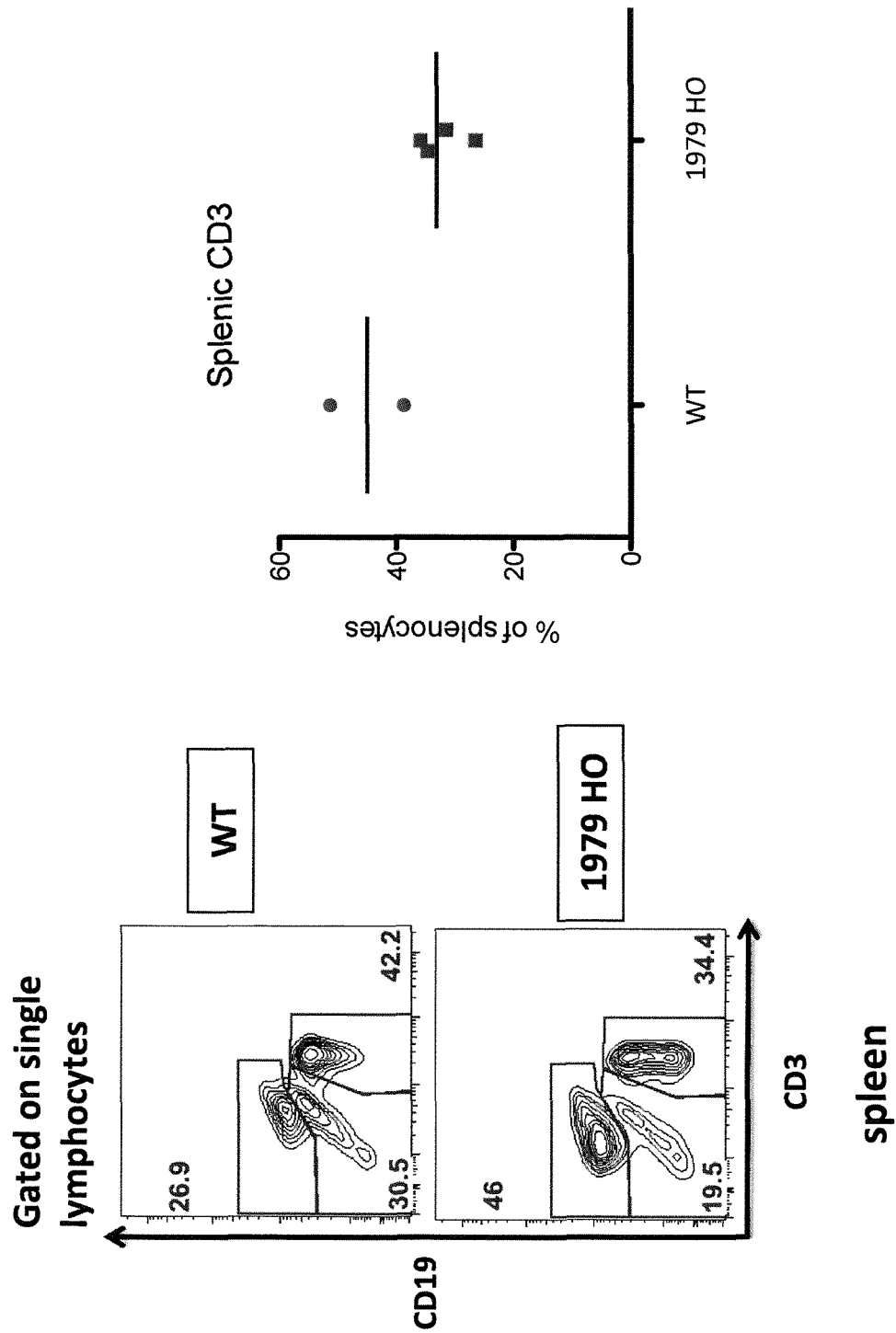
FIG. 19, at left panel, is a representative FACS analysis of splenic lymphocytes from a WT or 1979 HO mouse stained either with anti-CD19 or anti-CD3 antibodies; at right panel, are graphs of percent splenocytes (Y axis) obtained from WT and 1979 HO mice (n=4) that are CD3+.

Experimental data was obtained using flow cytometry using appropriate antibodies as described in the preceding examples. As depicted in FIG. 17, a mouse homozygous for 23 human Vα segments and 61 human Jα segments produced a significant number of splenic CD3+ T cells, and the percent of peripheral CD3+ T cells was comparable to that of the wild type animals (FIG. 19).

Figure 18:
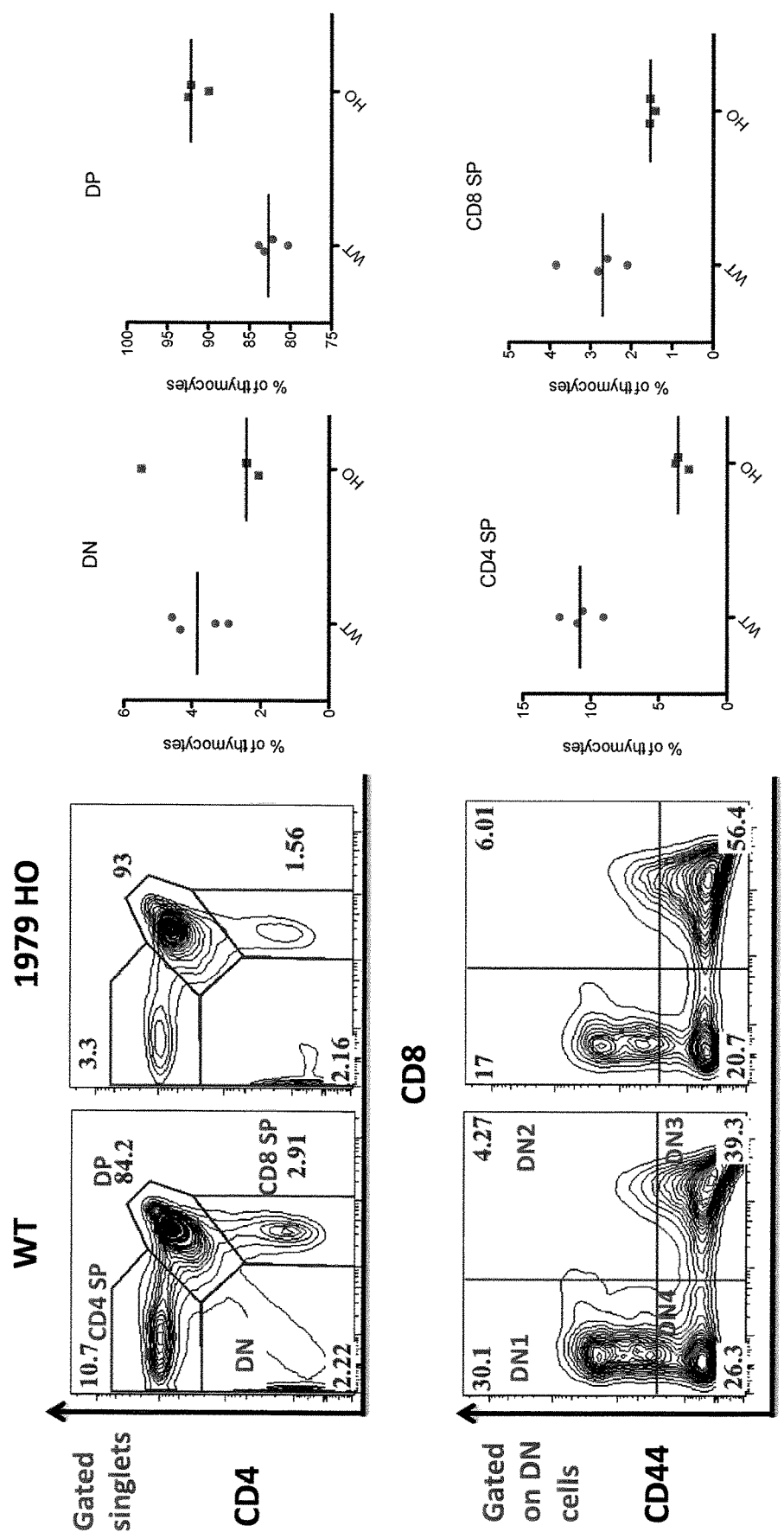
FIG. 18, at left top panel, is a representative FACS analysis of CD3+ T cells of the thymus obtained from either a WT or homozygous hTCRα mouse with 23 human V segments and 61 human J segments (1979 HO) stained with either anti-CD4 (Y axis) or anti-CD8 (X axis) antibody; at left bottom panel, is a FACS analysis of DN T cells from either a WT or 1979 mouse stained with either anti-CD44 (Y axis) or anti-CD25 (X axis); at right panel are graphs of percent of thymocytes (Y axis) that are DN, DP, CD4 SP, or CD8 SP in either WT or 1979 HO mice (n=4).

Moreover, thymocytes in 1979 HO mice were able to undergo T cell development and contained T cells at DN1, DN2, DN3, DN4, DP, CD4 SP, and CD8 SP stages (FIG. 18).

Example 10

T Cell Development and Differentiation in Mice Homozygous for a Complete Repertoire of Both Human TCRα and TCR β Variable Region Segments Mice homozygous for a complete repertoire of human TCRα variable region segments (i.e., 54 human Vα and 61 human Jα) and homozygous for a complete repertoire of human TCRβ variable region segments (67 human Vβ, 2 human Dβ, and 14 human Jβ), "1771 HO 6192 HO" (see FIGS. 3 and 7), are tested for their ability to produce thymocytes that undergo normal T cell development, produce T cells that undergo normal T cell differentiation in the periphery, and utilize the complete repertoire of their human Vα and V3 segments.

Flow cytometry is conducted to determine the presence of DN1, DN2, DN3, DN4, DP, CD4 SP and CD8 SP T cells in the thymus using anti-mouse CD4, CD8, CD25, and CD44 antibodies as described above in Examples 5 and 6. Flow cytometry is also conducted to determine the number of CD3+ T cells in the periphery, as well as to evaluate T cell differentiation in the periphery (e.g., presence of effector and memory T cells in the periphery). The experiment is conducted using anti-mouse CD3, CD19, CD4, CD8, CD44, and CD62L antibodies as described above in Examples 5 and 7.

Finally, flow cytometry and/or real-time PCR are conducted to determine whether T cells in 1771 HO 6192 HO mice utilize a complete repertoire of TCRβ and TCRA V segments. For protein expression using flow cytometry, TCRβ repertoire kit (IOTEST® Beta Mark, Beckman Coulter), containing anti-human hTCRBV-specific antibodies, is utilized (see Example 8). For RNA expression using real-time PCR, cDNAs from spleens or thymi are amplified using human TCR-V primers and Taqman probes, according to manufacturers instructions and as described above in Example 8.

EQUIVALENTS

Those skilled in the art will recognize, or be able to ascertain using no more than routine experimentation, many equivalents of the specific embodiments of the invention described herein. Such equivalents are intended to be encompassed by the following claims.

Entire contents of all non-patent documents, patent applications and patents cited throughout this application are incorporated by reference herein in their entirety.

What is claimed is:

1. A genetically modified mouse whose genome comprises:
   (i) a homozygous replacement of all endogenous T-cell receptor (TCR) variable α (Vα) gene segments with at least two functional unrearranged human TCR Vα gene segments and
   (ii) a homozygous replacement of all endogenous TCR joining α (Jα) gene segments with a complete repertoire of unrearranged human TCR Jα gene segments, wherein:
   (a) the at least two functional unrearranged human TCR Vα gene segments and the complete repertoire of unrearranged human TCR Ja gene segments are operably linked to each other and a nucleic acid sequence encoding an endogenous TCR constant α (Cα) domain,
   (b) the mouse comprises a T cell that expresses a chimeric TCR α polypeptide on its surface, wherein the chimeric TCR α polypeptide comprises a human TCR α variable domain operably linked to the endogenous TCR Cα domain, and
   (c) at least 9.5% of splenocytes in the mouse express CD3.

2. The genetically modified mouse of claim 1, wherein the at least two functional unrearranged human TCR Vα gene segments comprise an unrearranged human TRAV40 gene segment and an unrearranged human TRAV41 gene segment.

3. The genetically modified mouse of claim 1, wherein the human TCR α variable domain is derived from:
   a human TRAV40 gene segment,
   a human TRAV41 gene segment,
   a human TRAV39 gene segment,
   a human TRAV35 gene segment,
   a human TRAV34 gene segment,
   a human TRAV22 gene segment,
   a human TRAV21 gene segment,
   a human TRAV13-2 gene segment,
   a human TRAV8.5 gene segment,
   a human TRAV6 gene segment,
   a human TRAV5 gene segment, or
   a human TRAV1-1 gene segment.

4. The genetically modified mouse of claim 1, wherein the replacement of endogenous TCR Vα gene segments and/or the replacement of endogenous TCR Jα gene segments introduces the nucleotide sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and/or SEQ ID NO:13.

5. A genetically modified mouse whose genome comprises:
   (i) a homozygous replacement of all endogenous TCR variable β(Vβ) gene segments located between a 5' trypsinogen cluster and a 3' trypsinogen cluster with at least eight functional unrearranged human TCR Vβ gene segments,
   (ii) a homozygous replacement of an endogenous TCR diversity β (Dβ) 1 gene segment with an unrearranged human TCR D β1 gene segment and a homozygous replacement of an endogenous TCR Dβ2 gene segment with an unrearranged human TCR Dβ2 gene segment, and
   (iii) a homozygous replacement of all endogenous TCR joining β(Jβ) gene segments with a complete repertoire of unrearranged human TCR Jβ gene segments,
   wherein:
   (a) the at least eight functional unrearranged human TCR Vβ gene segments, the unrearranged human TCR Dβ 1 and unrearranged human TCR Dβ 2 gene segments, and the complete repertoire of unrearranged human TCR Jβ gene segments are operably linked to each other and a nucleic acid sequence encoding an endogenous TCR constant β(Cβ) domain,
   (b) the mouse comprises a T cell that expresses a chimeric TCR polypeptide on its surface, wherein the chimeric TCR β polypeptide comprises a human TCR β variable domain operably linked to the endogenous TCR Cβ domain, and
   (c) at least 20% of splenocytes in the mouse express CD3.

6. The genetically modified mouse of claim 5, wherein the mouse retains an endogenous TCR Vβ gene segment (i) upstream of the 5' trypsinogen cluster and/or (ii) downstream of the nucleic acid sequence encoding the endogenous TCR Cβ domain.

7. The genetically modified mouse of claim 5, wherein the at least eight functional unrearranged human TCR Vβ gene segments comprise a complete repertoire of unrearranged human TCR Vβ gene segments.

8. The genetically modified mouse of claim 5, wherein the genome further comprises:
  (iv) a homozygous replacement of all endogenous TCR Vα gene segments with at least seven functional unrearranged human TCR Vα gene segments and
  (v) a homozygous replacement of all endogenous TCR Jα gene segments with a complete repertoire of unrearranged human TCR Jα gene segments,
  wherein;
  (a) the at least seven functional unrearranged human TCR Vα gene segments and the complete repertoire of unrearranged human TCR Jα gene segments are operably linked to each other and a nucleic acid sequence encoding an endogenous TCR Cα domain, and
  (b) the mouse comprises a T cell that expresses a chimeric TCR on its surface, wherein the chimeric TCR comprises:
    a chimeric TCR α polypeptide comprising a human TCR α variable domain operably linked to the endogenous TCR Cα domain, and
    a chimeric TCR β polypeptide comprising a human TCR β variable domain operably linked to the endogenous TCR Cβ domain.

9. The genetically modified mouse of claim 8, wherein the mouse retains an endogenous TCR Vβ gene segment Qupstream of the 5' trypsinogen cluster and/or (ii) downstream of the nucleic acid sequence encoding the endogenous TCR Cβ domain.

10. The genetically modified mouse of claim 8, wherein:
  (i) the at least eight functional unrearranged human TCR Vβ gene segments comprises a complete repertoire of unrearranged human TCR Vβ gene segments, and
  (ii) the at least seven functional unrearranged human TCR Vα gene segments comprises a complete repertoire of unrearranged human TCR Vα gene segments.

11. The genetically modified mouse of claim 8, wherein the mouse comprises a trypsinogen gene between the at least eight functional unrearranged human TCR Vβ gene segments and the functional unrearranged human TCR Dβ1 gene segments.

12. The genetically modified mouse of claim 8, wherein
  (A) the human TCR α variable domain is derived from:
    a human TRAV40 gene segment,
    a human TRAV41 gene segment,
    a human TRAV39 gene segment,
    a human TRAV35 gene segment,
    a human TRAV34 gene segment,
    a human TRAV22 gene segment,
    a human TRAV21 gene segment,
    a human TRAV13-2 gene segment,
    a human TRAV8.5 gene segment,
    a human TRAV6 gene segment,
    a human TRAV5 gene segment, or
    a human TRAV1-1 gene segment; and/or
  (B) the human TCR β variable domain is derived from
    a human TRBV18 gene segment,
    a human TRBV19 gene segment,
    a human TRBV20 gene segment,
    a human TRBV24 gene segment,
    a human TRBV25 gene segment,
    a human TRBV27 gene segment,
    a human TRBV28 gene segment, or
    a human TRBV29 gene segment.

13. The genetically modified mouse of claim 8, wherein
  (A) the replacement of the endogenous TCR Vα gene segments and/or the replacement of the endogenous TCR Jα gene segments introduces the nucleotide sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and/or SEQ ID NO:13; and/or
  (B) the replacement of the endogenous TCR Vβ gene segments, the replacement of the endogenous TCR Dβ gene segments, and/or the replacement of endogenous TCR Jβ gene segments introduces the nucleotide sequence of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26 and/or SEQ ID NO:27.

14. The genetically modified mouse of claim 5, wherein the mouse comprises a trypsinogen gene between the at least eight functional unrearranged human TCR Vβ1 gene segments and the functional_unrearranged human TCR Dβ1 gene segment.

15. The genetically modified mouse of claim 5, wherein the human TCR β variable domain is derived from
    a human TRBV18 gene segment,
    a human TRBV19 gene segment,
    a human TRBV20 gene segment,
    a human TRBV24 gene segment,
    a human TRBV25 gene segment,
    a human TRBV27 gene segment,
    a human TRBV28 gene segment, or
    a human TRBV29 gene segment.

16. The genetically modified mouse of claim 5, wherein the replacement of the endogenous TCR Vβ gene segments, the replacement of the endogenous TCR Dβ gene segments, and/or the replacement of the endogenous TCR Jβ gene segments introduces the nucleotide sequence of set forth as SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26 and/or SEQ ID NO:27.

17. A method for making a genetically modified mouse that expresses on a surface of a T cell, a TCR comprising a chimeric TCR α polypeptides and chimeric TCR f3 polypeptides, the method comprising:
  (A) obtaining a first mouse whose genome comprises:
    (i) a homozygous replacement of all endogenous TCR Vα gene segments with at least seven functional unrearranged human TCR Vα gene segments and
    (ii) a homozygous replacement of all endogenous TCR Jα gene segments with a complete repertoire of unrearranged human TCR Jα gene segments,
    wherein the at least seven functional unrearranged human TCR Vα gene segments and the complete repertoire of unrearranged human TCR Jα gene segments are operably linked to each other and a nucleic acid sequence encoding the endogenous TCR Cα domain, and
  (B) obtaining a second mouse whose genome comprises:
    (i) a homozygous replacement of all endogenous TCR Vβ gene segments located between a 5' trypsinogen cluster and a 3' trypsinogen cluster with at least eight functional unrearranged human TCR Vβ gene segments,
    (ii) a homozygous replacement of an endogenous TCR Dβ1 gene segment with an unrearranged human TCR Dβ1 gene segment and a homozygous replacement of an endogenous TCR Dβ2 gene segment with an unrearranged human TCR Dβ2 gene segment, and (iii) a homozygous replacement of all endogenous TCR Jβ gene segments with a complete repertoire of unrearranged human TCR Jβ gene segments,
wherein the at least eight functional unrearranged human TCR Vβ gene segments, the unrearranged human TCR Dβ1 and TCR Dβ2 gene segments, and the complete repertoire of unrearranged human TCR Jβ gene segments are operably linked to each other and a nucleic acid sequence encoding the endogenous TCR Cβ domain, and
(C) breeding the first mouse and the second mouse to obtain a genetically modified mouse,
wherein the genetically modified mouse expresses;
a chimeric TCR α polypeptide comprising a human TCR α variable domain operably linked to the endogenous TCR Cα domain and
a chimeric TCR β polypeptide comprising a human TCR β variable domain operably linked to the endogenous TCR Cβ domain.

18. The method of claim 17, wherein:

(A) the at least seven functional unrearranged human TCR Vα gene segments comprise a complete repertoire of unrearranged human TCR Vα gene segments and/or (B) the at least eight functional unrearranged human TCR Vβ gene segments comprise a complete repertoire of unrearranged human TCR Vβ gene segments.

19. The method of claim 18, wherein (A) the at least seven functional unrearranged human TCR Vα gene segments comprise a complete repertoire of unrearranged human TCR Vα gene segments, and (B) the at least eight functional unrearranged human TCR Vβ gene segments comprise a complete repertoire of unrearranged human TCR Vβ gene segments from TRBV1 to TRBV29-1.

* * * * *

UNITED STATES PATENT AND TRADEMARK OFFICE
CERTIFICATE OF CORRECTION

PATENT NO. : 11,528,895 B2
APPLICATION NO. : 14/799355
DATED : December 20, 2022
INVENTOR(S) : Lynn Macdonald et al.

It is certified that error appears in the above-identified patent and that said Letters Patent is hereby corrected as shown below:

In the Claims

Claim 5, Line 10, Column 64, Line 38:
human TCR D β1 gene segment
Should be:
--human TCR Dβ1 gene segment--

Claim 5, Line 19, Column 64, Line 47:
human TCR D β1
Should be:
--human TCR Dβ1--

Claim 5, Line 20, Column 64, Line 48:
human TCR D β2 gene segments,
Should be:
--human TCR Dβ2 gene segments,--

Claim 5, Line 26, Column 64, Line 54:
TCR polypeptide
Should be:
--TCR β polypeptide--

Claim 9, Line 2, Column 65, Line 25:
gene segment Qup-
Should be:
--gene segment (i) up--

Claim 11, Line 5, Column 65, Line 40:
gene segments.

Signed and Sealed this
Nineteenth Day of December, 2023

Katherine Kelly Vidal
*Director of the United States Patent and Trademark Office*

CERTIFICATE OF CORRECTION (continued)
U.S. Pat. No. 11,528,895 B2

Should be:
--gene segment.--

Claim 14, Line 4, Column 66, Line 18:
functional_unrearranged
Should be:
--functional unrearranged--

Claim 16, Line 5, Column 66, Line 34:
nucleotide sequence of set forth as
Should be:
--nucleotide sequence of--

Claim 17, Line 2, Column 66, Line 41:
that expresses on a surface of a T cell, a TCR comprising a
Should be:
--that expresses--

Claim 17, Line 3, Column 66, Line 42:
TCR f3
Should be:
--TCR β--

Claim 17, Line 41, Column 67, Line 12:
mouse expresses;
Should be:
--mouse expresses:--

SEQUENCE LISTING

```
<160> NUMBER OF SEQ ID NOS: 54

<210> SEQ ID NO 1
<211> LENGTH: 100
<212> TYPE: DNA
<213> ORGANISM: Artificial Sequence
<220> FEATURE:
<223> OTHER INFORMATION: Synthetic

<400> SEQUENCE: 1
atggagtagt cagaacacac tcttcagaag ggactcctga tttcaaaggg ggtaccgggc      60
cccccctcga ggtcgacata acttcgtata gcatacatta                          100

<210> SEQ ID NO 2
<211> LENGTH: 108
<212> TYPE: DNA
<213> ORGANISM: Artificial Sequence
<220> FEATURE:
<223> OTHER INFORMATION: Synthetic

<400> SEQUENCE: 2
ggccatgcat ataacttcgt atagcataca ttatacgaag ttataccggt gcgatcgcgc      60
gcttccctct tctaaccact aattcaaaaa ggattgtaag taatgttt                 108

<210> SEQ ID NO 3
<211> LENGTH: 145
<212> TYPE: DNA
<213> ORGANISM: Artificial Sequence
<220> FEATURE:
<223> OTHER INFORMATION: Synthetic

<400> SEQUENCE: 3
agacagaccc ctaaacacct ccaaattaaa agcggcaaag agataaggtt ggagctccac      60
cgcggtggcg gccgccaccg cggtggagct cgaggtttcc ggtacttaac aacagagcac    120
agatttagtg gtgagggact ctctc                                          145

<210> SEQ ID NO 4
<211> LENGTH: 100
<212> TYPE: DNA
<213> ORGANISM: Artificial Sequence
<220> FEATURE:
```

<223> OTHER INFORMATION: Synthetic

<400> SEQUENCE: 4

```
atggagtagt cagaacacac tcttcagaag ggactcctga tttcaaaggg ggtaccgggc    60
ccccccctcga ggtcgacata acttcgtata gcatacatta                        100
```

<210> SEQ ID NO 5
<211> LENGTH: 109
<212> TYPE: DNA
<213> ORGANISM: Artificial Sequence
<220> FEATURE:
<223> OTHER INFORMATION: Synthetic

<400> SEQUENCE: 5

```
ggccatgcat ataacttcgt atagcataca ttatacgaag ttataccggt gcgatcgctc    60
aagcatgcaa gggtaacata tgttatgaga ttatattttc tttatctca              109
```

<210> SEQ ID NO 6
<211> LENGTH: 100
<212> TYPE: DNA
<213> ORGANISM: Artificial Sequence
<220> FEATURE:
<223> OTHER INFORMATION: Synthetic

<400> SEQUENCE: 6

```
atggagtagt cagaacacac tcttcagaag ggactcctga tttcaaaggg gggtaccggg    60
cccccctcg agaagttcct attccgaagt tcctattctc                         100
```

<210> SEQ ID NO 7
<211> LENGTH: 108
<212> TYPE: DNA
<213> ORGANISM: Artificial Sequence
<220> FEATURE:
<223> OTHER INFORMATION: Synthetic

<400> SEQUENCE: 7

```
gttcctattc cgaagttcct attctctaga aagtatagga acttcctagg gcgatcgctc    60
ctctccaggc tcgaattagt attacagttg aggcacgttg tcctcccg               108
```

<210> SEQ ID NO 8
<211> LENGTH: 100
<212> TYPE: DNA
<213> ORGANISM: Artificial Sequence
<220> FEATURE:
<223> OTHER INFORMATION: Synthetic

<400> SEQUENCE: 8

```
atggagtagt cagaacacac tcttcagaag ggactcctga tttcaaaggg ggtaccgggc    60
ccccccctcga ggtcgacata acttcgtata gcatacatta                        100
```

<210> SEQ ID NO 9
<211> LENGTH: 108
<212> TYPE: DNA
<213> ORGANISM: Artificial Sequence
<220> FEATURE:
<223> OTHER INFORMATION: Synthetic

<400> SEQUENCE: 9

```
ggccatgcat ataacttcgt atagcataca ttatacgaag ttataccggt gcgatcgccg    60
cctccatttc cttcatagga aacatgaagt gaatggggct gtgtgtgt               108
```

```
<210> SEQ ID NO 10
<211> LENGTH: 100
<212> TYPE: DNA
<213> ORGANISM: Artificial Sequence
<220> FEATURE:
<223> OTHER INFORMATION: Synthetic

<400> SEQUENCE: 10
atggagtagt cagaacacac tcttcagaag ggactcctga tttcaaaggg ggtaccgggc    60 ccccccctcga ggtcgacata acttcgtata gcatacatta                        100

<210> SEQ ID NO 11
<211> LENGTH: 108
<212> TYPE: DNA
<213> ORGANISM: Artificial Sequence
<220> FEATURE:
<223> OTHER INFORMATION: Synthetic

<400> SEQUENCE: 11
ggccatgcat ataacttcgt atagcataca ttatacgaag ttataccggt gcgatcgctg    60
ggagcacgtt ccattattat aacaactttc tgaacacaag agggcagt                108

<210> SEQ ID NO 12
<211> LENGTH: 100
<212> TYPE: DNA
<213> ORGANISM: Artificial Sequence
<220> FEATURE:
<223> OTHER INFORMATION: Synthetic

<400> SEQUENCE: 12
atggagtagt cagaacacac tcttcagaag ggactcctga tttcaaaggg ggtaccgggc    60 ccccccctcga ggtcgacata acttcgtata gcatacatta                        100

<210> SEQ ID NO 13
<211> LENGTH: 108
<212> TYPE: DNA
<213> ORGANISM: Artificial Sequence
<220> FEATURE:
<223> OTHER INFORMATION: Synthetic

<400> SEQUENCE: 13
ggccatgcat ataacttcgt atagcataca ttatacgaag ttataccggt gcgatcgctt    60
taaggtgagg aggcaggcaa taccccctct ccaccgcatt ctcaatcc                108

<210> SEQ ID NO 14
<211> LENGTH: 100
<212> TYPE: DNA
<213> ORGANISM: Artificial Sequence
<220> FEATURE:
<223> OTHER INFORMATION: Synthetic

<400> SEQUENCE: 14
gggggggtgg ggtggaggag gagggtacag catctcctct ccttcctctc tggtaccgaa    60
gttcctattc cgaagttcct attctctaga aagtatagga                         100

<210> SEQ ID NO 15
<211> LENGTH: 108
<212> TYPE: DNA
<213> ORGANISM: Artificial Sequence
<220> FEATURE:
<223> OTHER INFORMATION: Synthetic

<400> SEQUENCE: 15
```

```
gaagttccta ttctctagaa agtataggaa cttcctaggg tttcaccggt gcgatcgcgt    60
gaatatacta aaaaccactt aattatatat ttgaaagggt ggatgtta               108
```

<210> SEQ ID NO 16
<211> LENGTH: 108
<212> TYPE: DNA
<213> ORGANISM: Artificial Sequence
<220> FEATURE:
<223> OTHER INFORMATION: Synthetic
<400> SEQUENCE: 16

```
ctctctccta cccagctcct ctcacacgag cctgaaggcc ctgccaaggt ggcgcgcctt    60
tcaaattgtt gttgagttca aagtgggcaa cagaaaaggg ggtgtgag               108
```

<210> SEQ ID NO 17
<211> LENGTH: 130
<212> TYPE: DNA
<213> ORGANISM: Artificial Sequence
<220> FEATURE:
<223> OTHER INFORMATION: Synthetic
<400> SEQUENCE: 17

```
aataaatagt aaatttctgt agaatcataa tgaggtctag accccgggc tcgataacta    60 taacggtcct aaggtagcga atggcgcgt aatcaagccc agctcttcat gctgcatttt  120
tatcttcttt                                                        130
```

<210> SEQ ID NO 18
<211> LENGTH: 100
<212> TYPE: DNA
<213> ORGANISM: Artificial Sequence
<220> FEATURE:
<223> OTHER INFORMATION: Synthetic
<400> SEQUENCE: 18

```
ttgactcggg ggtgcctggg tttgactgca atgatcagtt gctgggaagg accggtataa    60
cttcgtataa tgtatgctat acgaagttat atgcatggcc                       100
```

<210> SEQ ID NO 19
<211> LENGTH: 100
<212> TYPE: DNA
<213> ORGANISM: Artificial Sequence
<220> FEATURE:
<223> OTHER INFORMATION: Synthetic
<400> SEQUENCE: 19

```
ccggcgcgcc ataacttcgt ataatgtatg ctatacgaag ttatgtcgac ataaggtaag    60
acagagtcgt cccttcccat ctggaaccct ctacctttct                       100
```

<210> SEQ ID NO 20
<211> LENGTH: 107
<212> TYPE: DNA
<213> ORGANISM: Artificial Sequence
<220> FEATURE:
<223> OTHER INFORMATION: Synthetic
<400> SEQUENCE: 20

```
gttgatgaat cataaaagaa gagatattca agaaaaggat ggccacactg cggccgcaga    60
ggtattcaag gaaaatgcag actcttcacg taagagggat gagggggc              107
```

<210> SEQ ID NO 21
<211> LENGTH: 100

<212> TYPE: DNA
<213> ORGANISM: Artificial Sequence
<220> FEATURE:
<223> OTHER INFORMATION: Synthetic

<400> SEQUENCE: 21
tccccggagt cggagggtgg accggagctg gaggagctgc cgcggtggcg gccgatgcca    60
tttcattacc tctttctccg cacccgacat agataaagct                         100

<210> SEQ ID NO 22
<211> LENGTH: 100
<212> TYPE: DNA
<213> ORGANISM: Artificial Sequence
<220> FEATURE:
<223> OTHER INFORMATION: Synthetic

<400> SEQUENCE: 22 ggggggtgg ggtggaggag gagggtacag catctcctct ccttcctctc tggtaccgaa    60
gttcctattc cgaagttcct attctctaga aagtatagga                         100

<210> SEQ ID NO 23
<211> LENGTH: 108
<212> TYPE: DNA
<213> ORGANISM: Artificial Sequence
<220> FEATURE:
<223> OTHER INFORMATION: Synthetic

<400> SEQUENCE: 23
gaagttccta ttctctagaa agtataggaa cttcctaggg tttcaccggt gcgatcgcga    60
agcaattaac tgcccctggt ccagttgcct cctctgataa tgcattgt                108

<210> SEQ ID NO 24
<211> LENGTH: 100
<212> TYPE: DNA
<213> ORGANISM: Artificial Sequence
<220> FEATURE:
<223> OTHER INFORMATION: Synthetic

<400> SEQUENCE: 24 ggggggtgg ggtggaggag gagggtacag catctcctct ccttcctctc tggtaccgaa    60
gttcctattc cgaagttcct attctctaga aagtatagga                         100

<210> SEQ ID NO 25
<211> LENGTH: 108
<212> TYPE: DNA
<213> ORGANISM: Artificial Sequence
<220> FEATURE:
<223> OTHER INFORMATION: Synthetic

<400> SEQUENCE: 25
gaagttccta ttctctagaa agtataggaa cttcctaggg tttcaccggt gcgatcgcgt    60
tatctagtag acttaattaa ggatcgatcc ggcgcgccaa tagtcatg                108

<210> SEQ ID NO 26
<211> LENGTH: 100
<212> TYPE: DNA
<213> ORGANISM: Artificial Sequence
<220> FEATURE:
<223> OTHER INFORMATION: Synthetic

<400> SEQUENCE: 26
gttttccaga cttcaacttg actatcagcc agaaattcag tggcaaaccc ccacccagtc    60
cctaagtgaa ggcccctggg gagtatggtt agggctcagg        100

<210> SEQ ID NO 27
<211> LENGTH: 100
<212> TYPE: DNA
<213> ORGANISM: Artificial Sequence
<220> FEATURE:
<223> OTHER INFORMATION: Synthetic

<400> SEQUENCE: 27
cacccaccaa agaaagtgcc caggagaagg gcaaggagag agcagagcat agttcaagat        60
ggtctttgtc taggcttgtc tactctgcac ttgtacttcc        100

<210> SEQ ID NO 28
<211> LENGTH: 16
<212> TYPE: DNA
<213> ORGANISM: Artificial Sequence
<220> FEATURE:
<223> OTHER INFORMATION: Synthetic

<400> SEQUENCE: 28
ccggcgtcat gcagaa        16

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
gggctgcatc tcagtcttgc        20

<210> SEQ ID NO 30
<211> LENGTH: 18
<212> TYPE: DNA
<213> ORGANISM: Artificial Sequence
<220> FEATURE:
<223> OTHER INFORMATION: Synthetic

<400> SEQUENCE: 30
cacctggtca ggaggagg        18

<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31
ggaatcactc agtccccaaa g        21

<210> SEQ ID NO 32
<211> LENGTH: 23
<212> TYPE: DNA
<213> ORGANISM: Artificial Sequence
<220> FEATURE:
<223> OTHER INFORMATION: Synthetic

<400> SEQUENCE: 32
attctgttca caactcaggg tca        23

<210> SEQ ID NO 33
<211> LENGTH: 20

```
<212> TYPE: DNA
<213> ORGANISM: Artificial Sequence
<220> FEATURE:
<223> OTHER INFORMATION: Synthetic

<400> SEQUENCE: 33
tcagaaagga aggacagaat                                              20

<210> SEQ ID NO 34
<211> LENGTH: 18
<212> TYPE: DNA
<213> ORGANISM: Artificial Sequence
<220> FEATURE:
<223> OTHER INFORMATION: Synthetic

<400> SEQUENCE: 34
cgagcaaggc gtcgagaa                                                18

<210> SEQ ID NO 35
<211> LENGTH: 19
<212> TYPE: DNA
<213> ORGANISM: Artificial Sequence
<220> FEATURE:
<223> OTHER INFORMATION: Synthetic

<400> SEQUENCE: 35
ggacaaggtc aggcttgca                                               19

<210> SEQ ID NO 36
<211> LENGTH: 18
<212> TYPE: DNA
<213> ORGANISM: Artificial Sequence
<220> FEATURE:
<223> OTHER INFORMATION: Synthetic

<400> SEQUENCE: 36
acaagtttct catcaacc                                                18

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
tgttacccag accccaagga                                              20

<210> SEQ ID NO 38
<211> LENGTH: 25
<212> TYPE: DNA
<213> ORGANISM: Artificial Sequence
<220> FEATURE:
<223> OTHER INFORMATION: Synthetic

<400> SEQUENCE: 38
tctgagaaca ttccagcata atcct                                        25

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
```

-continued taggatcaca aagacaggaa                               20

<210> SEQ ID NO 40
<211> LENGTH: 19
<212> TYPE: DNA
<213> ORGANISM: Artificial Sequence
<220> FEATURE:
<223> OTHER INFORMATION: Synthetic

<400> SEQUENCE: 40
tcccctgacc ctggagtct                                19

<210> SEQ ID NO 41
<211> LENGTH: 22
<212> TYPE: DNA
<213> ORGANISM: Artificial Sequence
<220> FEATURE:
<223> OTHER INFORMATION: Synthetic

<400> SEQUENCE: 41
tgctggcaca gaggtactga ga                            22

<210> SEQ ID NO 42
<211> LENGTH: 15
<212> TYPE: DNA
<213> ORGANISM: Artificial Sequence
<220> FEATURE:
<223> OTHER INFORMATION: Synthetic

<400> SEQUENCE: 42
caggccctca catac                                    15

<210> SEQ ID NO 43
<211> LENGTH: 19
<212> TYPE: DNA
<213> ORGANISM: Artificial Sequence
<220> FEATURE:
<223> OTHER INFORMATION: Synthetic

<400> SEQUENCE: 43
aagcccaagt gacccagaa                                19

<210> SEQ ID NO 44
<211> LENGTH: 28
<212> TYPE: DNA
<213> ORGANISM: Artificial Sequence
<220> FEATURE:
<223> OTHER INFORMATION: Synthetic

<400> SEQUENCE: 44
attctgagaa caagtcactg ttaacttc                      28

<210> SEQ ID NO 45
<211> LENGTH: 19
<212> TYPE: DNA
<213> ORGANISM: Artificial Sequence
<220> FEATURE:
<223> OTHER INFORMATION: Synthetic

<400> SEQUENCE: 45
ctcatcacag tgactggaa                                19

<210> SEQ ID NO 46
<211> LENGTH: 23
<212> TYPE: DNA
<213> ORGANISM: Artificial Sequence

```
<220> FEATURE:
<223> OTHER INFORMATION: Synthetic

<400> SEQUENCE: 46
gtgaaagtaa cccagagctc gag                                            23

<210> SEQ ID NO 47
<211> LENGTH: 24
<212> TYPE: DNA
<213> ORGANISM: Artificial Sequence
<220> FEATURE:
<223> OTHER INFORMATION: Synthetic

<400> SEQUENCE: 47
atcctggaca cattccagaa aaac                                           24

<210> SEQ ID NO 48
<211> LENGTH: 22
<212> TYPE: DNA
<213> ORGANISM: Artificial Sequence
<220> FEATURE:
<223> OTHER INFORMATION: Synthetic

<400> SEQUENCE: 48
atatctagtc aaaaggacgg ga                                             22

<210> SEQ ID NO 49
<211> LENGTH: 24
<212> TYPE: DNA
<213> ORGANISM: Artificial Sequence
<220> FEATURE:
<223> OTHER INFORMATION: Synthetic

<400> SEQUENCE: 49
tgtcattgac aagtttccca tcag                                           24

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
tgctgtcttc agggctcatg                                                20

<210> SEQ ID NO 51
<211> LENGTH: 19
<212> TYPE: DNA
<213> ORGANISM: Artificial Sequence
<220> FEATURE:
<223> OTHER INFORMATION: Synthetic

<400> SEQUENCE: 51
tcaactctga ctgtgagca                                                 19

<210> SEQ ID NO 52
<211> LENGTH: 18
<212> TYPE: DNA
<213> ORGANISM: Artificial Sequence
<220> FEATURE:
<223> OTHER INFORMATION: Synthetic

<400> SEQUENCE: 52
agccgcctga gggtctct                                                  18
```

```
<210> SEQ ID NO 53
<211> LENGTH: 22
<212> TYPE: DNA
<213> ORGANISM: Artificial Sequence
<220> FEATURE:
<223> OTHER INFORMATION: Synthetic

<400> SEQUENCE: 53
gccacttgtc ctcctctgaa ag                                              22

<210> SEQ ID NO 54
<211> LENGTH: 23
<212> TYPE: DNA
<213> ORGANISM: Artificial Sequence
<220> FEATURE:
<223> OTHER INFORMATION: Synthetic

<400> SEQUENCE: 54
taccttctgg cacaatcctc gca                                             23
```